(12) United States Patent
Bury et al.

(10) Patent No.: US 8,450,484 B2
(45) Date of Patent: May 28, 2013

(54) TRPV4 ANTAGONISTS

(75) Inventors: Michael Jonathan Bury, King of Prussia, PA (US); Mui Cheung, King of Prussia, PA (US); Hilary Schenck Eidam, King of Prussia, PA (US); Ryan Michael Fox, King of Prussia, PA (US); Krista Goodman, King of Prussia, PA (US); Eric Steven Manas, King of Prussia, PA (US)

(73) Assignee: GlaxoSmithKline, LLC, Philadelphia, PA (US)

( * ) Notice: Subject to any disclaimer, the term of this patent is extended or adjusted under 35 U.S.C. 154(b) by 64 days.

(21) Appl. No.: 13/054,834

(22) PCT Filed: Jul. 24, 2009

(86) PCT No.: PCT/US2009/051674
§ 371 (c)(1),
(2), (4) Date: Jan. 19, 2011

(87) PCT Pub. No.: WO2010/011914
PCT Pub. Date: Jan. 28, 2010

(65) Prior Publication Data
US 2011/0130400 A1 Jun. 2, 2011

Related U.S. Application Data

(60) Provisional application No. 61/083,550, filed on Jul. 25, 2008.

(51) Int. Cl.
*C07D 401/14* (2006.01)
*C07D 403/14* (2006.01)

(52) U.S. Cl.
USPC ............ 544/333; 544/360; 544/373

(58) Field of Classification Search
USPC .......... 544/333, 360, 373
See application file for complete search history.

(56) References Cited

U.S. PATENT DOCUMENTS

| 6,293,945 | B1 | 9/2001 | Parins et al. |
| 6,677,336 | B2 | 1/2004 | Zablock et al. |
| 7,202,238 | B2 | 4/2007 | De Boer et al. |
| 2002/0049442 | A1 | 4/2002 | Roberts et al. |
| 2005/0054631 | A1 | 3/2005 | Jiang et al. |
| 2005/0165288 | A1 | 7/2005 | Rioux et al. |

FOREIGN PATENT DOCUMENTS

| EP | 0829232 | 3/1998 |
| WO | WO9808441 | 3/1998 |
| WO | WO00/12010 | 3/2000 |
| WO | WO02/053036 | 7/2002 |
| WO | WO2007/070865 | 6/2007 |
| WO | WO2009/036265 | 3/2009 |
| WO | WO2009/146177 | 12/2009 |
| WO | WO2009/146182 | 12/2009 |
| WO | WO2010/011912 | 1/2010 |

OTHER PUBLICATIONS

Cheung, et al. Document No. 152:27389, retrieved from CAPLUS. Dec. 3, 2009.*

* cited by examiner

*Primary Examiner* — Shawquia Young
(74) *Attorney, Agent, or Firm* — Linda E. Hall; John L. Lemanowicz

(57) ABSTRACT

The present invention relates to diazabicyclo[2.2.1]hept-2-yl analogs, pharmaceutical compositions containing them and their use as TRPV4 antagonists.

3 Claims, No Drawings

TRPV4 ANTAGONISTS

This application is a 371 of International Application No. PCT/US2009/051674, filed Jul. 24, 2009, which claims the benefit of U.S. Provisional Application No. 61/083,550, filed Jul. 25, 2008, which is incorporated herein in its entirety.

FIELD OF THE INVENTION

The present invention relates to diazabicyclo[2.2.1]hept-2-yl analogs, pharmaceutical compositions containing them and their use as TRPV4 antagonists.

BACKGROUND OF THE INVENTION

TRPV4 is a member of the Transient Receptor Potential (TRP) superfamily of cation channels and is activated by heat, demonstrating spontaneous activity at physiological temperatures (Guler et al. 2002. *J Neurosci* 22: 6408-6414). TRPV4 is also activated by physical cell stress/pressure (Strotmann et al. 2000. *Nat Cell Biol* 2: 695-702) through a mechanism involving phospholipase A2 activation, production of arachidonic acid and epoxyeicosatrienoic acid generation (Vriens et al. 2004. *Proc Natl Acad Sci USA* 101: 396-401).

Heart failure results in the decreased ability of the left ventricle to pump blood into the peripheral circulation as indicated by a reduced ejection fraction. This increases the end diastolic pressure and pulmonary blood pressure, placing the septal barrier at risk that serves to separate the circulatory aqueous environment and the alveolar airspaces of the lung. Increased pulmonary pressure results in the flow of fluid from the pulmonary circulation into the alveolar space resulting in lung edema/congestion, as is observed in patients with congestive heart failure.

TRPV4 is expressed in the lung (Delany et al. 2001. *Physiol. Genomics* 4: 165-174) and has been shown to mediate $Ca^{2+}$ entry in isolated endothelial cells and in intact lungs (Jian et al. 2009 *Am J Respir Cell Mol Biol* 38: 386-92). Endothelial cells are responsible for forming the capillary vessels that mediate oxygen/carbon dioxide exchange, contributing to the septal barrier in the lung. Activation of TRPV4 channels results in contraction of endothelial cells in culture and cardiovascular collapse in vivo (Willette et al., 2008 *J Pharmacol Exp Ther* 325: 466-74), at least partially due to the enhanced filtration at the septal barrier resulting in lung edema and hemorrhage (Alvarez et al. 2006. *Circ Res* 99: 988-95). Indeed filtration at the septal barrier is increased in response to increased vascular and/or airway pressures and this response is dependent on the activity of TRPV4 channels (Jian et al. 2008 *Am J Respir Cell Mol Biol* 38: 386-92). Overall this suggests a clinical benefit of inhibiting TRPV4 function in the treatment of heart failure associated lung congestion.

Additional benefit is suggested in inhibiting TRPV4 function in pulmonary-based pathologies presenting with symptoms including lung edema/congestion, infection, inflammation, pulmonary remodeling and/or altered airway reactivity. A genetic link between TRPV4 and chronic obstructive pulmonary disorder (COPD) has recently been identified (Zhu et al., 2009. *Hum Mol Genetics*, in press) suggesting potential efficacy for TRPV4 modulation in treatment of COPD with or without coincident emphysema. Enhanced TRPV4 activity is also a key driver in ventilator-induced lung injury (Hamanaka et al., 2007. *Am J Physiol* 293: L923-32) and it is suggested that TRPV4 activation may underlie pathologies involved in acute respiratory distress syndrome (ARDS), pulmonary fibrosis and asthma (Liedtke & Simon, 2004. *Am J Physiol* 287: 269-71) A potential clinical benefit for TRPV4 blockers in the treatment of sinusitis, as well as allergic and non-allergic rhinitis is also supported (Bhargave et al., 2008. *Am J Rhinol* 22:7-12).

In addition, TRPV4 channels have recently been implicated in urinary bladder function (Thorneloe et al., 2008. *J Pharmacol Exp Ther* 326: 432-42) and are likely to provide therapeutic benefit for conditions of bladder overactivity, characterized by an increased urge to urinate and an enhancement of micturition frequency. These data suggest a clinically beneficial effect of inhibiting TRPV4, located on multiple cell types, on urinary bladder function that is likely to be effective in bladder disorders such as overactive bladder, interstitial cystitis and painful bladder syndrome.

Furthermore TRPV4 has in recent years been implicated in a number of other physiological/pathophysiological processes in which TRPV4 antagonists are likely to provide significant clinical benefit. These include various aspects of pain (Todaka et al. 2004. *J Biol Chem* 279: 35133-35138; Grant et al. 2007. *J Physiol* 578: 715-733; Alessandri-Haber et al. 2006. *J Neurosci* 26: 3864-3874), cardiovascular disease (Earley et al. 2005. *Circ Res* 97: 1270-9; Yang et al. 2006. *Am. J. Physiol.* 290:L1267-L1276), and bone related disorders; including osteoarthritis (Muramatsu et al. 2007. *J. Biol. Chem.* 282: 32158-67) genetic gain-of function mutations (Krakow et al., 2009. *Am J Hum Genet.* 84: 307-15; Rock et al., 2008 *Nat Genet.* 40: 999-1003) and osteoclast differentiation (Masuyama et al. 2008. *Cell Metab* 8: 257-65).

SUMMARY OF THE INVENTION

In one aspect this invention provides for diazabicyclo [2.2.1]hept-2-yl analogs, pharmaceutically acceptable salts thereof, and pharmaceutical compositions containing them.

In a second aspect, this invention provides for the use of the compounds of Formula (I) as TRPV4 antagonists.

In another aspect, this invention provides for the use of the compounds of Formula (I) for treating and preventing conditions associated with TRPV4 imbalance.

In yet another aspect, this invention provides for the use of the compounds of Formula (I) for the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, cardiovascular disease, renal dysfunction and osteoarthritis.

The TRPV4 antagonist may be administered alone or in conjunction with one or more other therapeutic agents, e.g. agents being selected from the group consisting of endothelin receptor antagonists, angiotensin converting enzyme (ACE) inhibitors, angiotension II receptor antagonists, vasopeptidase inhibitors, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, anti-histamines, Leukotriene antagonist, HMG-CoA reductase inhibitors, dual non-selective $\beta$-adrenoceptor and $\alpha_1$-adrenoceptor antagonists, type-5 phosphodiesterase inhibitors, and renin inhibitors.

Other aspects and advantages of the present invention are described further in the following detailed description of the preferred embodiments thereof.

DETAILED DESCRIPTION OF THE INVENTION

The present invention provides for compounds of Formula (I):

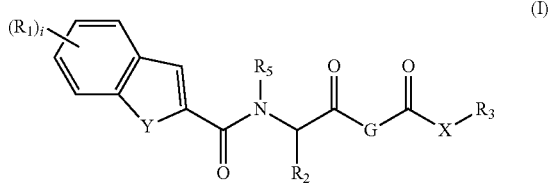

wherein:
$R_1$ is $C_{1-3}$ alkyl, $C_{1-3}$ alkoxy, $CF_3$, halo, $SO_2C_{1-3}$alkyl, $N(R_4)_2$, $OCF_3$, or CN;
$R_2$ is $C_{1-4}$ alkyl, —$CH_2C_{3-6}$cycloalkyl, or —$CH_2$-phenyl;
$R_3$ is

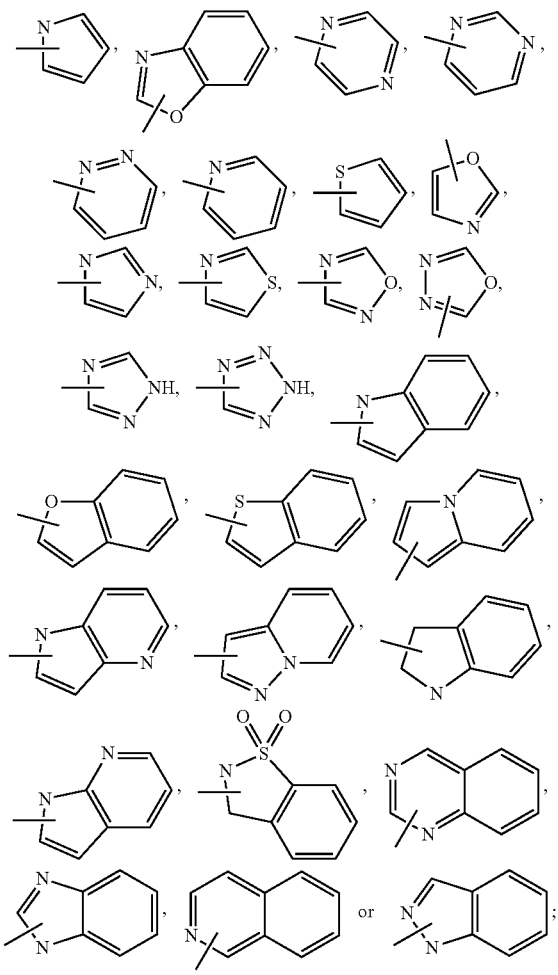

all of which may be unsubstituted or substituted with one, two, or three substituents selected from the group consisting of: $OC_{1-5}$alkyl, $C_{1-5}$alkyl, $OCF_3$, halo, $CF_3$, CN, $N(R_4)_2$, $C(O)NR_4C_{1-5}$alkyl, C(O)NHphenyl, $C(O)R_6$, $CO_2C_{1-3}$alkyl, $SO_2C_{1-3}$alkyl, $SO_2$-phenyl, $SO_2NR_4C_{1-5}$alkyl, —O-phenyl, phenyl, morpholinyl, pyrimidinyl, tetrahydropyranyl, pyridizinyl, oxazolyl, pyrazinyl, pyrrolyl, tetrazolyl, oxadiazolyl, triazolyl, dihydropyranyl, $C_{3-6}$ cycloalkyl, cyclohexenyl, piperazinyl, pyrrolidinyl, piperadinyl, and pyridyl;
wherein the $OC_{1-5}$alkyl, $C_{1-5}$alkyl, $C(O)NR_4C_{1-5}$alkyl, $SO_2NR_4C_{1-5}$alkyl, phenyl, morpholinyl, pyrimidinyl, dihydropyranyl, tetrahydropyranyl, pyridizinyl, pyrazinyl, oxazolyl, pyrollyl, $C_{3-6}$ cycloalkyl, cyclohexenyl, piperazinyl, pyrrolidinyl, piperadinyl, and pyridyl may be unsubstituted or substituted with one, two, or three substituents selected from the group consisting of: $OR_4$, $R_4$, $OCF_3$, halo, $CF_3$, CN, $N(R_4)_2$, morpholinyl, piperidinyl, pyrollidinyl, piperazinyl, tetrazolyl, $CO_2C_{1-4}$alkyl, $SO_2NHC_{1-3}$alkyl, $C(O)N(R_4)_2$, $NHSO_2C_{1-3}$alkyl and $SO_2C_{1-3}$alkyl;
G is

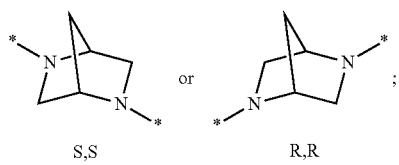

X is a bond or $CH_2$;
Y is $NR_4$ or S;
$R_4$ is independently H or $C_{1-3}$ alkyl;
$R_5$ is hydrogen or $C_{1-5}$ alkyl;
$R_6$ is

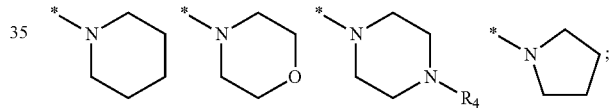

and
i is 0, 1, 2, or 3;
or a pharmaceutically acceptable salt thereof.

"Alkyl" refers to a monovalent saturated hydrocarbon chain having the specified number of member atoms. For example, $C_{1-4}$ alkyl refers to an alkyl group having from 1 to 4 member atoms. Alkyl groups may be straight or branched. Representative branched alkyl groups have one, two, or three branches. Alkyl includes methyl, ethyl, propyl (n-propyl and isopropyl), and butyl (n-butyl, isobutyl, and t-butyl).

"Cycloalkyl" refers to a monovalent saturated or unsaturated hydrocarbon ring having the specified number of member atoms. For example, $C_{3-6}$ cycloalkyl refers to a cycloalkyl group having from 3 to 6 member atoms. Unsaturated Cycloalkyl groups have one or more carbon-carbon double bonds within the ring. Cycloalkyl groups are not aromatic. Cycloalkyl includes cyclopropyl, cyclopropenyl, cyclobutyl, cyclobutenyl, cyclopentyl, cyclopentenyl, cyclohexyl, and cyclohexenyl.

"Alkoxy" as used herein refers to an —O—$C_{1-3}$ alkyl group wherein $C_{1-3}$ alkyl is as defined herein. Examples of such groups include methoxy, ethoxy, propoxy, and the like.

When used herein, the terms 'halogen' and 'halo' mean fluorine, chlorine, bromine and iodine, and fluoro, chloro, bromo, and iodo, respectively.

"Substituted" in reference to a group indicates that one or more hydrogen atom attached to a member atom within the group is replaced with a substituent selected from the group of defined substituents. It should be understood that the term "substituted" includes the implicit provision that such substitution be in accordance with the permitted valence of the substituted atom and the substituent and that the substitution results in a stable compound (i.e. one that does not spontaneously undergo transformation such as by rearrangement, cyclization, or elimination and that is sufficiently robust to survive isolation from a reaction mixture). When it is stated that a group may contain one or more substituents, one or more (as appropriate) member atoms within the group may be substituted. In addition, a single member atom within the group may be substituted with more than one substituent as long as such substitution is in accordance with the permitted valence of the atom. Suitable substituents are defined herein for each substituted or optionally substituted group.

With regard to stereoisomers, the compounds of Formula (I) may have one or more asymmetric carbon atom and may occur as racemates, racemic mixtures and as individual enantiomers or diastereomers. All such isomeric forms are included within the present invention, including mixtures thereof.

As used herein, "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compounds according to Formula (I) may be prepared. These pharmaceutically acceptable salts may be prepared in situ during the final isolation and purification of the compound, or by separately treating the purified compound in its free acid or free base form with a suitable base or acid, respectively.

In certain embodiments, compounds according to Formula (I) may contain an acidic functional group and are, therefore, capable of forming pharmaceutically acceptable base addition salts by treatment with a suitable base. Examples of such bases include a) hydroxides, carbonates, and bicarbonates of sodium, potassium, lithium, calcium, magnesium, aluminium, and zinc; and b) primary, secondary, and tertiary amines including aliphatic amines, aromatic amines, aliphatic diamines, and hydroxy alkylamines such as methylamine, ethylamine, 2-hydroxy ethylamine, diethylamine, triethylamine, ethylenediamine, ethanolamine, diethanolamine, and cyclohexylamine.

In certain embodiments, compounds according to Formula (I) may contain a basic functional group and are therefore capable of forming pharmaceutically acceptable acid addition salts by treatment with a suitable acid. Suitable acids include pharmaceutically acceptable inorganic acids and organic acids. Representative pharmaceutically acceptable acids include hydrogen chloride, hydrogen bromide, nitric acid, sulfuric acid, sulfonic acid, phosphoric acid, acetic acid, hydroxyacetic acid, phenylacetic acid, propionic acid, butyric acid, valeric acid, maleic acid, acrylic acid, fumaric acid, malic acid, malonic acid, tartaric acid, citric acid, salicylic acid, benzoic acid, tannic acid, formic acid, stearic acid, lactic acid, ascorbic acid, methylsulfonic acid, p-toluenesulfonic acid, oleic acid, lauric acid, and the like.

As used herein, the term "a compound of Formula (I)" or "the compound of Formula (I)" refers to one or more compounds according to Formula (I). The compound of Formula (I) may exist in solid or liquid form. In the solid state, it may exist in crystalline or noncrystalline form, or as a mixture thereof. The skilled artisan will appreciate that pharmaceutically acceptable solvates may be formed for crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water. The invention includes all such solvates.

The skilled artisan will further appreciate that certain compounds of the invention that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as 2H, 3H, 11C, 13C, 14C, 15N, 17O, 18O, 31P, 32P, 35S, 18F, 36Cl, 123I and 125I.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as 3H, 14C are incorporated, are useful in drug and/or substrate tissue distribution assays. Tritiated, i.e., 3H, and carbon-14, i.e., 14C, isotopes are particularly preferred for their ease of preparation and detectability. 11C and 18F isotopes are particularly useful in PET (positron emission tomography), and 125I isotopes are particularly useful in SPECT (single photon emission computerized tomography), all useful in brain imaging. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Representative Embodiments

In one embodiment:
$R_1$ is $C_{1-3}$ alkyl, $C_{1-3}$ alkoxy, $CF_3$, halo, $SO_2C_{1-3}$alkyl, $N(R_4)_2$, $OCF_3$, or CN;
$R_2$ is $C_{1-4}$ alkyl, —$CH_2C_{3-6}$cycloalkyl, or —$CH_2$-phenyl;
$R_3$ is

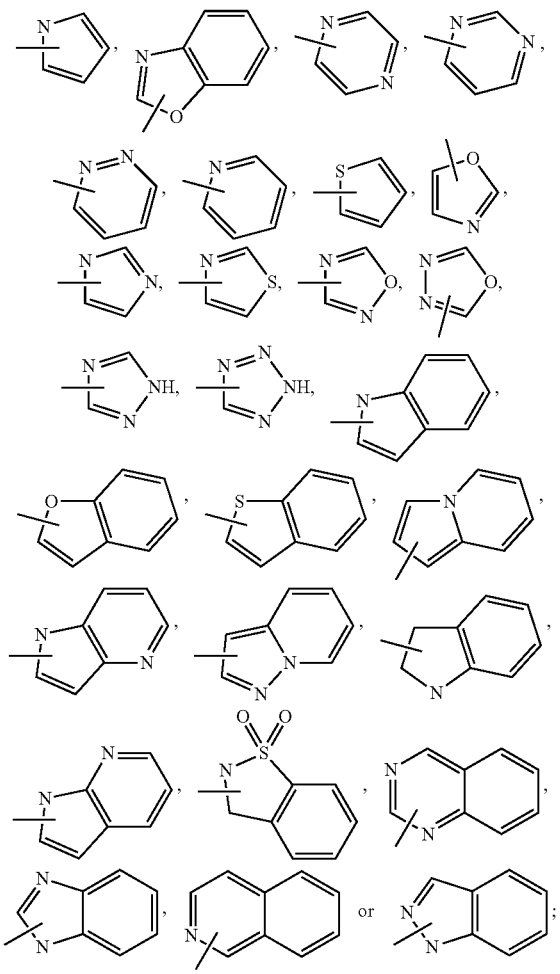

all of which may be unsubstituted or substituted with one, two, or three substituents selected from the group consisting of: $OC_{1-5}$alkyl, $C_{1-5}$alkyl, $OCF_3$, halo, $CF_3$, CN, $N(R_4)_2$, $C(O)NR_4C_{1-5}$alkyl, C(O)NHphenyl, $C(O)R_6$, $CO_2C_{1-3}$alkyl, $SO_2C_{1-3}$alkyl, $SO_2$phenyl, $SO_2NR_4C_{1-5}$alkyl, —O-phenyl, phenyl, morpholinyl, pyrimidinyl, tetrahydropyranyl, pyridizinyl, oxazolyl, pyrazinyl, pyrrolyl, tetrazolyl, oxadiazolyl, triazolyl, dihydropyranyl, $C_{3-6}$ cycloalkyl, cyclohexenyl, piperazinyl, pyrrolidinyl, piperadinyl, and pyridyl;
wherein the $OC_{1-5}$alkyl, $C_{1-5}$alkyl, $C(O)NR_4C_{1-5}$alkyl, $SO_2NR_4C_{1-5}$alkyl, phenyl, morpholinyl, pyrimidinyl, dihydropyranyl, tetrahydropyranyl, pyridizinyl, pyrazinyl, oxazolyl, pyrollyl, $C_{3-6}$cycloalkyl, cyclohexenyl, piperazinyl, pyrrolidinyl, piperadinyl, and pyridyl may be unsubstituted or substituted with one, two, or three substituents selected from the group consisting of: $OR_4$, $R_4$, $OCF_3$, halo, $CF_3$, CN, $N(R_4)_2$, morpholinyl, piperidinyl, pyrollidinyl, piperazinyl, tetrazolyl, $CO_2C_{1-4}$alkyl, $SO_2NHC_{1-3}$alkyl, $C(O)N(R_4)_2$, $NHSO_2C_{1-3}$alkyl and $SO_2C_{1-3}$alkyl;

G is

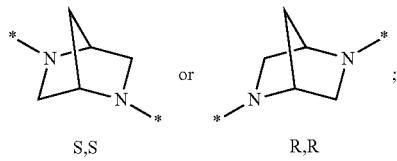

X is a bond or $CH_2$;
Y is $NR_4$ or S;
$R_4$ is independently H or $C_{1-3}$ alkyl;
$R_5$ is hydrogen or $C_{1-5}$ alkyl;
$R_6$ is

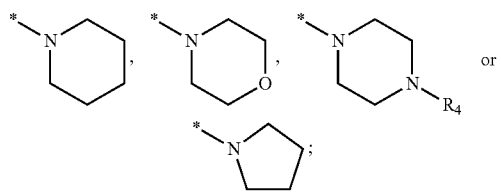

and
i is 0, 1, 2, or 3.
In another embodiment:
$R_1$ is $C_{1-3}$ alkyl, $C_{1-3}$ alkoxy, $CF_3$, halo, $OCF_3$, or CN;
$R_2$ is $C_{1-4}$ alkyl, —$CH_2C_{3-6}$cycloalkyl, or —$CH_2$-phenyl;
$R_3$ is:

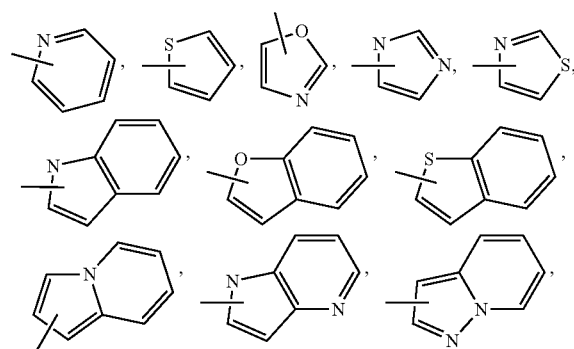
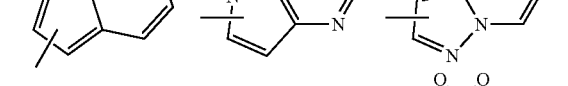
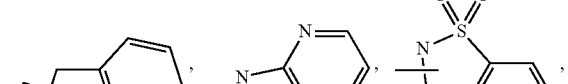
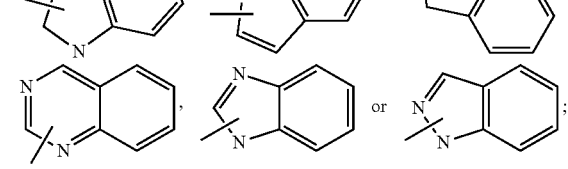
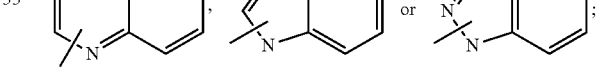

all of which may be unsubstituted or substituted with one, two, or three substituents selected from the group consisting of: $OR_4$, $R_4$, $OCF_3$, halo, $CF_3$, CN, $N(R_4)_2$, $CO_2C_{1-3}$alkyl, $SO_2C_{1-3}$alkyl, $SO_2$phenyl, phenyl and pyridyl;
wherein the phenyl or pyridyl may be unsubstituted or substituted with one, two, or three substituents selected from thegroup consisting of: $OR_4$, $R_4$, $OCF_3$, halo, $CF_3$, CN, $N(R_4)_2$, CO$_2$C$_{1-3}$alkyl, and
SO$_2$C$_{1-3}$alkyl;
G is

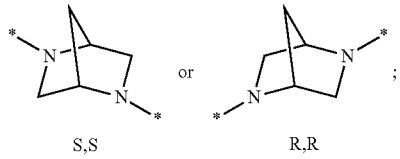

X is a bond or CH$_2$;
Y is NR$_4$ or S;
R$_4$ is H or C$_{1-3}$ alkyl;
R$_5$ is hydrogen; and
i is 0, 1, 2, or 3.
In another embodiment:
R$_1$ is CF$_3$, halo, OCF$_3$, or CN;
R$_2$ is C$_{1-4}$ alkyl;
R$_3$ is:

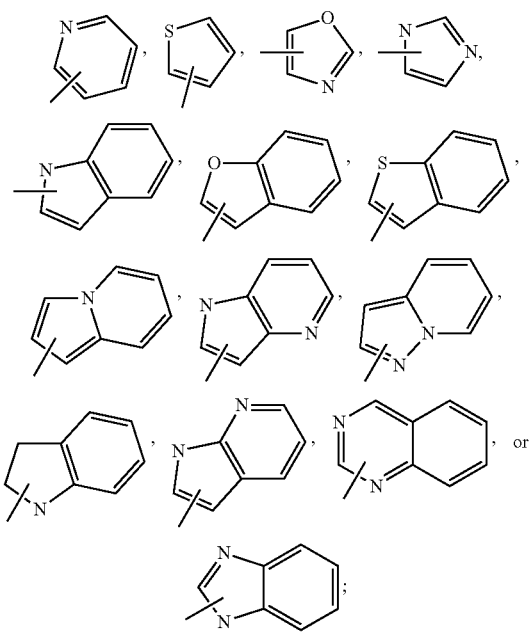

all of which may be unsubstituted or substituted with one, two, or three substituents selected from the group consisting of: OR$_4$, R$_4$, OCF$_3$, halo, CF$_3$, CN, N(R$_4$)$_2$, CO$_2$C$_{1-3}$alkyl, SO$_2$C$_{1-3}$alkyl, SO$_2$phenyl, —O-phenyl, phenyl, morpholinyl, pyrimidinyl, dihydropyranyl, C$_{3-6}$ cycloalkyl, cyclohexenyl, piperazinyl, pyrrolidinyl, piperadinyl, and pyridyl;
wherein the phenyl, morpholinyl, pyrimidinyl, dihydropyranyl, C$_{3-6}$ cycloalkyl, cyclohexenyl, piperazinyl, pyrrolidinyl, piperadinyl, and pyridyl may be unsubstituted or substituted with one, two, or three substituents selected from the group consisting of: OR$_4$, R$_4$, OCF$_3$, halo, CF$_3$, CN, N(R$_4$)$_2$, CO$_2$C$_{1-3}$alkyl, and SO$_2$C$_{1-3}$alkyl;

G is

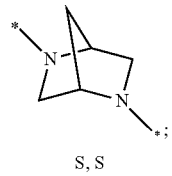

X is a bond;
Y is NR$_4$ or S;
R$_4$ is C$_{1-3}$ alkyl;
R$_5$ is hydrogen; and
i is 0, 1, or 2.
In another embodiment:
R$_1$ is CF$_3$, halo, OCF$_3$, or CN;
R$_2$ is C$_{1-4}$ alkyl;
R$_3$ is:

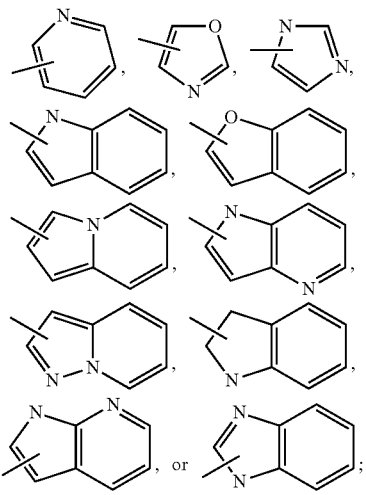

all of which may be unsubstituted or substituted with one, two, or three substituents selected from the group consisting of: OR$_4$, R$_4$, OCF$_3$, halo, CF$_3$, CN, N(R$_4$)$_2$, CO$_2$C$_{1-3}$alkyl, SO$_2$C$_{1-3}$alkyl, SO$_2$phenyl, —O-phenyl, phenyl, and pyridyl;
wherein the phenyl and pyridyl may be unsubstituted or substituted with one, two, or three substituents selected from the group consisting of: OR$_4$, R$_4$, OCF$_3$, halo, CF$_3$, CN, N(R$_4$)$_2$, CO$_2$C$_{1-3}$alkyl, and SO$_2$C$_{1-3}$alkyl;
G is

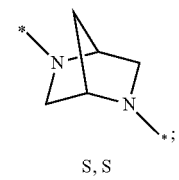

X is a bond;
Y is NR$_4$ or S;
R$_4$ is C$_{1-3}$ alkyl;
R$_5$ is hydrogen or C$_{1-3}$ alkyl; and
i is 0, 1, or 2.

In another embodiment:

$R_1$ is $C_{1-3}$ alkyl, $C_{1-3}$ alkoxy, $CF_3$, halo, $SO_2C_{1-3}$alkyl, $N(R_4)_2$, $OCF_3$, or CN;

$R_2$ is $C_{1-4}$ alkyl, —$CH_2C_{3-6}$cycloalkyl, or —$CH_2$-phenyl;

$R_3$ is

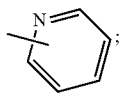

which may be unsubstituted or substituted with one, two, or three substituents selected from the group consisting of: $OC_{1-5}$ alkyl, $C_{1-5}$alkyl, $OCF_3$, halo, $CF_3$, CN, $N(R_4)_2$, $C(O)NR_4C_{1-5}$ alkyl, $C(O)NH$phenyl, $C(O)R_6$, $CO_2C_{1-3}$alkyl, $SO_2C_{1-3}$ alkyl, $SO_2$phenyl, $SO_2NR_4C_{1-5}$alkyl, —O-phenyl, phenyl, morpholinyl, pyrimidinyl, tetrahydropyranyl, pyridizinyl, oxazolyl, pyrazinyl, pyrrolyl, tetrazolyl, oxadiazolyl, triazolyl, dihydropyranyl, $C_{3-6}$ cycloalkyl, cyclohexenyl, piperazinyl, pyrrolidinyl, piperadinyl, and pyridyl;

wherein the $OC_{1-5}$alkyl, $C_{1-5}$alkyl, $C(O)NR_4C_{1-5}$alkyl, $SO_2NR_4C_{1-5}$alkyl, phenyl, morpholinyl, pyrimidinyl, dihydropyranyl, tetrahydropyranyl, pyridizinyl, pyrazinyl, oxazolyl, pyrollyl, $C_{3-6}$ cycloalkyl, cyclohexenyl, piperazinyl, pyrrolidinyl, piperadinyl, and pyridyl may be unsubstituted or substituted with one, two, or three substituents selected from the group consisting of: $OR_4$, $R_4$, $OCF_3$, halo, $CF_3$, CN, $N(R_4)_2$, morpholinyl, piperidinyl, pyrollidinyl, piperazinyl, tetrazolyl, $CO_2C_{1-4}$alkyl, $SO_2NHC_{1-3}$alkyl, $C(O)N(R_4)_2$, $NHSO_2C_{1-3}$alkyl and $SO_2C_{1-3}$alkyl;

G is

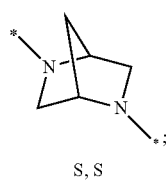

X is a bond or $CH_2$;

Y is $NR_4$ or S;

$R_4$ is independently H or $C_{1-3}$ alkyl;

$R_5$ is hydrogen or $C_{1-5}$ alkyl;

$R_6$ is

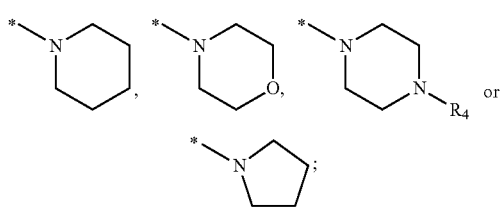

and i is 0, 1, 2, or 3.

In another embodiment:

$R_1$ is $C_{1-3}$ alkyl, $C_{1-3}$ alkoxy, $CF_3$, halo, or CN;

$R_2$ is $C_{1-4}$ alkyl;

$R_3$ is

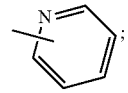

which may be unsubstituted or substituted with one, two, or three substituents selected from the group consisting of: $OC_{1-5}$ alkyl, $C_{1-5}$alkyl, $OCF_3$, halo, $CF_3$, CN, $N(R_4)_2$, $C(O)NR_4C_{1-5}$ alkyl, $C(O)NH$phenyl, $C(O)R_6$, $CO_2C_{1-3}$alkyl, $SO_2C_{1-3}$ alkyl, $SO_2$phenyl, $SO_2NR_4C_{1-5}$alkyl, —O-phenyl, phenyl, morpholinyl, pyrimidinyl, tetrahydropyranyl, pyridizinyl, oxazolyl, pyrazinyl, pyrrolyl, tetrazolyl, oxadiazolyl, triazolyl, dihydropyranyl, $C_{3-6}$ cycloalkyl, cyclohexenyl, piperazinyl, pyrrolidinyl, piperadinyl, and pyridyl;

wherein the phenyl, morpholinyl, pyrimidinyl, dihydropyranyl, tetrahydropyranyl, $C_{3-6}$cycloalkyl, piperazinyl, pyrrolidinyl, piperadinyl, and pyridyl may be unsubstituted or substituted with one, two, or three substituents selected from the group consisting of: $OR_4$, $R_4$, $OCF_3$, halo, $CF_3$, CN, $N(R_4)_2$, morpholinyl, piperidinyl, pyrollidinyl, piperazinyl, tetrazolyl, $CO_2C_{1-4}$alkyl, $SO_2NHC_{1-3}$alkyl, $C(O)N(R_4)_2$, $NHSO_2C_{1-3}$alkyl and $SO_2C_{1-3}$alkyl;

G is

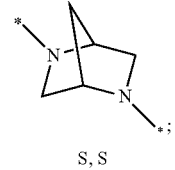

X is a bond;

Y is $NR_4$ or S;

$R_4$ is independently H or $C_{1-3}$ alkyl;

$R_5$ is hydrogen or $C_{1-5}$ alkyl;

$R_6$ is

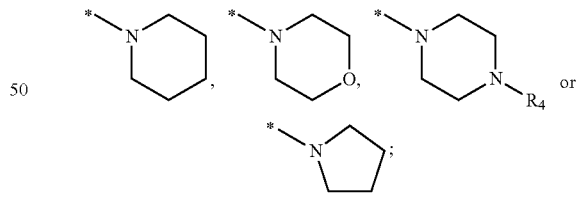

and i is 0, 1, 2, or 3.

It is to be understood that the present invention covers all combinations of particular groups described hereinabove.

Specific examples of compounds of the present invention include the following:

N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(5-phenyl-2-thienyl)carbonyl]-2,5-diazabicyclo[2.2.1]hept-2-yl}carbonyl)propyl]-1H-indole-2-carboxamide;

N-[(1S)-1-({(1S,4S)-5-[(2R)-2,3-dihydro-1H-indol-2-ylcarbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;

N-((1S)-1-{[(1S,4S)-5-(1H-indazol-3-ylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(1H-indol-7-ylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(1H-indol-6-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(7-methyl-1H-indol-2-yl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[5-(methyloxy)-1H-indol-2-yl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide;

N-[(1S)-1-({(1S,4S)-5-[(5-fluoro-1H-indol-2-yl)carbonyl]-2,5-diazabicyclo[2.2.1]hept-2-yl}carbonyl)-2,2-dimethylpropyl]-1H-indole-2-carboxamide;

N-((1S)-1-{[(1S,4S)-5-(1H-indol-4-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(1-methyl-1H-indol-2-yl)carbonyl]-2,5-diazabicyclo[2.2.1]hept-2-yl}carbonyl)propyl]-1H-indole-2-carboxamide;

N-((1S)-1-{[(1S,4S)-5-(1H-indol-3-ylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(1H-indol-5-ylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(1-benzothien-2-ylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;

N-((1S)-1-{[(1S,4S)-5-(1-benzofuran-2-ylcarbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide;

N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[4-(methyloxy)-1H-indol-2-yl]carbonyl}-2,5-diazabicyclo[2.2.1]hept-2-yl)carbonyl]propyl}-1H-indole-2-carboxamide;

N-[(1S)-1-({[(1S,4S)-5-[(4-fluoro-1H-indol-2-yl)carbonyl]-2,5-diazabicyclo[2.2.1]hept-2-yl]carbonyl}-2,2-dimethylpropyl]-1H-indole-2-carboxamide;

N-[(1S)-1-({(1S,4S)-5-[(1,1-dioxido-1,2-benzisothiazol-2(3H)-yl)acetyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[1-(phenylsulfonyl)-1H-indol-2-yl]carbonyl}-2,5-diazabicyclo[2.2.1]hept-2-yl)carbonyl]propyl}-1H-indole-2-carboxamide;

N-[(1S)-1-({(1S,4S)-5-[(5-chloro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(4,5-dimethyl-2-thienyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(2,6-dichloro-3-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(4-chloro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-2,2-dimethyl-1-({(1S,4S)-5-[(4-methyl-1H-indol-2-yl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(5-phenyl-1,3-oxazol-4-yl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(2-phenyl-1,3-oxazol-4-yl)carbonyl]-2,5-diazabicyclo[2.2.1]hept-2-yl}carbonyl)propyl]-1H-indole-2-carboxamide;

N-((1S)-2,2-dimethyl-1-{[(1S,4S)-5-(1H-pyrrolo[3,2-b]pyridin-2-ylcarbonyl)-2,5-diazabicyclo[2.2.1]hept-2-yl]carbonyl}propyl)-1H-indole-2-carboxamide;

N-((1S)-2,2-dimethyl-1-{[(1S,4S)-5-(pyrazolo[1,5-a]pyridin-2-ylcarbonyl)-2,5-diazabicyclo[2.2.1]hept-2-yl]carbonyl}propyl)-1H-indole-2-carboxamide;

Methyl 2-({(1S,4S)-5-[N-(1H-indol-2-ylcarbonyl)-3-methyl-L-valyl]-2,5-diazabicyclo[2.2.1]hept-2-yl}carbonyl)-1H-indole-5-carboxylate;

N-((1S)-1-{[(1S,4S)-5-(1-benzothien-2-ylacetyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(methyloxy)-1H-benzimidazol-2-yl]carbonyl}-2,5-diazabicyclo[2.2.1]hept-2-yl)carbonyl]propyl}-1H-indole-2-carboxamide;

N-((1S)-2,2-dimethyl-1-{[(1S,4S)-5-(1H-pyrrolo[2,3-b]pyridin-2-ylcarbonyl)-2,5-diazabicyclo[2.2.1]hept-2-yl]carbonyl}propyl)-1H-indole-2-carboxamide;

N-((1S)-2,2-dimethyl-1-{[(1S,4S)-5-({5-methyl-2-[4-(methyloxy)phenyl]-1,3-oxazol-4-yl}carbonyl)-2,5-diazabicyclo[2.2.1]hept-2-yl]carbonyl}propyl)-1H-indole-2-carboxamide;

N-{(1S)-1-[((1S,4S)-5-{[6-(dimethylamino)-1H-indol-2-yl]carbonyl}-2,5-diazabicyclo[2.2.1]hept-2-yl)carbonyl]-2,2-dimethylpropyl}-1H-indole-2-carboxamide;

N-[(1S)-2,2-dimethyl-1-({(1S,4S)-5-[(2-phenyl-1H-imidazol-4-yl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[2-phenyl-5-(trifluoromethyl)-1,3-oxazol-4-yl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[4-(4-morpholinyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[6-(1-pyrrolidinyl)-2-pyridinyl]carbonyl}-2,5-diazabicyclo[2.2.1]hept-2-yl)carbonyl]propyl}-1H-indole-2-carboxamide;

N-((1S)-2,2-dimethyl-1-{[(1S,4S)-5-({5-[(phenylamino)carbonyl]-2-pyridinyl}carbonyl)-2,5-diazabicyclo[2.2.1]hept-2-yl]carbonyl}propyl)-1H-indole-2-carboxamide;

N-((1S)-1-{[(1S,4S)-5-(3-isoquinolinylcarbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(1-pyrrolidinylcarbonyl)-2-pyridinyl]carbonyl}-2,5-diazabicyclo[2.2.1]hept-2-yl)carbonyl]propyl}-1H-indole-2-carboxamide;

N-((1S)-2,2-dimethyl-1-{[(1S,4S)-5-(1,3-thiazol-4-ylcarbonyl)-2,5-diazabicyclo[2.2.1]hept-2-yl]carbonyl}propyl)-1H-indole-2-carboxamide;

N-((1S)-2,2-dimethyl-1-{[(1S,4S)-5-(1,3-thiazol-5-ylcarbonyl)-2,5-diazabicyclo[2.2.1]hept-2-yl]carbonyl}propyl)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[5-(4-pyridinyl)-1H-indol-2-yl]carbonyl}-2,5-diazabicyclo[2.2.1]hept-2-yl)carbonyl]propyl}-1H-indole-2-carboxamide;

N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide;

6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxamide;

methyl 6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxylate;

N-{(1S)-2,2-dimethyl-1-[((1S,4S)-5-{[5-(1H-tetrazol-5-yl)-2,3'-bipyridin-6'-yl]carbonyl}-2,5-diazabicyclo[2.2.1]hept-2-yl)carbonyl]propyl}-1H-indole-2-carboxamide;

N-{(1S)-1-[((1S,4S)-5-{[5-(4-cyanophenyl)-2-pyridinyl]carbonyl}-2,5-diazabicyclo[2.2.1]hept-2-yl)carbonyl]-2,2-dimethylpropyl}-1H-indole-2-carboxamide;

N-methyl-N-[(1S)-2-methyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;

N-methyl-N-[(1S)-3-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide;

N-methyl-N-((1S)-1-methyl-2-oxo-2-{(1S,4S)-5-[(5-phenyl-2-pyridinyl)carbonyl]-2,5-diazabicyclo[2.2.1]hept-2-yl}ethyl)-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-ethyl-1H-indole-2-carboxamide;

N-{(1S)-2,2-dimethyl-1-[(1S,4S)-5-{[5-(1-pyrrolidinyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(1-hydroxycyclohexyl)-2-pyridinyl]carbonyl}-2,5-diazabicyclo[2.2.1]hept-2-yl)carbonyl]-2,2-dimethylpropyl}-1H-indole-2-carboxamide;

N-{(1S)-2,2-dimethyl-1-[((1S,4S)-5-{[5-(4-morpholinyl)-2-pyridinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(5-phenyl-2-pyrazinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(5-phenyl-1,3-oxazol-2-yl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[6-(4-morpholinyl)-1H-indol-2-yl]carbonyl}-2,5-diazabicyclo[2.2.1]hept-2-yl)carbonyl]propyl}-1H-indole-2-carboxamide;

N-[(1S)-1-({(1S,4S)-5-[(6-amino-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-ethyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclopentyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(1-methylethyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(2-methylpropyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(phenyloxy)-2-pyridinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(4-phenyl-1H-pyrrol-2-yl)carbonyl]-2,5-diazabicyclo[2.2.1]hept-2-yl]carbonyl)propyl]-1H-indole-2-carboxamide;

N-((1S)-1-{[(1S,4S)-5-(3,3'-bipyridin-6-ylcarbonyl)-2,5-diazabicyclo[2.2.1]hept-2-yl]carbonyl}-2,2-dimethylpropyl)-1H-indole-2-carboxamide;

N-{(1S)-1-[((1S,4S)-5-{[5-(2,6-dimethyl-4-morpholinyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-2,2-dimethyl-1-({(1S,4S)-5-[(6-methyl-5-phenyl-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(4-methyl-5-phenyl-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(3-methyl-5-phenyl-2-pyridinyl)carbonyl]-2,5-diazabicyclo[2.2.1]hept-2-yl}carbonyl)propyl]-1H-indole-2-carboxamide;

N-((1S,2S)-2-methyl-1-{[(1S,4S)-5-({5-[2-(methyloxy)phenyl]-2-pyrimidinyl}carbonyl)-2,5-diazabicyclo[2.2.1]hept-2-yl]carbonyl}butyl)-1H-indole-2-carboxamide;

N-{(1S,2S)-1-[((1S,4S)-5-{[5-(2-fluorophenyl)-2-pyrimidinyl]carbonyl}-2,5-diazabicyclo[2.2.1]hept-2-yl)carbonyl]-2-methylbutyl}-1H-indole-2-carboxamide;

N-[(1S,2S)-2-methyl-1-({(1S,4S)-5-[(5-phenyl-2-pyrimidinyl)carbonyl]-2,5-diazabicyclo[2.2.1]hept-2-yl}carbonyl)butyl]-1H-indole-2-carboxamide;

N-((1S)-2,2-dimethyl-1-{[(1S,4S)-5-({5-[2-(methyloxy)phenyl]-2-pyrimidinyl}carbonyl)-2,5-diazabicyclo[2.2.1]hept-2-yl]carbonyl}propyl)-1H-indole-2-carboxamide;

N-{(1S)-1-[((1S,4S)-5-{[5-(2-fluorophenyl)-2-pyrimidinyl]carbonyl}-2,5-diazabicyclo[2.2.1]hept-2-yl)carbonyl]-2,2-dimethylpropyl}-1H-indole-2-carboxamide;

N-{(1S)-2,2-dimethyl-1-[((1S,4S)-5-{[5-(1-piperidinyl)-2-pyrimidinyl]carbonyl}-2,5-diazabicyclo[2.2.1]hept-2-yl)carbonyl]propyl}-1H-indole-2-carboxamide;

N-((1S)-1-{[(1S,4S)-5-({5-[4-(1-hydroxy-1-methylethyl)phenyl]-2-pyridinyl}carbonyl)-2,5-diazabicyclo[2.2.1]hept-2-yl]carbonyl}-2,2-dimethylpropyl)-1H-indole-2-carboxamide;

N-((1S)-1-{[(1S,4S)-5-({5-[4-(1,1-dimethylethyl)-1-piperazinyl]-2-pyridinyl}carbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(4-methyl-1-piperazinyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(4-ethyl-1-piperazinyl)-2-pyridinyl]carbonyl}-2,5-diazabicyclo[2.2.1]hept-2-yl)carbonyl]-2,2-dimethylpropyl}-1H-indole-2-carboxamide;

N-((1S)-2,2-dimethyl-1-{[(1S,4S)-5-({5-[4-(methylsulfonyl)-1-piperazinyl]-2-pyridinyl}carbonyl)-2,5-diazabicyclo[2.2.1]hept-2-yl]carbonyl}propyl)-1H-indole-2-carboxamide;

N-{(1S)-2,2-dimethyl-1-[((1S,4S)-5-{[5-(1-piperidinyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(2-pyrimidinyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(3,6-dihydro-2H-pyran-4-yl)-2-pyridinyl]carbonyl}-2,5-diazabicyclo[2.2.1]hept-2-yl)carbonyl]-2,2-dimethylpropyl}-1H-indole-2-carboxamide;

N-{(1S)-1-[((1S,4S)-5-{[5-(1-cyclohexen-1-yl)-2-pyridinyl]carbonyl}-2,5-diazabicyclo[2.2.1]hept-2-yl)carbonyl]-2,2-dimethylpropyl}-1H-indole-2-carboxamide;

7-fluoro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-7-fluoro-1H-indole-2-carboxamide;

7-fluoro-N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;

7-fluoro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(2S)-2,3-dihydro-1H-indol-2-ylcarbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-butyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(trifluoromethyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[2-(4-chlorophenyl)-5-methyl-1,3-oxazol-4-yl]carbonyl}-2,5-diazabicyclo[2.2.1]hept-2-yl)carbonyl]-2,2-dimethylpropyl}-1H-indole-2-carboxamide;

N-((1S)-1-{[(1S,4S)-5-(1,3-benzoxazol-2-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(5-phenyl-1H-pyrrol-2-yl)carbonyl]-2,5-diazabicyclo[2.2.1]hept-2-yl}carbonyl)propyl]-1H-indole-2-carboxamide;

N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide;

N-[(1S)-2,2-dimethyl-1-({(1R,4R)-5-[(5-phenyl-2-pyridinyl)carbonyl]-2,5-diazabicyclo[2.2.1]hept-2-yl}carbonyl)propyl]-1H-indole-2-carboxamide;

N-((1S)-1-{[(1S,4S)-5-(3-biphenylylcarbonyl)-2,5-diazabicyclo[2.2.1]hept-2-yl]carbonyl}-2,2-dimethylpropyl)-1H-indole-2-carboxamide;

N-[(1S)-1-({(1S,4S)-5-[(4-chloro-3-biphenylyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[1-(2-pyridinyl)-4-piperidinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(1-phenyl-1H-imidazol-4-yl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-7-fluoro-1H-indole-2-carboxamide;

N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-7-fluoro-1H-indole-2-carboxamide;

N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-7-fluoro-1H-indole-2-carboxamide;

N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-7-fluoro-1H-indole-2-carboxamide;

7-fluoro-N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide;

6-chloro-N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide;

6-chloro-N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;

6-chloro-N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide;

6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;

6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-methyl-1H-indole-2-carboxamide;

N-((1R)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2-methylpropyl]-1H-indole-2-carboxamide;

N-[(1S)-2-{(1S,4S)-5-[(5-cyclohexyl-2-pyridinyl)carbonyl]-2,5-diazabicyclo[2.2.1]hept-2-yl}-2-oxo-1-(phenylmethyl)ethyl]-1H-indole-2-carboxamide;

N-[(1S,2S)-1-({(1S,4S)-5-[(5-cyclohexyl-2-pyridinyl)carbonyl]-2,5-diazabicyclo[2.2.1]hept-2-yl}carbonyl)-2-methylbutyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-methyl-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-5-fluoro-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-5-fluoro-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-7-fluoro-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-7-fluoro-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,7-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-dichloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,7-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-7-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(ethyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-fluoro-1H-indole-2-carboxamide;

N-methyl-N-[(1S,2S)-2-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1-methyl-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-[(trifluoromethyl)oxy]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-4-methyl-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-hydroxy-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-hydroxy-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-6-methyl-1H-indole-2-carboxamide;

6-chloro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

6-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

5-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl]carbonyl)propyl}-6-methyl-1H-indole-2-carboxamide;

6-chloro-N-[(1S)-2,2-dimethyl-1-({(1S,4S)-5-[(5-phenyl-2-pyridinyl)carbonyl]-2,5-diazabicyclo[2.2.1]hept-2-yl]carbonyl)propyl}-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-fluoro-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl]carbonyl)propyl}-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-N-methyl-1H-indole-2-carboxamide;

N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl}-N-methyl-1H-indole-2-carboxamide;

N-[(1S)-2,2-dimethyl-1-({(1S,4S)-5-[(1-phenyl-1H-imidazol-4-yl)carbonyl]-2,5-diazabicyclo[2.2.1]hept-2-yl]carbonyl)propyl}-N-methyl-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-methyl-1H-indole-2-carboxamide;

N-((1S)-1-{[(1S,4S)-5-({5-[4-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide;

2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic;

4-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic;

N-((1S)-1-{[(1S,4S)-5-({5-[2-(ethyloxy)phenyl]-2-pyridinyl}carbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(2-methylphenyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(2-chlorophenyl)-2-pyridinyl]carbonyl}-2,5-diazabicyclo[2.2.1]hept-2-yl)carbonyl]-2,2-dimethylpropyl}-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

N-((1S)-2,2-dimethyl-1-{[(1S,4S)-5-({5-[2-(methyloxy)phenyl]-2-pyridinyl}carbonyl)-2,5-diazabicyclo[2.2.1]hept-2-yl]carbonyl}propyl)-1H-indole-2-carboxamide;

N-{(1S)-1-[((1S,4S)-5-{[5-(3-cyanophenyl)-2-pyridinyl]carbonyl}-2,5-diazabicyclo[2.2.1]hept-2-yl)carbonyl]-2,2-dimethylpropyl}-1H-indole-2-carboxamide;

N-((1S)-1-{[(1S,4S)-5-({5-[3-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide;

N-((1S)-2,2-dimethyl-1-{[(1S,4S)-5-({5-[4-(methylsulfonyl)phenyl]-2-pyridinyl}carbonyl)-2,5-diazabicyclo[2.2.1]hept-2-yl]carbonyl}propyl)-1H-indole-2-carboxamide;

N-[(1S)-2,2-dimethyl-1-({(1S,4S)-5-[(5-{2-[(trifluoromethyl)oxy]phenyl}-2-pyridinyl)carbonyl]-2,5-diazabicyclo[2.2.1]hept-2-yl]carbonyl)propyl}-1H-indole-2-carboxamide;

N-[(1S)-2,2-dimethyl-1-({(1S,4S)-5-[(5-{4-[(trifluoromethyl)oxy]phenyl}-2-pyridinyl)carbonyl]-2,5-diazabicyclo[2.2.1]hept-2-yl}carbonyl)propyl}-1H-indole-2-carboxamide;

N-[(1S)-2,2-dimethyl-1-({(1S,4S)-5-[(5-{3-[(trifluoromethyl)oxy]phenyl}-2-pyridinyl)carbonyl]-2,5-diazabicyclo[2.2.1]hept-2-yl}carbonyl)propyl}-1H-indole-2-carboxamide;

N-[(1S)-1-({(1S,4S)-5-[(6'-cyano-3,3'-bipyridin-6-yl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(1H-pyrrol-2-yl)-2-pyridinyl]carbonyl}-2,5-diazabicyclo[2.2.1]hept-2-yl)carbonyl]propyl}-1H-indole-2-carboxamide;

1,1-dimethylethyl 2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]-1H-pyrrole-1-carboxylate;

N-{(1S)-1-[((1S,4S)-5-{[5-(3,5-dimethyl-4-isoxazolyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-1-({(1S,4S)-5-[(6-chloro-2,2':6',3''-terpyridin-6''-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(6-chloro-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-fluoro-6-methyl-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(3-fluoro-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-2,2-dimethyl-1-({(1S,4S)-5-[(3-methyl-2,3'-bipyridin-6'-yl)carbonyl]-2,5-diazabicyclo[2.2.1]hept-2-yl}carbonyl)propyl]-1H-indole-2-carboxamide;

N-[(1S)-1-({(1S,4S)-5-[(3-chloro-2,3'-bipyridin-6'-yl)carbonyl]-2,5-diazabicyclo[2.2.1]hept-2-yl}carbonyl)-2,2-dimethylpropyl]-1H-indole-2-carboxamide; and N-{(1S)-2,2-dimethyl-1-[((1S,4S)-5-{[3-(methyloxy)-2,3'-bipyridin-6'-yl]carbonyl}-2,5-diazabicyclo[2.2.1]hept-2-yl)carbonyl]propyl}-1H-indole-2-carboxamide;

or a pharmaceutically acceptable salt thereof.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compounds of the general formula (I) and pharmaceutically acceptable derivatives and salts thereof may be accomplished as outlined below in Schemes 1-5. In the following description, the groups are as defined above for compounds of formula (I) unless otherwise indicated. Starting materials are commercially available or are made from commercially available starting materials using methods known to those skilled in the art.

Scheme 1

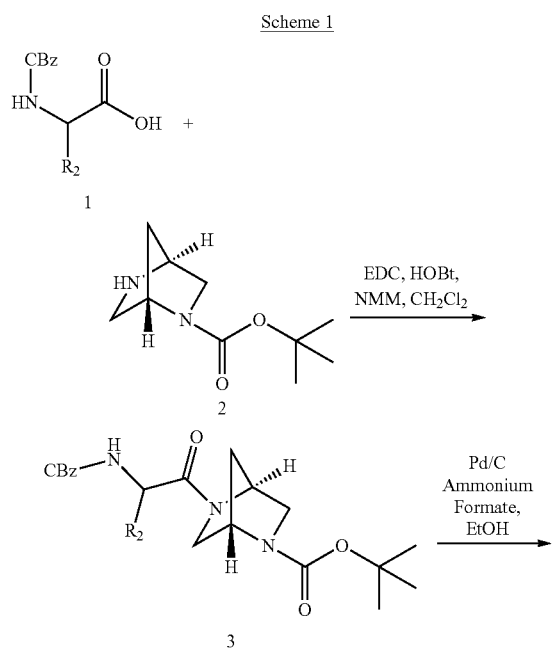

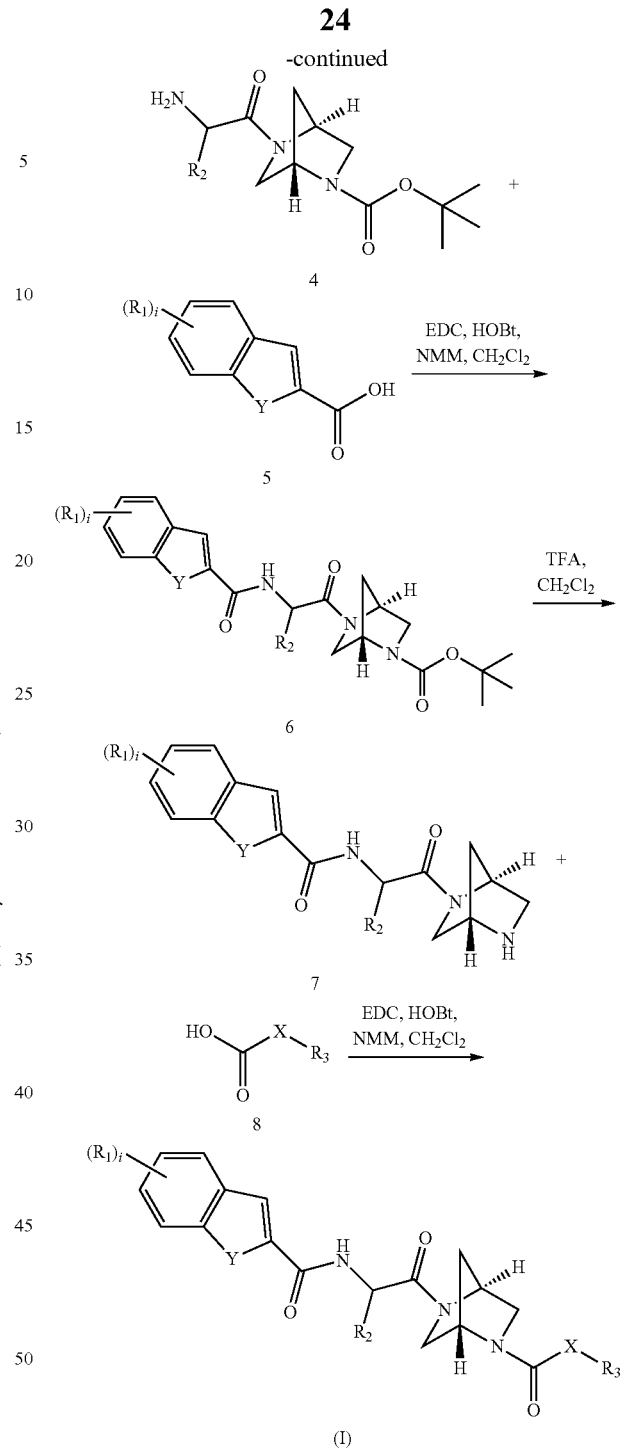

When the central diamine core is of the (S,S)-configuration, target molecules may be prepared from N-Boc-(1S,4S)-2,5-diazabicyclo[2.2.1]heptane as outlined in Scheme 1. The free secondary amine of N-Boc-(1S,4S)-2,5-diazabicyclo[2.2.1]heptane 2 can be coupled to an appropriate carboxylic acid 1 under conditions common to the art such as EDC in the presence of a base such as N-methylmorpholine or triethylamine, and a coupling modifier such as HOBt to provide the amide intermediate 3. Subsequent CBz deprotection under standard conditions such as by treatment with Pd/C with ammonium formate provides the amine intermediate 4. Treatment of intermediate 4 with an appropriate carboxylic acid 5 under conditions common to the art such as EDC in the presence of a base such as N-methylmorpholine and a coupling modifier such as HOBt provides the amide intermediate 6. Subsequent Boc deprotection can be accomplished under conditions common to the art such as treatment with an acid such as hydrochloric acid in 1,4-dioxane and methanol or TFA in dichloromethane to provide intermediate 7. Treatment of intermediate 7 with an appropriate carboxylic acid 8 under conditions common to the art such as EDC in the presence of a base and a coupling modifier provides the compound of Formula (I).

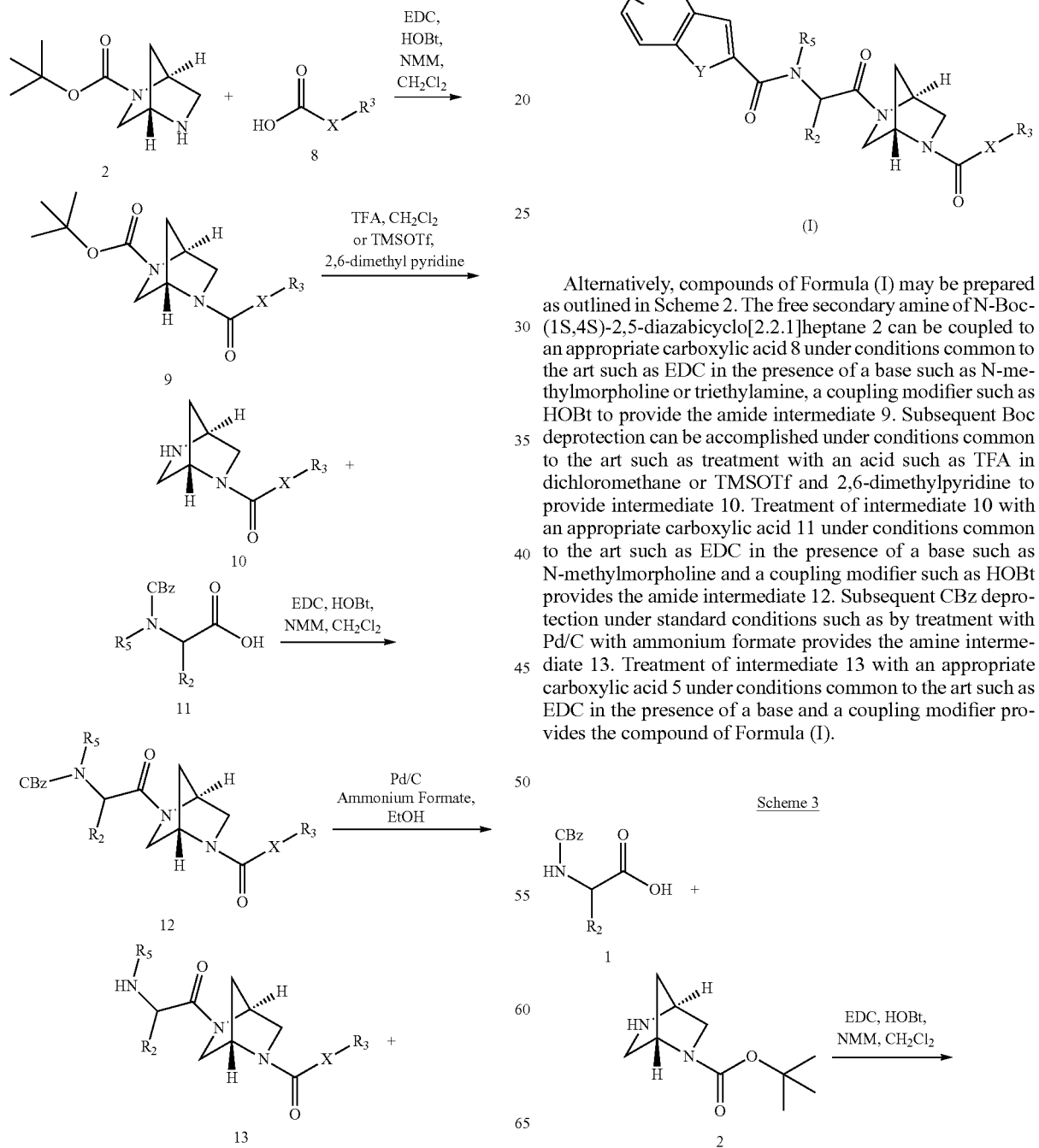

Alternatively, compounds of Formula (I) may be prepared as outlined in Scheme 2. The free secondary amine of N-Boc-(1S,4S)-2,5-diazabicyclo[2.2.1]heptane 2 can be coupled to an appropriate carboxylic acid 8 under conditions common to the art such as EDC in the presence of a base such as N-methylmorpholine or triethylamine, a coupling modifier such as HOBt to provide the amide intermediate 9. Subsequent Boc deprotection can be accomplished under conditions common to the art such as treatment with an acid such as TFA in dichloromethane or TMSOTf and 2,6-dimethylpyridine to provide intermediate 10. Treatment of intermediate 10 with an appropriate carboxylic acid 11 under conditions common to the art such as EDC in the presence of a base such as N-methylmorpholine and a coupling modifier such as HOBt provides the amide intermediate 12. Subsequent CBz deprotection under standard conditions such as by treatment with Pd/C with ammonium formate provides the amine intermediate 13. Treatment of intermediate 13 with an appropriate carboxylic acid 5 under conditions common to the art such as EDC in the presence of a base and a coupling modifier provides the compound of Formula (I).

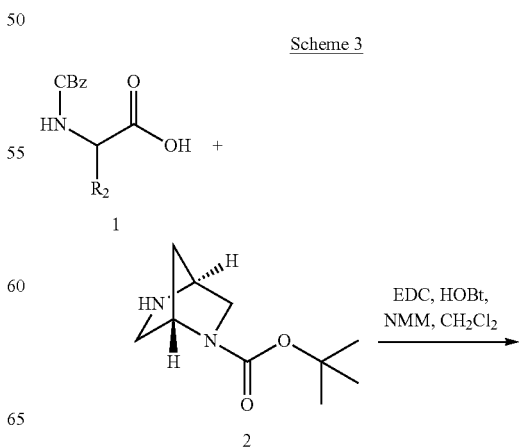

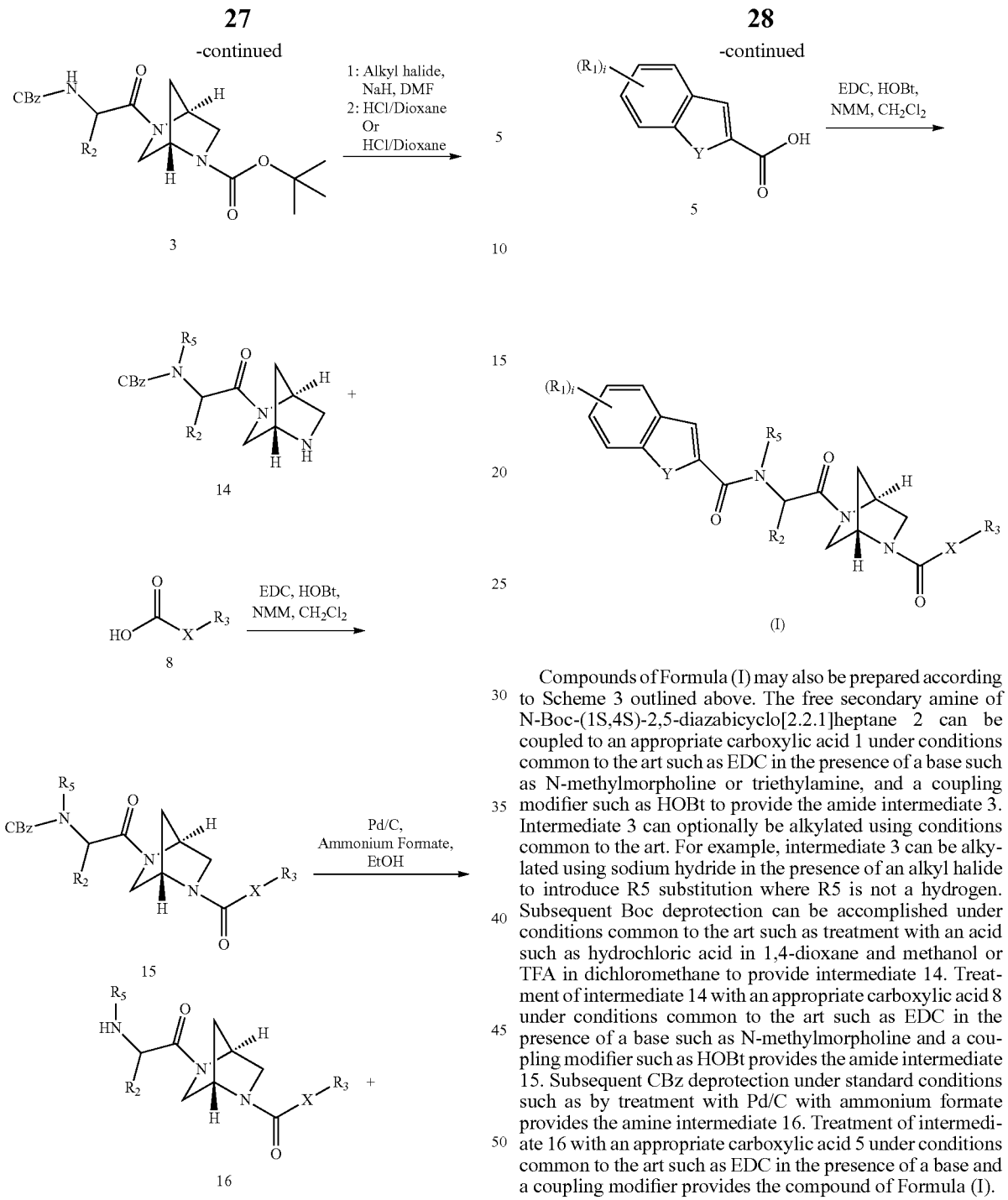

Compounds of Formula (I) may also be prepared according to Scheme 3 outlined above. The free secondary amine of N-Boc-(1S,4S)-2,5-diazabicyclo[2.2.1]heptane 2 can be coupled to an appropriate carboxylic acid 1 under conditions common to the art such as EDC in the presence of a base such as N-methylmorpholine or triethylamine, and a coupling modifier such as HOBt to provide the amide intermediate 3. Intermediate 3 can optionally be alkylated using conditions common to the art. For example, intermediate 3 can be alkylated using sodium hydride in the presence of an alkyl halide to introduce R5 substitution where R5 is not a hydrogen. Subsequent Boc deprotection can be accomplished under conditions common to the art such as treatment with an acid such as hydrochloric acid in 1,4-dioxane and methanol or TFA in dichloromethane to provide intermediate 14. Treatment of intermediate 14 with an appropriate carboxylic acid 8 under conditions common to the art such as EDC in the presence of a base such as N-methylmorpholine and a coupling modifier such as HOBt provides the amide intermediate 15. Subsequent CBz deprotection under standard conditions such as by treatment with Pd/C with ammonium formate provides the amine intermediate 16. Treatment of intermediate 16 with an appropriate carboxylic acid 5 under conditions common to the art such as EDC in the presence of a base and a coupling modifier provides the compound of Formula (I).

Scheme 4

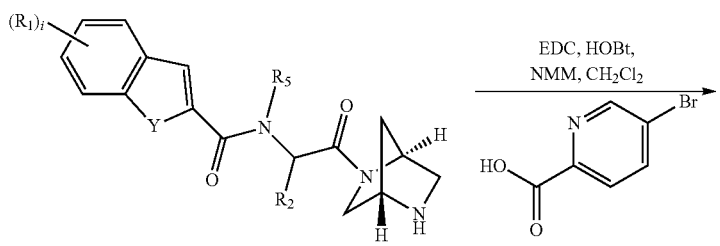

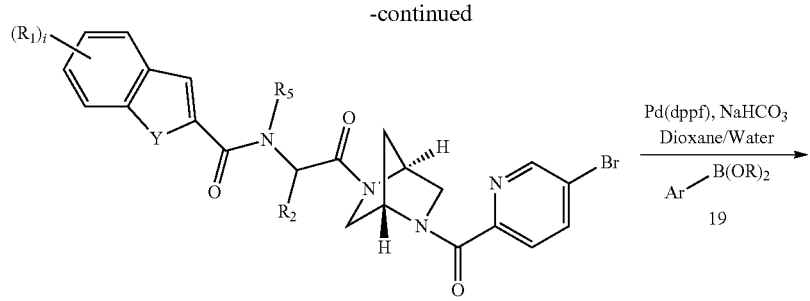

18

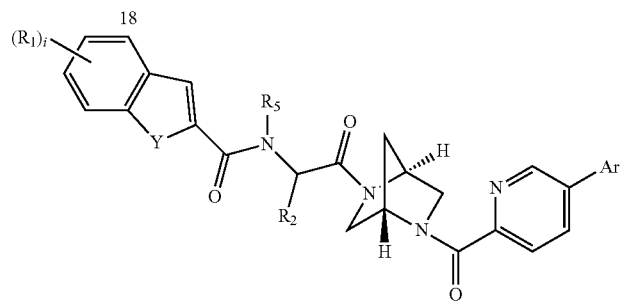

25

Compounds of Formula (I) could be converted to other compounds of Formula (I) by modification of appropriate functional groups using conditions common to the art. For example, treatment of intermediate 7 with carboxylic acid 17 under conditions common to the art such as EDC in the presence of a base such as N-methylmorpholine and a coupling modifier such as HOBt provides compound 18. Compound 18 can be converted to compounds of formula (I) by palladium mediated coupling with boronic acid 19, where Ar is optionally substituted phenyl or pyridyl.

Scheme 5

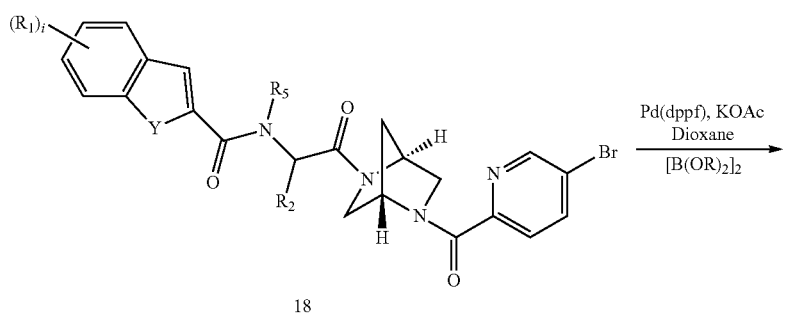

18

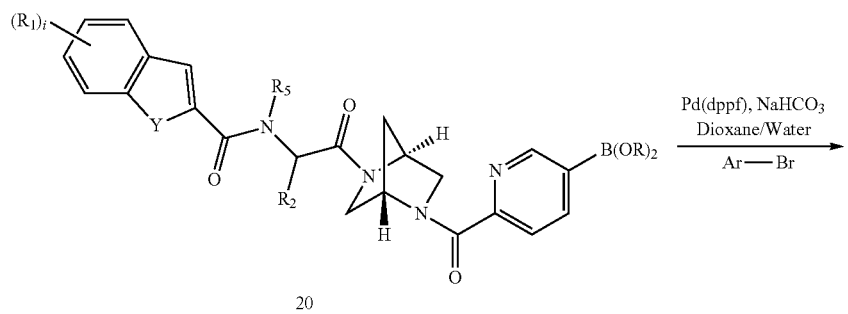

20

-continued

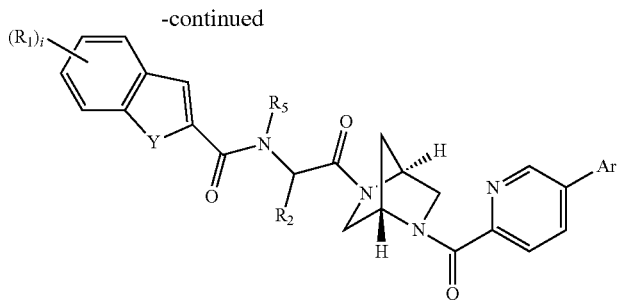

Alternatively, compound 18 can be converted to borate intermediate 20 by palladium mediated coupling reaction and then cross-coupled with aryl halide such as aryl bromide, aryl iodide or aryl chloride under Suzuki coupling conditions common to the art to afford compounds of formula (I) wherein Ar is optionally substituted phenyl or pyridyl.

Separation of diastereoisomers or cis and trans isomers may be achieved by conventional techniques, e.g. by fractional crystallization, chromatography, H.P.L.C. or SCF of a stereoisomeric mixture. Pure stereoisomer of the agent may also be prepared from the corresponding optically pure intermediate or by resolution, such as H.P.L.C. of the corresponding racemate using a suitable chiral support or by fractional crystallization of the diastereoisomeric salts formed by reaction of the corresponding racemate with a suitable optically active acid or base, as appropriate.

Biological Activity

As stated above, the compounds according to Formula I are TRPV4 antagonists, and are useful in the treatment or prevention of atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, cardiovascular disease, renal dysfunction and osteoarthritis.

The biological activity of the compounds according to Formula I can be determined using any suitable assay for determining the activity of a candidate compound as a TRPV4 antagonist, as well as tissue and in vivo models.

The biological activity of the compounds of Formula (I) are demonstrated by the following tests.

Ligand-Gated Assay:

TRP channel activation/opening results in an influx of divalent and monovalent cations including calcium. The resulting changes in intracellular calcium are monitored using a calcium selective fluorescent dye Fluo4 (MDS Analytical Technologies). Dye loaded cells are initially exposed to test compound to verify a lack of agonist activity. Cells are subsequently activated by addition of an agonist and inhibition of the agonist-induced activation is recorded. Human embryonic kidney 293 cells stably expressing the macrophage scavenger receptor class II (HEK-293-MSR-II) and transduced with 1% BacMam (J. P. Condreay, S. M. Witherspoon, W. C. Clay and T. A. Kost, Proc Natl Acad Sci 96 (1999), pp. 127-132) virus expressing the human TRPV4 gene are plated at 15000 cells/well in a volume of 50 uL in a 384 well poly-D lysine coated plate. Cells are incubated for 24 hours at 37 degrees and 5% $CO_2$. Media is then aspirated using a Tecan Plate-washer and replaced with 20 uL of dye loading buffer: HBSS, 500 uM Brilliant Black (MDS Analytical Technologies), 2 uM Fluo-4. Dye loaded plates are then incubated in the dark at room temperature for 1-1.5 hours. 10 uL of test compound diluted in HBSS+0.01% Chaps is added to the plate, incubated for 10 min at room temperature in the dark and then 10 uL of agonist is added at a final conc. equal to the agonist EC80. Calcium release is measured using the FLIPRtetra (MDS Analytical Technologies).

All examples described herein possessed TRPV4 biological activity with $IC_{50}$s ranges from 1 nM-10 uM.

Hypotonicity Assay (HEK293 Cells):

TRP channel activation/opening results in an influx of divalent and monovalent cations including calcium. The resulting changes in intracellular calcium are monitored using a calcium selective fluorescent dye Fluo4 (Invitrogen™). Dye loaded cells are initially exposed to test compound to verify a lack of agonist activity. Cells are subsequently activated by addition of a hypotonic buffer and inhibition of the hypotonicity-induced activation is recorded.

50 uL of HEK293 cells stably transformed with human TRPV4 are plated at 30K cells per well in 384 well poly-D-lysine coated plates. The following day, the media is removed and replaced with 50 uL of dye loading buffer (Fluo-4 from Invitrogen diluted 1:500 in DMEM/F12) then the cells are incubated for 1.5 hours at room temperature in the dark. Dye is then removed and replaced with 50 uL of 310 mOsm isotonic buffer (130 mM NaCl, 2.5 mM KCl, 1 mg/mL D-glucose, 10 mM Hepes, 1.2 mM $MgCl_2$, 1.5 mM $CaCl_2$, 0.25% DMSO, pH 7.4) and incubated in dark at room temp for an additional hour. Test compounds are diluted in isotonic buffer to a final DMSO concentration of 0.25%. Using the Molecular Devices FLIPR instrument, 25 uL of diluted compound is added 30 seconds after start. At 8 minutes, 25 uL of 110-115 mOsm hypotonic buffer (2.5 mM KCl, 1 mg/mL D-glucose, 10 mM Hepes, 1.2 mM $MgCl_2$, 1.5 mM $CaCl_2$, 0.25% DMSO, 80 mM mannitol, pH 7.4) is added. Signal is recorded for a total of 20 minutes with reads every 4.5 seconds.

Hypotonicity Assay (BHK Cells):

BHK/AC9_DMEM/F12 conditioned (Baby Hamster Kidney) cells are transduced with 2% BacMam virus expressing the human TRPV4 gene and are plated at 10K cells per well in a volume of 50 uL in 384 well poly-D-lysine coated plates. Cells are incubated for 18-24 hours at 37 degrees and 5% $CO_2$. The following day, the media is aspirated using a Tecan Plate-washer and replaced with 20 uL of dye loading buffer: HBSS buffer, 2.5 mM Probenecid, 500 uM Brilliant Black, 2 uM Fluo-4. The dye loaded cells are incubated for 1-1.5 hours at room temperature in the dark. 10 uL of test compound diluted in HBSS/$H_2O$ (~1:2.3)+0.01% Chaps is added to the plate, incubated for 10 min at room temperature in the dark, and then 10 uL of hypotonic buffer ($H_2O$+1.5 mM $CaCl_2$+ ~68 mM NaCl; 140 mOsm stock/260 mOsm FAC) is used to test the inhibition of the hypotonicity-induced activation.

Reaction is measured on a heated stage (37 degrees) using the FLIPRtetra.

Methods of Use

The compounds of the invention are TRPV4 antagonists, and are useful in the treatment or prevention of atherosclerosis, disorders related to atherosclerosis, disorders related to intestinal edema, post-surgical abdominal edema, local and systemic edema, fluid retention, sepsis, hypertension, inflammation, bone related dysfunctions and congestive heart failure, pulmonary disorders, chronic obstructive pulmonary disorder, ventilator induced lung injury, high altitude induced pulmonary edema, acute respiratory distress syndrome, pulmonary fibrosis, sinusitis/rhinitis, asthma, overactive bladder, pain, cardiovascular disease, renal dysfunction and osteoarthritis. Accordingly, in another aspect the invention is directed to methods of treating such conditions.

The methods of treatment of the invention comprise administering a safe and effective amount of a compound according to Formula I or a pharmaceutically-acceptable salt thereof to a patient in need thereof.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "safe and effective amount" in reference to a compound of the invention or other pharmaceutically-active agent means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "patient" refers to a human or other animal.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per dose.

Additionally, the compounds of the invention may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

Compositions

The compounds of the invention will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain one compound of the invention. However, in certain embodiments, the pharmaceutical compositions of the invention contain more than one compound of the invention.

For example, in certain embodiments the pharmaceutical compositions of the invention contain two compounds of the invention. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

The compounds may be administered alone or in conjunction with one or more other therapeutic agents, said agents being selected from the group consisting endothelin receptor antagonists, angiotensin converting enzyme (ACE) inhibitors, angiotension II receptor antagonists, vasopeptidase inhibitors, diuretics, digoxin, beta blocker, aldosterone antagonists, iontropes, NSAIDS, nitric oxide donors, calcium channel modulators, muscarinic antagonists, steroidal anti-inflammatory drugs, bronchodilators, Leukotriene antagonists, anti-histamines, HMG-CoA reductase inhibitors, dual non-selective $\beta$-adrenoceptor and $\alpha_1$-adrenoceptor antagonists, type-5 phosphodiesterase inhibitors, and renin inhibitors.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

In the Examples:

Chemical shifts are expressed in parts per million (ppm) units. Coupling constants (J) are in units of hertz (Hz). Splitting patterns describe apparent multiplicities and are designated as s (singlet), d (doublet), t (triplet), q (quartet), dd (double doublet), dt (double triplet), m (multiplet), br (broad).

Flash column chromatography was performed on silica gel.

The naming program used is ACD Name Pro 6.02.

The following abbreviations and terms had the indicated meanings throughout:

BOC (tert-butyloxycarbonyl);
CBz (carbobenzoxy);
$CH_2Cl_2$ (dichloromethane);
EDC (1-[3-dimethylamino) propyl]-3-ethylcarbodiimide hydrochloride);
EtOH (ethanol);
$H_2$ (hydrogen);
HCl (hydrochloric acid);
HOBt (1-hydroxybenzotriazole);
$Na_2SO_4$ (sodium sulfate);
$NaHCO_3$ (sodium bicarbonate);
NaOH (sodium hydroxide);
NMM (N-methyl morpholine);
Pd/C (palladium on carbon);
$PdCl_2$ (2'-(Dimethylamiono)-2-Biphenyl-palladium(II) HPNor$_2$ Chloride Dinorbornylphosphine Complex);
TFA (trifluoroacetic acid);

Example 1

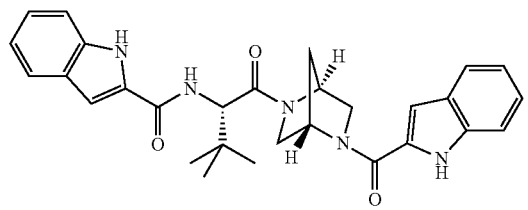 [SMILES: CC(C)(C)[C@H](NC(=O)c1cc2ccccc2[nH]1)C(=O)N1C[C@@H]2C[C@H]1CN2C(=O)c1cc2ccccc2[nH]1]

N-((1S)-1-{[1S,4S)-5-(1H-indol-2-ylcarbonyl)-2,5-diazabicyclo[2.2.1]hept-2-yl]carbonyl}-2,2-dimethylpropyl)-1H-indole-2-carboxamide

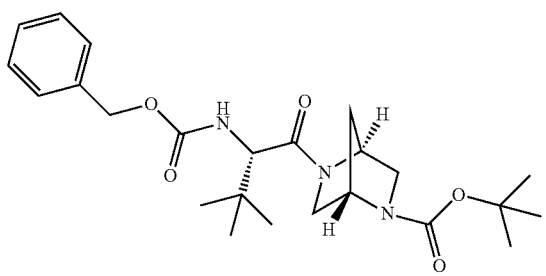 [SMILES: CC(C)(C)OC(=O)N1C[C@@H]2C[C@H]1CN2C(=O)[C@@H](NC(=O)OCc1ccccc1)C(C)(C)C]

1,1-Dimethylethyl (1S,4S)-5-(3-methyl-N-{[phenylmethyl)oxy]carbonyl}-L-valyl)-2,5-diazabicyclo[2.2.1]heptane-2-carboxylate a) To a solution of 1,1-dimethylethyl (1S,4S)-2,5-diazabicyclo[2.2.1]heptane-2-carboxylate (16.47 g, 83 mmol) in $CH_2Cl_2$ (200 mL) was added EDC (19.1 g, 99.7 mmol), HOBt (2.24 g, 16.6 mmol), 3-methyl-N-{[(phenylmethyl)oxy]carbonyl}-L-valine (22.0 g, 83 mmol), and NMM (23 g, 227 mmol). The reaction mixture was stirred at room temperature for 18 h. The reaction was diluted with $CH_2Cl_2$ and washed with sat. $NaHCO_3$ (100 mL), 1N HCl (100 mL), sat. $NaHCO_3$ (100 mL) and brine. The organic layer was dried over $Na_2SO_4$, filtered, and concentrated to yield the crude product. LCMS (m/z): 446.3 (M+H).

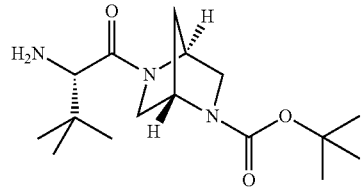 [SMILES: CC(C)(C)OC(=O)N1C[C@@H]2C[C@H]1CN2C(=O)[C@@H](N)C(C)(C)C]

1,1-Dimethylethyl (1S,4S)-5-(3-methyl-L-valyl)-2,5-diazabicyclo[2.2.1]heptane-2-carboxylate b) To a solution of 1,1-dimethylethyl (1S,4S)-5-(3-methyl-N-{[(phenylmethyl)oxy]carbonyl}-L-valyl)-2,5-diazabicyclo[2.2.1]heptane-2-carboxylate (31.6 g, 71 mmol) in MeOH (600 mL) was added Pd/C (12 g). The mixture was stirred for 18 h at room temperature under an atmosphere of $H_2$ (40 psi). The reaction mixture was then filtered and the organic layer was concentrated to yield the crude product. LCMS (m/z): 312.3 (M+H).

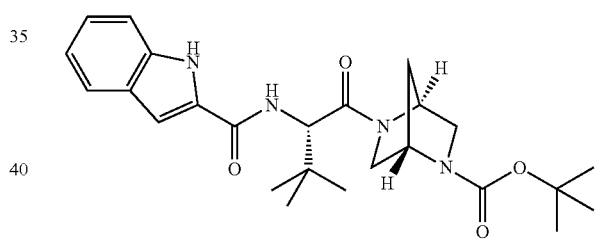

1,1-Dimethylethyl (1S,4S)-5-[N-(1H-indol-2-ylcarbonyl)-3-methyl-L-valyl]-2,5-diazabicyclo[2.2.1]heptane-2-carboxylate c) To a solution of 1H-indole-2-carboxylic acid (14.6 g, 91 mmol) in $CH_2Cl_2$ (300 mL) was added 1,1-dimethylethyl (1S,4S)-5-(3-methyl-L-valyl)-2,5-diazabicyclo[2.2.1]heptane-2-carboxylate (28.1 g, 91 mmol), EDC (20.9 g, 109 mmol), HOBt (2.45 g, 18 mmol), and NMM (25.2 g, 249 mmol). The reaction mixture was stirred at room temperature for 18 h. The reaction was diluted with $CH_2Cl_2$ and washed with sat. $NaHCO_3$ (150 mL), 1N HCl (150 mL), sat. $NaHCO_3$ (150 mL) and brine (200 mL). The organic layer was dried over $Na_2SO_4$, filtered, and concentrated to give the crude product which was purified by column chromatography (petroleum ether/ethyl acetate, 2:1). Concentration of the desired fractions afforded the title compound (40.5 g) as a yellow solid. LCMS (m/z): 455.3 (M+H).

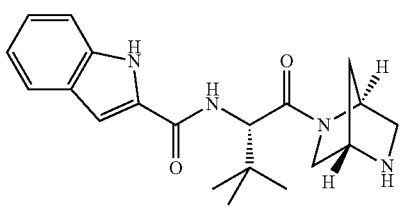 [SMILES: CC(C)(C)[C@H](NC(=O)c1cc2ccccc2[nH]1)C(=O)N1C[C@@H]2C[C@H]1CN2]

N-{(1S)-1-[(1S,4S)-2,5-diazabicyclo[2.2.1]hept-2-ylcarbonyl]-2,2-dimethylpropyl}-1H-indole-2-carboxamide d) To a solution of 1,1-dimethylethyl (1S,4S)-5-[N-(1H-indol-2-ylcarbonyl)-3-methyl-L-valyl]-2,5-diazabicyclo[2.2.1]heptane-2-carboxylate (40.5 g, 89.2 mmol) in CH$_2$Cl$_2$ (300 mL) was added TFA (75 mL) at 0° C. The mixture was stirred at room temperature for 18 h. The reaction was quenched with 1N NaOH while adjusting the pH of the solution to 8-9. The reaction was then extracted with CH$_2$Cl$_2$ (3×500 mL), dried over Na$_2$SO$_4$, filtered, and concentrated to yield the crude product. LCMS (m/z): 355.3 (M+H).

N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide e) To a solution of N-{(1S)-1-[(1S,4S)-2,5-diazabicyclo[2.2.1]hept-2-ylcarbonyl]-2,2-dimethylpropyl}-1H-indole-2-carboxamide (120 mg, 0.34 mmol) in CH$_2$Cl$_2$ (4 mL) was added 1H-indole-2-carboxylic acid (55 mg, 0.34 mmol), EDC (78 mg, 0.41 mmol), HOBt (9 mg, 0.07 mmol) and NMM (102 mg, 0.93 mmol). The reaction mixture was stirred at room temperature for 3 h. The reaction was diluted with CH$_2$Cl$_2$ (5 mL) and washed with sat. NaHCO$_3$ (10 mL), 1N HCl (10 mL), sat. NaHCO$_3$ (10 mL) and brine (10 mL). The organic layer was dried over Na$_2$SO$_4$, filtered, and concentrated to yield the crude product. The material was purified by HPLC (YMC C18 5.0 uM 250*20 mm) and then recrystallized from water, dried by lyophilization to afford 64 mg of the title compound: LCMS (m/z): 498.4 (M+H); $^1$H NMR (400 MHz, CDCl$_3$) δ ppm 0.98-1.16 (9H, m), 1.83-2.07 (3H, m), 3.52-3.96 (4H, m), 4.65-5.20 (3H, m), 6.62-6.98 (3H, m), 7.06-7.18 (2H, m), 7.21-7.45 (3H, m), 7.53-7.68 (2H, m), 9.42-9.73 (2H, m).

Examples 2-44

The compounds in Table 1 were prepared by a method similar to the one described for the preparation of N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide (Example 1). As is appreciated by those skilled in the art, these analogous examples may involve variations in general reaction conditions.

TABLE 1

| Ex # | Structure | Name | LCMS [M + 1]$^+$ |
|---|---|---|---|
| 2 | 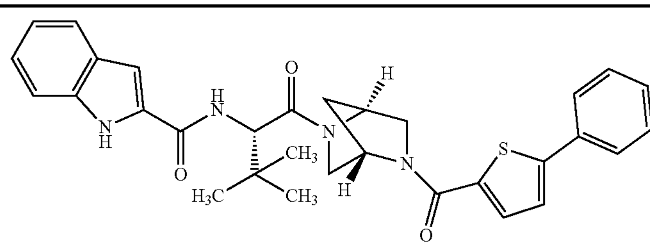 | N-[(1S)-2,2-dimethyl-1-({(1S,4S)-5-[(5-phenyl-2-thienyl)carbonyl]-2,5-diazabicyclo[2.2.1]hept-2-yl}carbonyl)propyl]-1H-indole-2-carboxamide | 541.3 |
| 3 | 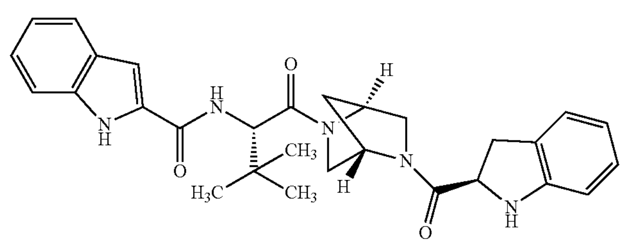 | N-[(1S)-1-({(1S,4S)-5-[(2R)-2,3-dihydro-1H-indol-2-ylcarbonyl]-2,5-diazabicyclo[2.2.1]hept-2-yl}carbonyl)-2,2-dimethylpropyl]-1H-indole-2-carboxamide | 500.4 |

TABLE 1-continued

| Ex # | Structure | Name | LCMS [M + 1]+ |
|---|---|---|---|
| 4 | 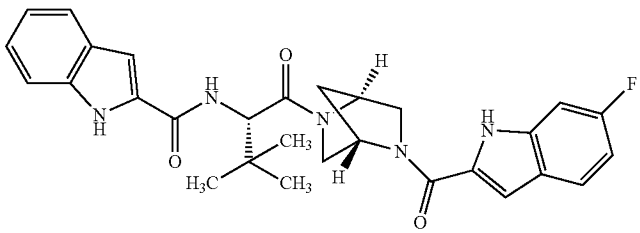 | N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide | 516.3 |
| 5 | 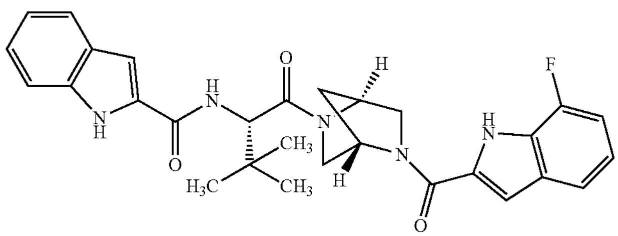 | N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide | 516.4 |
| 6 | 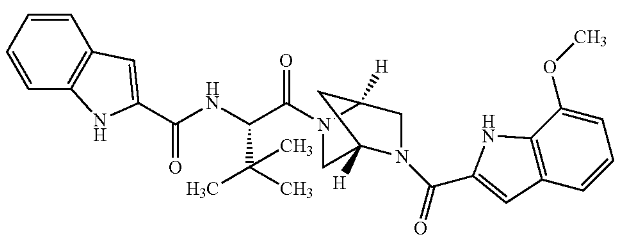 | N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide | 528.4 |
| 7 | 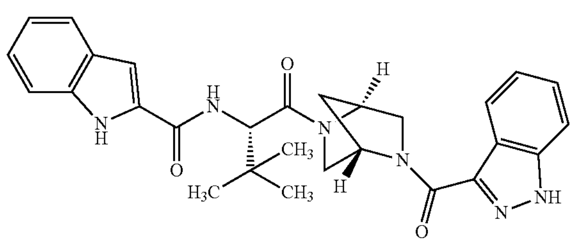 | N-((1S)-1-{[(1S,4S)-5-(1H-indazol-3-ylcarbonyl)-2,5-diazabicyclo[2.2.1]hept-2-yl]carbonyl}-2,2-dimethylpropyl)-1H-indole-2-carboxamide | 499.4 |
| 8 | 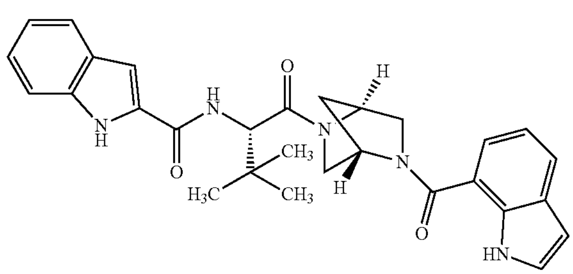 | N-((1S)-1-{[(1S,4S)-5-(1H-indol-7-ylcarbonyl)-2,5-diazabicyclo[2.2.1]hept-2-yl]carbonyl}-2,2-dimethylpropyl)-1H-indole-2-carboxamide | 498.4 |
| 9 | 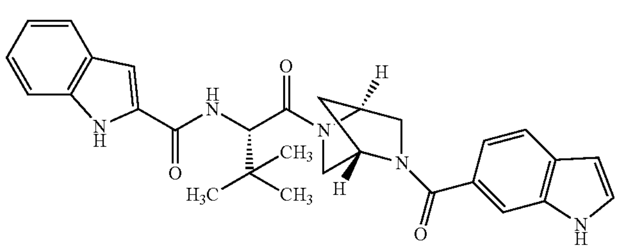 | N-((1S)-1-{[(1S,4S)-5-(1H-indol-6-ylcarbonyl)-2,5-diazabicyclo[2.2.1]hept-2-yl]carbonyl}-2,2-dimethylpropyl)-1H-indole-2-carboxamide | 498.4 |

TABLE 1-continued

| Ex # | Structure | Name | LCMS [M + 1]+ |
|---|---|---|---|
| 10 | 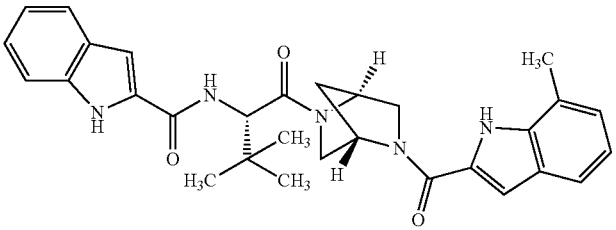 | N-[(1S)-2,2-dimethyl-1-({(1S,4S)-5-[(7-methyl-1H-indol-2-yl)carbonyl]-2,5-diazabicyclo[2.2.1]hept-2-yl}carbonyl)propyl]-1H-indole-2-carboxamide | 512.4 |
| 11 | 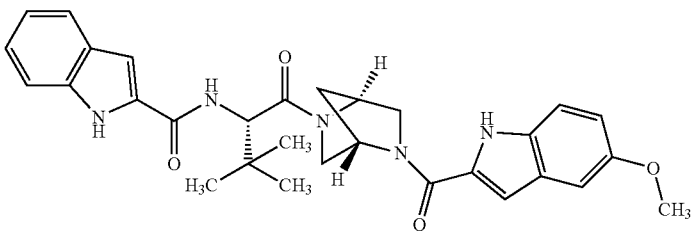 | N-{(1S)-2,2-dimethyl-1-[((1S,4S)-5-{[5-methyloxy)-1H-indol-2-yl]carbonyl}-2,5-diazabicyclo[2.2.1]hept-2-yl)carbonyl]propyl}-1H-indole-2-carboxamide | 528.4 |
| 12 | 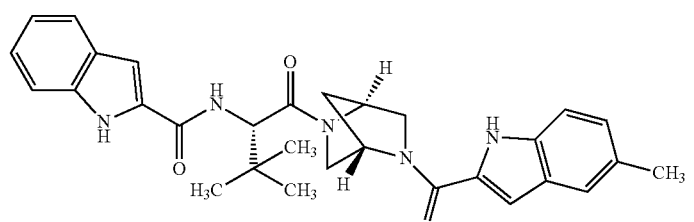 | N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide | 512.4 |
| 13 | 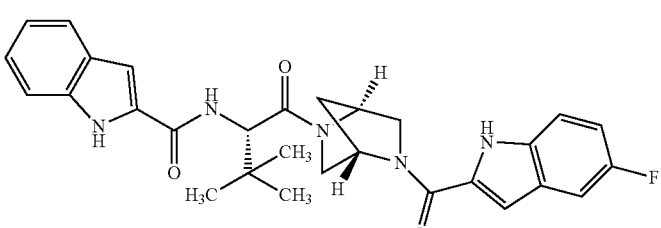 | N-[(1S)-1-({(1S,4S)-5-[(5-fluoro-1H-indol-2-yl)carbonyl]-2,5-diazabicyclo[2.2.1]hept-2-yl}carbonyl)-2,2-dimethylpropyl]-1H-indole-2-carboxamide | 516.3 |
| 14 | 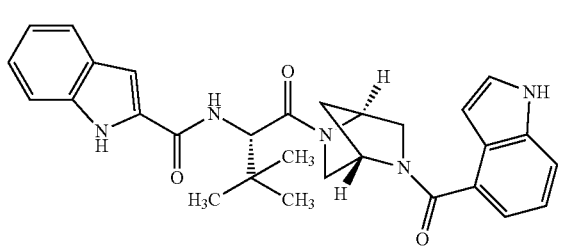 | N-((1S)-1-{[(1S,4S)-5-(1H-indol-4-ylcarbonyl)-2,5-diazabicyclo[2.2.1]hept-2-yl]carbonyl}-2,2-dimethylpropyl)-1H-indole-2-carboxamide | 498.4 |
| 15 | 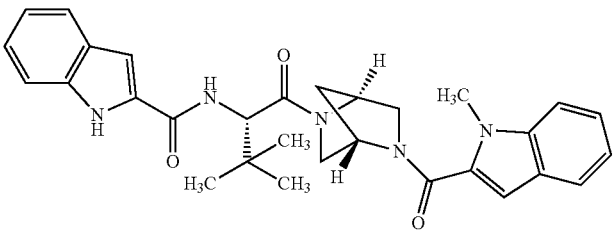 | N-[(1S)-2,2-dimethyl-1-({(1S,4S)-5-[(1-methyl-1H-indol-2-yl)carbonyl]-2,5-diazabicyclo[2.2.1]hept-2-yl}carbonyl)propyl]-1H-indole-2-carboxamide | 512.4 |

TABLE 1-continued

| Ex # | Structure | Name | LCMS [M + 1]+ |
|---|---|---|---|
| 16 | 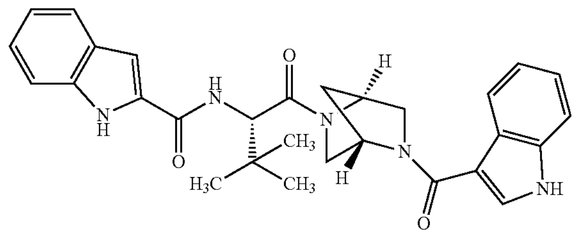 | N-((1S)-1-{[(1S,4S)-5-(1H-indol-3-ylcarbonyl)-2,5-diazabicyclo[2.2.1]hept-2-yl]carbonyl}-2,2-dimethylpropyl)-1H-indole-2-carboxamide | 498.4 |
| 17 | 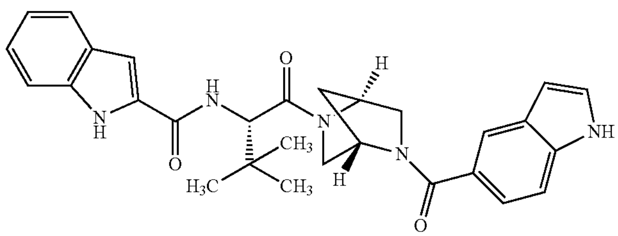 | N-((1S)-1-{[(1S,4S)-5-(1H-indol-5-ylcarbonyl)-2,5-diazabicyclo[2.2.1]hept-2-yl]carbonyl}-2,2-dimethylpropyl)-1H-indole-2-carboxamide | 498.4 |
| 18 | 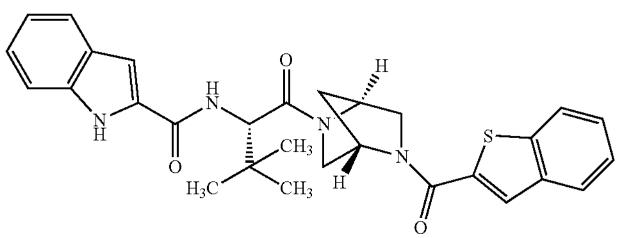 | N-((1S)-1-{[(1S,4S)-5-(1-benzothien-2-ylcarbonyl)-2,5-diazabicyclo[2.2.1]hept-2-yl]carbonyl}-2,2-dimethylpropyl)-1H-indole-2-carboxamide | 515.4 |
| 19 | 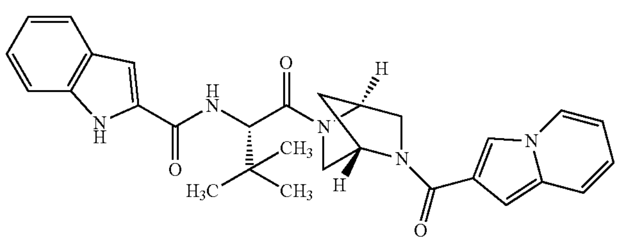 | N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide | 498.4 |
| 20 | 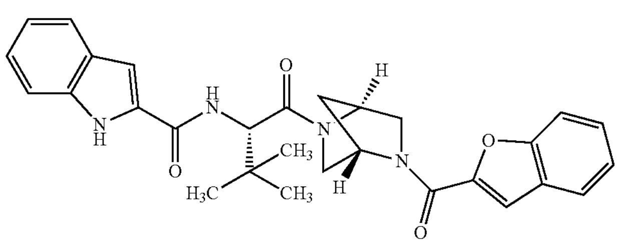 | N-((1S)-1-{[(1S,4S)-5-(1-benzofuran-2-ylcarbonyl)-2,5-diazabicyclo[2.2.1]hept-2-yl]carbonyl}-2,2-dimethylpropyl)-1H-indole-2-carboxamide | 499.4 |
| 21 | 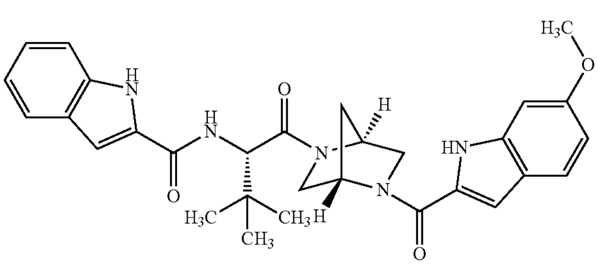 [SMILES: COc1ccc2cc(C(=O)N3C[C@@H]4C[C@H]3CN4C(=O)[C@@H](NC(=O)c3cc4ccccc4[nH]3)C(C)(C)C)[nH]c2c1] | N-{(1S)-2,2-dimethyl-1-[(((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide | 528.3 |

TABLE 1-continued

| Ex # | Structure | Name | LCMS [M + 1]+ |
|---|---|---|---|
| 22 | 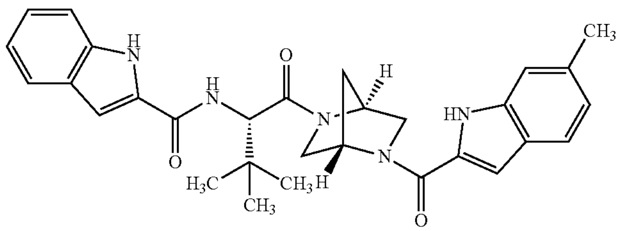 [SMILES: Cc1ccc2cc(C(=O)N3C[C@@H]4C[C@H]3CN4C(=O)[C@@H](NC(=O)c3cc4ccccc4[nH]3)C(C)(C)C)[nH]c2c1] | N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide | 512.3 |
| 23 | 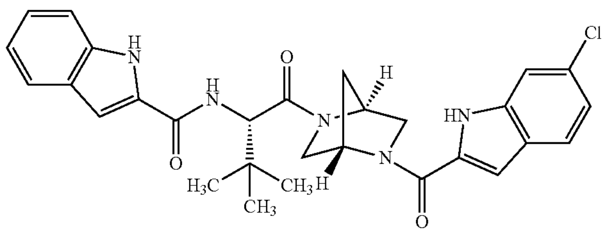 [SMILES: CC(C)(C)[C@H](NC(=O)c1cc2ccccc2[nH]1)C(=O)N1C[C@@H]2C[C@H]1CN2C(=O)c1cc2ccc(Cl)cc2[nH]1] | N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide | 532.2 |
| 24 | 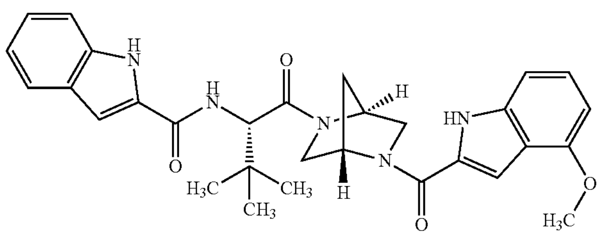 [SMILES: COc1cccc2[nH]c(C(=O)N3C[C@@H]4C[C@H]3CN4C(=O)[C@@H](NC(=O)c3cc4ccccc4[nH]3)C(C)(C)C)cc12] | N-{(1S)-2,2-dimethyl-1-[((1S,4S)-5-{[4-(methyloxy)-1H-indol-2-yl]carbonyl}-2,5-diazabicyclo[2.2.1]hept-2-yl)carbonyl]propyl}-1H-indole-2-carboxamide | 528.3 |
| 25 | 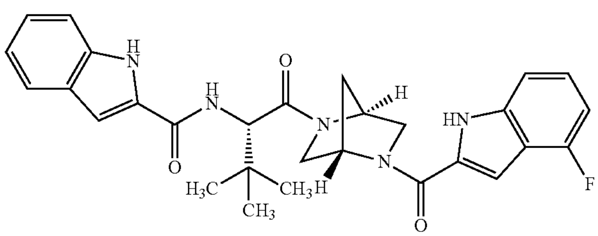 [SMILES: CC(C)(C)[C@H](NC(=O)c1cc2ccccc2[nH]1)C(=O)N1C[C@@H]2C[C@H]1CN2C(=O)c1cc2c(F)cccc2[nH]1] | N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide | 516.3 |
| 26 | 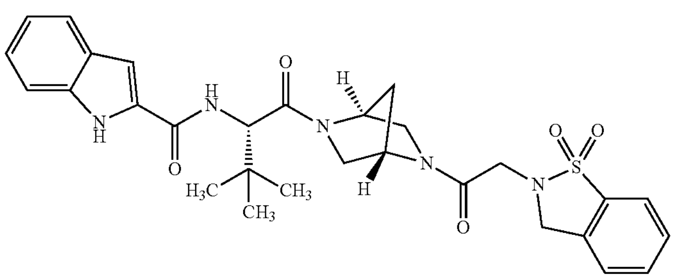 [SMILES: CC(C)(C)[C@H](NC(=O)c1cc2ccccc2[nH]1)C(=O)N1C[C@@H]2C[C@H]1CN2C(=O)CN1Cc2ccccc2S1(=O)=O] | N-[(1S)-1-({(1S,4S)-5-[(1,1-dioxido-1,2-benzisothiazol-2(3H)-yl)acetyl]-2,5-diazabicyclo[2.2.1]hept-2-yl}carbonyl)-2,2-dimethylpropyl]-1H-indole-2-carboxamide | 564.2 |
| 27 | 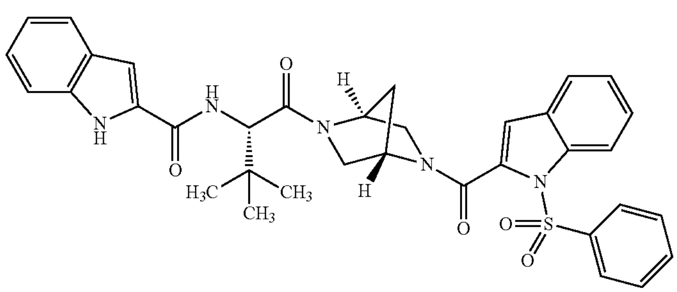 [SMILES: CC(C)(C)[C@H](NC(=O)c1cc2ccccc2[nH]1)C(=O)N1C[C@@H]2C[C@H]1CN2C(=O)c1cc2ccccc2n1S(=O)(=O)c1ccccc1] | N-{(1S)-2,2-dimethyl-1-[((1S,4S)-5-{[1-(phenylsulfonyl)-1H-indol-2-yl]carbonyl}-2,5-diazabicyclo[2.2.1]hept-2-yl)carbonyl]propyl}-1H-indole-2-carboxamide | 638.2 |

TABLE 1-continued

| Ex # | Structure | Name | LCMS [M + 1]+ |
|---|---|---|---|
| 28 | 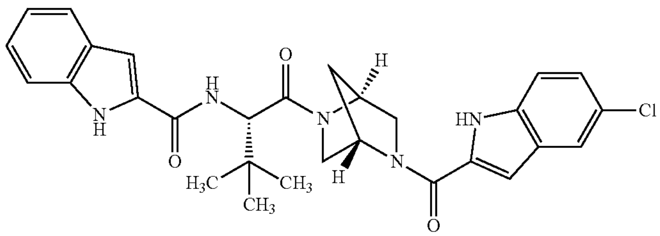 [SMILES: CC(C)(C)[C@H](NC(=O)c1cc2ccccc2[nH]1)C(=O)N1C[C@@H]2C[C@H]1CN2C(=O)c1cc2cc(Cl)ccc2[nH]1] | N-[(1S)-1-({(1S,4S)-5-[(5-chloro-1H-indol-2-yl)carbonyl]-2,5-diazabicyclo[2.2.1]hept-2-yl}carbonyl)-2,2-dimethylpropyl]-1H-indole-2-carboxamide | 532.4 |
| 29 | 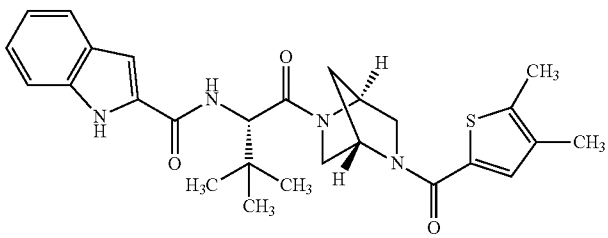 [SMILES: Cc1cc(C(=O)N2C[C@@H]3C[C@H]2CN3C(=O)[C@@H](NC(=O)c2cc3ccccc3[nH]2)C(C)(C)C)sc1C] | N-[(1S)-1-({(1S,4S)-5-[(4,5-dimethyl-2-thienyl)carbonyl]-2,5-diazabicyclo[2.2.1]hept-2-yl}carbonyl)-2,2-dimethylpropyl]-1H-indole-2-carboxamide | 493.4 |
| 30 | 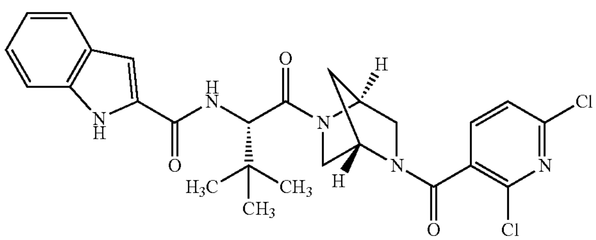 [SMILES: CC(C)(C)[C@H](NC(=O)c1cc2ccccc2[nH]1)C(=O)N1C[C@@H]2C[C@H]1CN2C(=O)c1ccc(Cl)nc1Cl] | N-[(1S)-1-({(1S,4S)-5-[(2,6-dichloro-3-pyridinyl)carbonyl]-2,5-diazabicyclo[2.2.1]hept-2-yl}carbonyl)-2,2-dimethylpropyl]-1H-indole-2-carboxamide | 528.3 |
| 31 | 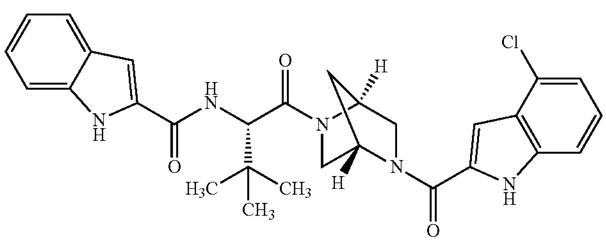 [SMILES: CC(C)(C)[C@H](NC(=O)c1cc2ccccc2[nH]1)C(=O)N1C[C@@H]2C[C@H]1CN2C(=O)c1cc2c(Cl)cccc2[nH]1] | N-[(1S)-1-({(1S,4S)-5-[(4-chloro-1H-indol-2-yl)carbonyl]-2,5-diazabicyclo[2.2.1]hept-2-yl}carbonyl)-2,2-dimethylpropyl]-1H-indole-2-carboxamide | 532.3 |
| 32 | 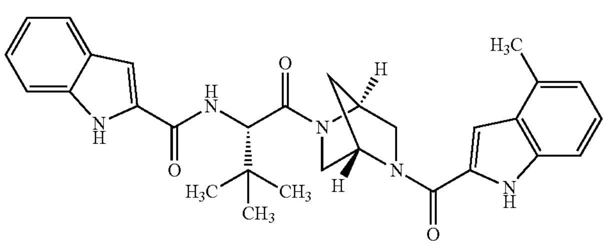 [SMILES: Cc1cccc2[nH]c(C(=O)N3C[C@@H]4C[C@H]3CN4C(=O)[C@@H](NC(=O)c3cc4ccccc4[nH]3)C(C)(C)C)cc12] | N-[(1S)-2,2-dimethyl-1-({(1S,4S)-5-[(4-methyl-1H-indol-2-yl)carbonyl]-2,5-diazabicyclo[2.2.1]hept-2-yl}carbonyl)propyl]-1H-indole-2-carboxamide | 512.4 |
| 33 | 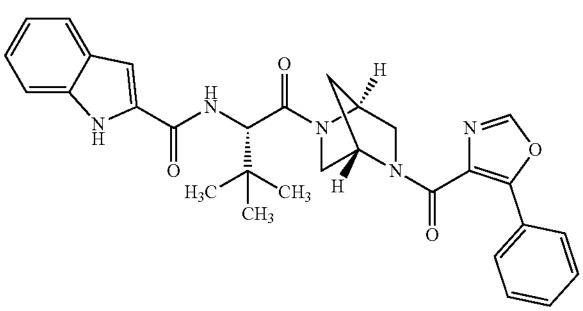 [SMILES: CC(C)(C)[C@H](NC(=O)c1cc2ccccc2[nH]1)C(=O)N1C[C@@H]2C[C@H]1CN2C(=O)c1ncoc1-c1ccccc1] | N-[(1S)-2,2-dimethyl-1-({(1S,4S)-5-[(5-phenyl-1,3-oxazol-4-yl)carbonyl]-2,5-diazabicyclo[2.2.1]hept-2-yl}carbonyl)propyl]-1H-indole-2-carboxamide | 526.1 |

TABLE 1-continued

| Ex # | Structure | Name | LCMS [M + 1]+ |
|---|---|---|---|
| 34 | 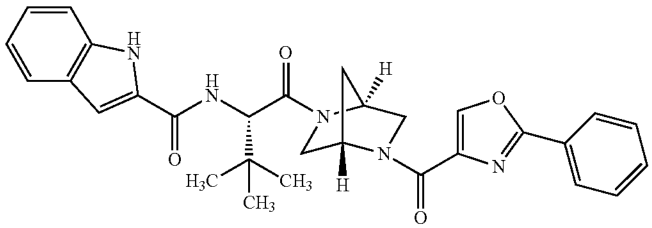 [SMILES: CC(C)(C)[C@H](NC(=O)c1cc2ccccc2[nH]1)C(=O)N1C[C@@H]2C[C@H]1CN2C(=O)c1coc(-c2ccccc2)n1] | N-[(1S)-2,2-dimethyl-1-({(1S,4S)-5-[(2-phenyl-1,3-oxazol-4-yl)carbonyl]-2,5-diazabicyclo[2.2.1]hept-2-yl}carbonyl)propyl]-1H-indole-2-carboxamide | 526.2 |
| 35 | 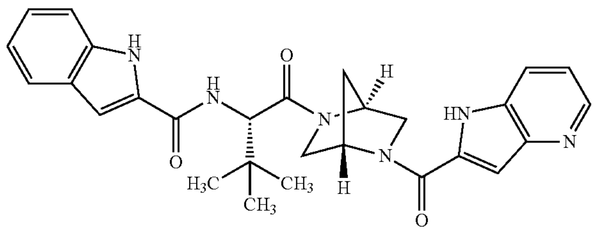 [SMILES: CC(C)(C)[C@H](NC(=O)c1cc2ccccc2[nH]1)C(=O)N1C[C@@H]2C[C@H]1CN2C(=O)c1cc2ncccc2[nH]1] | N-((1S)-2,2-dimethyl-1-{[(1S,4S)-5-(1H-pyrrolo[3,2-b]pyridin-2-ylcarbonyl)-2,5-diazabicyclo[2.2.1]hept-2-yl]carbonyl}propyl)-1H-indole-2-carboxamide | 499.2 |
| 36 | 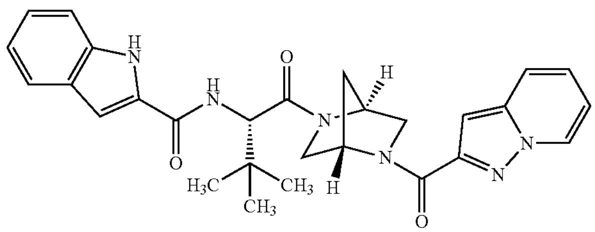 [SMILES: CC(C)(C)[C@H](NC(=O)c1cc2ccccc2[nH]1)C(=O)N1C[C@@H]2C[C@H]1CN2C(=O)c1cc2ccccn2n1] | N-((1S)-2,2-dimethyl-1-{[(1S,4S)-5-(pyrazolo[1,5-a]pyridin-2-ylcarbonyl)-2,5-diazabicyclo[2.2.1]hept-2-yl]carbonyl}propyl)-1H-indole-2-carboxamide | 499.2 |
| 37 | 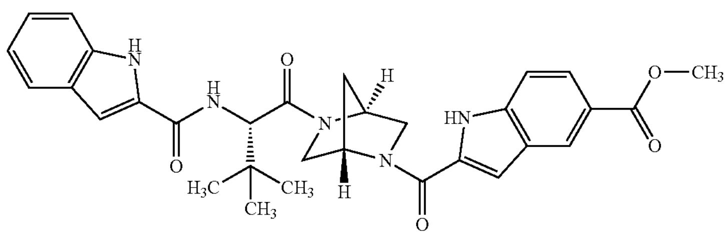 [SMILES: COC(=O)c1ccc2[nH]c(C(=O)N3C[C@@H]4C[C@H]3CN4C(=O)[C@@H](NC(=O)c3cc4ccccc4[nH]3)C(C)(C)C)cc2c1] | methyl 2-({(1S,4S)-5-[N-(1H-indol-2-ylcarbonyl)-3-methyl-L-valyl]-2,5-diazabicyclo[2.2.1]hept-2-yl}carbonyl)-1H-indole-5-carboxylate | 556.3 |
| 38 | 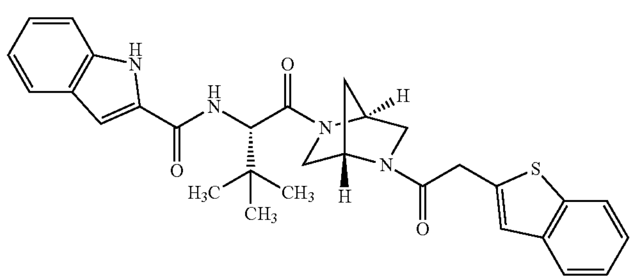 [SMILES: CC(C)(C)[C@H](NC(=O)c1cc2ccccc2[nH]1)C(=O)N1C[C@@H]2C[C@H]1CN2C(=O)Cc1cc2ccccc2s1] | N-((1S)-1-{[(1S,4S)-5-(1-benzothien-2-ylacetyl)-2,5-diazabicyclo[2.2.1]hept-2-yl]carbonyl}-2,2-dimethylpropyl)-1H-indole-2-carboxamide | 529.2 |
| 39 | 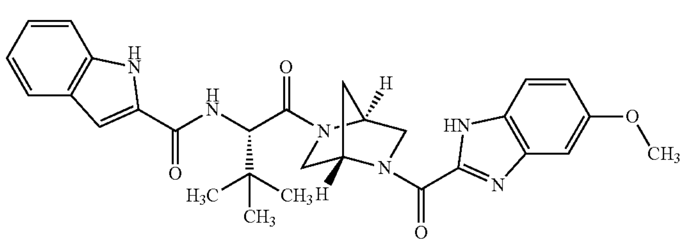 [SMILES: COc1ccc2[nH]c(C(=O)N3C[C@@H]4C[C@H]3CN4C(=O)[C@@H](NC(=O)c3cc4ccccc4[nH]3)C(C)(C)C)nc2c1] | N-{(1S)-2,2-dimethyl-1-[((1S,4S)-5-{[5-(methyloxy)-1H-benzimidazol-2-yl]carbonyl}-2,5-diazabicyclo[2.2.1]hept-2-yl)carbonyl]propyl}-1H-indole-2-carboxamide | 529.2 |

TABLE 1-continued

| Ex # | Structure | Name | LCMS [M + 1]+ |
|---|---|---|---|
| 40 | 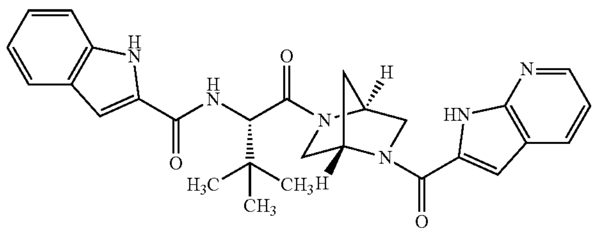 [SMILES: CC(C)(C)[C@H](NC(=O)c1cc2ccccc2[nH]1)C(=O)N1C[C@@H]2C[C@H]1CN2C(=O)c1cc2cccnc2[nH]1] | N-((1S)-2,2-dimethyl-1-{[(1S,4S)-5-(1H-pyrrolo[2,3-b]pyridin-2-ylcarbonyl)-2,5-diazabicyclo[2.2.1]hept-2-yl]carbonyl}propyl)-1H-indole-2-carboxamide | 499.2 |
| 41 | 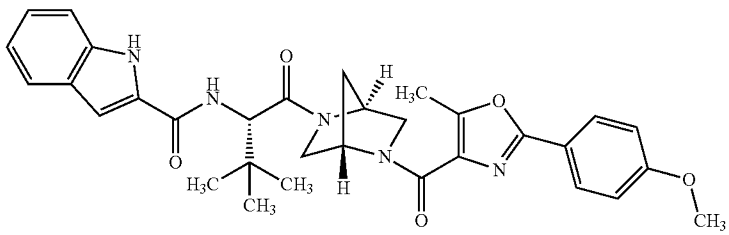 [SMILES: COc1ccc(-c2nc(C(=O)N3C[C@@H]4C[C@H]3CN4C(=O)[C@@H](NC(=O)c3cc4ccccc4[nH]3)C(C)(C)C)c(C)o2)cc1] | N-((1S)-2,2-dimethyl-1-{[(1S,4S)-5-({5-methyl-2-[4-(methyloxy)phenyl]-1,3-oxazol-4-yl}carbonyl)-2,5-diazabicyclo[2.2.1]hept-2-yl]carbonyl}propyl)-1H-indole-2-carboxamide | 570.2 |
| 42 | 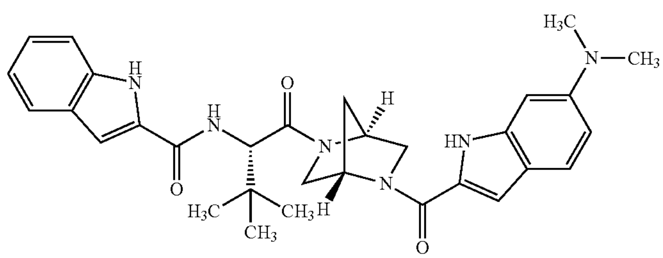 [SMILES: CN(C)c1ccc2cc(C(=O)N3C[C@@H]4C[C@H]3CN4C(=O)[C@@H](NC(=O)c3cc4ccccc4[nH]3)C(C)(C)C)[nH]c2c1] | N-{(1S)-1-[((1S,4S)-5-{[6-(dimethylamino)-1H-indol-2-yl]carbonyl}-2,5-diazabicyclo[2.2.1]hept-2-yl)carbonyl]-2,2-dimethylpropyl}-1H-indole-2-carboxamide | 541.3 |
| 43 | 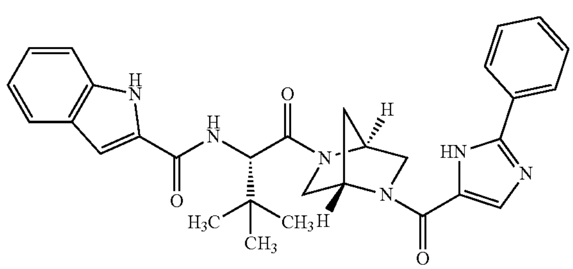 [SMILES: CC(C)(C)[C@H](NC(=O)c1cc2ccccc2[nH]1)C(=O)N1C[C@@H]2C[C@H]1CN2C(=O)c1cnc(-c2ccccc2)[nH]1] | N-[(1S)-2,2-dimethyl-1-({(1S,4S)-5-[(2-phenyl-1H-imidazol-4-yl)carbonyl]-2,5-diazabicyclo[2.2.1]hept-2-yl}carbonyl)propyl]-1H-indole-2-carboxamide | 525.3 |
| 44 | 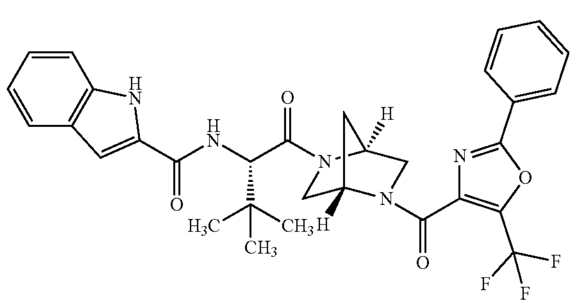 [SMILES: CC(C)(C)[C@H](NC(=O)c1cc2ccccc2[nH]1)C(=O)N1C[C@@H]2C[C@H]1CN2C(=O)c1nc(-c2ccccc2)oc1C(F)(F)F] | N-{(1S)-2,2-dimethyl-1-[((1S,4S)-5-{[2-phenyl-5-(trifluoromethyl)-1,3-oxazol-4-yl]carbonyl}-2,5-diazabicyclo[2.2.1]hept-2-yl)carbonyl]propyl}-1H-indole-2-carboxamide | 594.2 |

Example 45

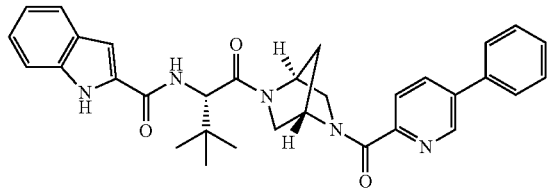 [SMILES: CC(C)(C)[C@H](NC(=O)c1cc2ccccc2[nH]1)C(=O)N1C[C@@H]2C[C@H]1CN2C(=O)c1ccc(-c2ccccc2)cn1]

N-[(1S)-(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide

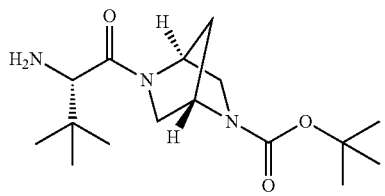 [SMILES: CC(C)(C)OC(=O)N1C[C@@H]2C[C@H]1CN2C(=O)[C@@H](N)C(C)(C)C]

1,1-Dimethylethyl (1S,4S)-5-(3-methyl-L-valyl)-2,5-diazabicyclo[2.2.1]heptane-2-carboxylate To a solution of 1,1-dimethylethyl (1S,4S)-2,5-diazabicyclo[2.2.1]heptane-2-carboxylate (11.25 g, 57.6 mmol) in $CH_2Cl_2$ (567 mL) was added EDC (40.8 g, 213 mmol), HOBt (10.86 g, 70.9 mmol), 3-methyl-N-{[(phenylmethyl)oxy]carbonyl}-L-valine (18.82 g, 70.9 mmol), and NMM (37.4 g, 340 mmol). The reaction mixture was stirred at room temperature for 18 h. The reaction was diluted with water (75 ml) and sat. $Na_2CO_3$ (75 ml). Stirring was continued for an additional 0.5 h then the two layers were separated. The organic solution was washed with sat. $NaHCO_3$, 1N HCl, sat. $NaHCO_3$, and brine. The organic layer was passed over a phase separator and concentrated under reduced pressure. To the residue was added ethanol (567 ml), 10% Pd/C (6.04 g) and ammonium formate (35.8 g, 567 mmol). The solution was stirred at room temperature for 18 h and then filtered over a pad of celite. The resulting solution was concentrated to afford an off white residue. The residue was dissolved in $CH_2Cl_2$ and washed with sat. $Na_2CO_3$. The layers were separated and the aqueous layer was extracted three times with $CH_2Cl_2$. The combined $CH_2Cl_2$ extracts were passed over a phase separator and concentrated to afford the desired product (17.1 g, 54.9 mmol) as an off white residue. LCMS (m/z): 312.2 (M+H).

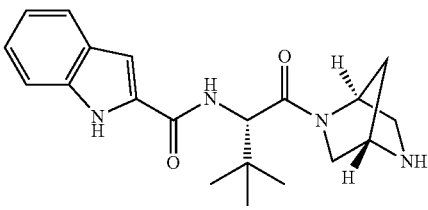 [SMILES: CC(C)(C)[C@H](NC(=O)c1cc2ccccc2[nH]1)C(=O)N1C[C@@H]2C[C@H]1CN2]

N-{(1S)-1-[(1S,4S)-2,5-diazabicyclo[2.2.1]hept-2-ylcarbonyl]-2,2-dimethylpropyl}-1H-indole-2-carboxamide To a 500 ml flask was added 1,1-dimethylethyl (1S,4S)-5-(3-methyl-L-valyl)-2,5-diazabicyclo[2.2.1]heptane-2-carboxylate (17.1 g, 54.9 mmol), 1H-indole-2-carboxylic acid (10.62 g, 65.9 mmol), HOBt (10.09 g, 65.9 mmol) and EDC (25.3 g, 132 mmol) followed by $CH_2Cl_2$ (366 ml) and NMM (24.15 ml, 220 mmol). The mixture was stirred for 18 h. The reaction was diluted with water (150 ml) and sat. $Na_2CO_3$ (150 ml). Stirring was continued for an additional 0.5 h then the two layers were separated. The organic solution was washed with sat. $NaHCO_3$, 1N HCl, sat. $NaHCO_3$, and brine. The organic layer was passed over a phase separator and concentrated under reduced pressure. The residue was dissolved in $CH_2Cl_2$ (100 ml). To the solution was added TFA (25 ml, 324 mmol). Stirring continued for 2 h then the solution was concentrated under reduced pressure. The resulting residue was dissolved in $CH_2Cl_2$ then washed twice with 2N HCl. The acidic solution was made basic and extracted with $CH_2Cl_2$. The organics were dried and concentrated to afford a brown residue. The residue was purified by reverse phase chromatography on a Biotage SP4 with a 65i column at a flow rate of 65 ml/min, 0.1% TFA eluting with 3 CV water, the 0-50% ACN/Water over 10 CV. The fractions containing the product were combined and diluted with $CH_2Cl_2$ and sat. $NaHCO_3$. The layers were separated and the resulting aqueous layer was saturated with NaCl and extracted three times with $CH_2Cl_2$. The combined $CH_2Cl_2$ extracts were combined, dried and concentrated to afford the desired product (10 g, 28.2 mmol) as an off white solid. LCMS (m/z): 355.2 (M+H).

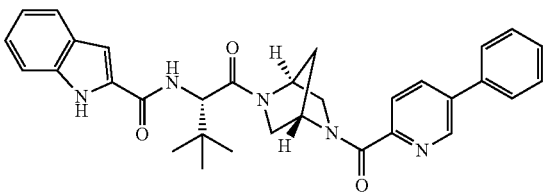 [SMILES: CC(C)(C)[C@H](NC(=O)c1cc2ccccc2[nH]1)C(=O)N1C[C@@H]2C[C@H]1CN2C(=O)c1ccc(-c2ccccc2)cn1]

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide To a 10 ml vial was added N-{(1S)-1-[(1S,4S)-2,5-diazabicyclo[2.2.1]hept-2-ylcarbonyl]-2,2-dimethylpropyl}-1H-indole-2-carboxamide (100 mg, 0.268 mmol), EDC (128 mg, 0.670 mmol), HOBt (41.0 mg, 0.268 mmol), 5-phenyl-2-pyridinecarboxylic acid (64.1 mg, 0.322 mmol), CH$_2$Cl$_2$ (2.8 ml) and DIEA (0.187 ml, 1.072 mmol). The mixture was stirred at room temperature for 4 h, then diluted with sat. Na$_2$CO$_3$. The organic layer was passed over a phase separator and concentrated and purified by reverse phase HPLC: 30×75 mm sunfire column 50 ml/min, 0.1% TFA, 20-60% ACN/Water over 14 min. The fractions containing the product were combined and diluted with CH$_2$Cl$_2$ and sat. NaHCO$_3$. The layers were separated and the resulting aqueous layer was extracted three times with CH$_2$Cl$_2$. The combined CH$_2$Cl$_2$ extracts were combined, dried and concentrated to afford the desired product (123 mg, 0.227 mmol) as an off white solid. LCMS (m/z): 536.2 (M+H). 1H NMR (400 MHz, DMSO-d$_6$) δ ppm 0.99 (s, 1H), 1.05 (s, 2H), 1.07 (s, 2H), 1.10 (s, 4H), 1.73-2.09 (m, 2H), 3.37-4.07 (m, 4H), 4.45-5.27 (m, 3H), 6.90-7.25 (m, 2H), 7.26-7.96 (m, 9H), 8.03-8.38 (m, 2H), 8.42-9.10 (m, 1H), 11.55-11.83 (m, 1H)

Examples 46-52

The compounds in Table 2 were prepared by a method similar to the one described for the preparation of N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide (Example 45). As is appreciated by those skilled in the art, these analogous examples may involve variations in general reaction conditions.

TABLE 2

| Ex # | Structure | Name | LCMS [M + 1]$^+$ |
|---|---|---|---|
| 46 | 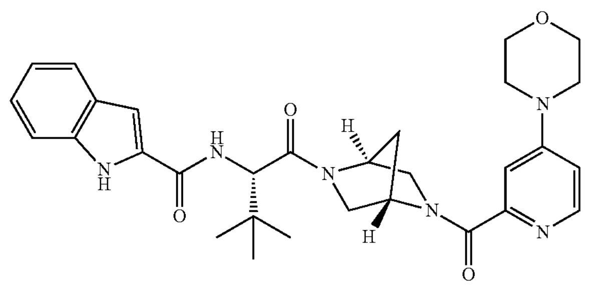 [SMILES: CC(C)(C)[C@H](NC(=O)c1cc2ccccc2[nH]1)C(=O)N1C[C@@H]2C[C@H]1CN2C(=O)c1cc(N2CCOCC2)ccn1] | N-{(1S)-2,2-dimethyl-1-[((1S,4S)-5-{[4-(4-morpholinyl)-2-pyridinyl]carbonyl}-2,5-diazabicyclo[2.2.1]hept-2-yl)carbonyl]propyl}-1H-indole-2-carboxamide | 545.3 |
| 47 | 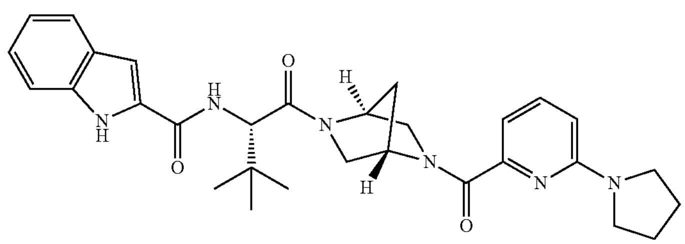 [SMILES: CC(C)(C)[C@H](NC(=O)c1cc2ccccc2[nH]1)C(=O)N1C[C@@H]2C[C@H]1CN2C(=O)c1cccc(N2CCCC2)n1] | N-{(1S)-2,2-dimethyl-1-[((1S,4S)-5-{[6-(1-pyrrolidinyl)-2-pyridinyl]carbonyl}-2,5-diazabicyclo[2.2.1]hept-2-yl)carbonyl]propyl}-1H-indole-2-carboxamide | 529.3 |
| 48 | 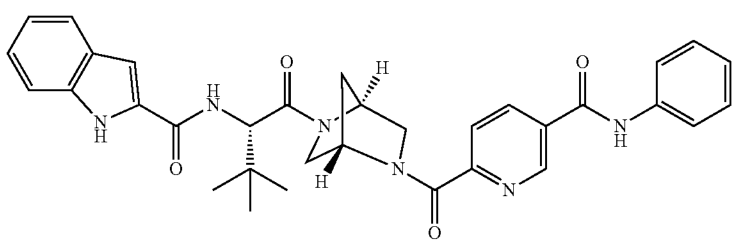 [SMILES: CC(C)(C)[C@H](NC(=O)c1cc2ccccc2[nH]1)C(=O)N1C[C@@H]2C[C@H]1CN2C(=O)c1ccc(C(=O)Nc2ccccc2)cn1] | N-((1S)-2,2-dimethyl-1-{[(1S,4S)-5-({5-[(phenylamino)carbonyl]-2-pyridinyl}carbonyl)-2,5-diazabicyclo[2.2.1]hept-2-yl]carbonyl}propyl)-1H-indole-2-carboxamide | 579.2 |
| 49 | 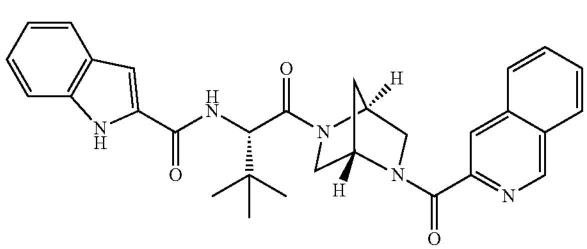 [SMILES: CC(C)(C)[C@H](NC(=O)c1cc2ccccc2[nH]1)C(=O)N1C[C@@H]2C[C@H]1CN2C(=O)c1cc2ccccc2cn1] | N-((1S)-1-{[(1S,4S)-5-(3-isoquinolinylcarbonyl)-2,5-diazabicyclo[2.2.1]hept-2-yl]carbonyl}-2,2-dimethylpropyl)-1H-indole-2-carboxamide | 510.2 |

TABLE 2-continued

| Ex # | Structure | Name | LCMS [M + 1]+ |
|---|---|---|---|
| 50 | 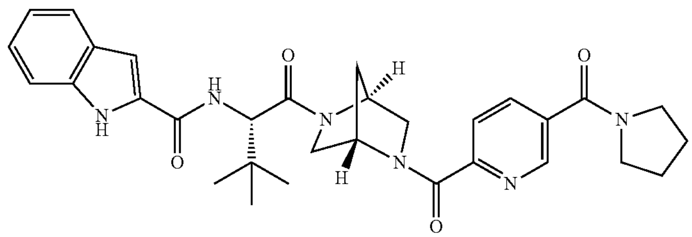 [SMILES: CC(C)(C)[C@H](NC(=O)c1cc2ccccc2[nH]1)C(=O)N1C[C@@H]2C[C@H]1CN2C(=O)c1ccc(C(=O)N2CCCC2)cn1] | N-{(1S)-2,2-dimethyl-1-[((1S,4S)-5-{[5-(1-pyrrolidinylcarbonyl)-2-pyridinyl]carbonyl}-2,5-diazabicyclo[2.2.1]hept-2-yl)carbonyl]propyl}-1H-indole-2-carboxamide | 557.3 |
| 51 | 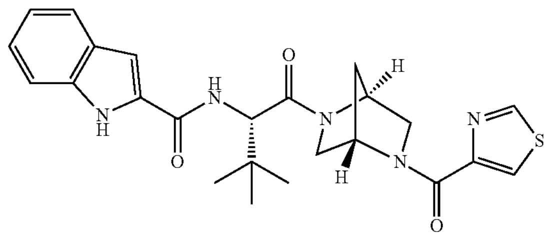 [SMILES: CC(C)(C)[C@H](NC(=O)c1cc2ccccc2[nH]1)C(=O)N1C[C@@H]2C[C@H]1CN2C(=O)c1cscn1] | N-((1S)-2,2-dimethyl-1-{[(1S,4S)-5-(1,3-thiazol-4-ylcarbonyl)-2,5-diazabicyclo[2.2.1]hept-2-yl]carbonyl}propyl)-1H-indole-2-carboxamide | 466.1 |
| 52 | 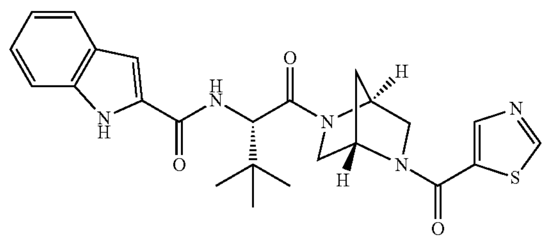 [SMILES: CC(C)(C)[C@H](NC(=O)c1cc2ccccc2[nH]1)C(=O)N1C[C@@H]2C[C@H]1CN2C(=O)c1cncs1] | N-((1S)-2,2-dimethyl-1-{[(1S,4S)-5-(1,3-thiazol-5-ylcarbonyl)-2,5-diazabicyclo[2.2.1]hept-2-yl]carbonyl}propyl)-1H-indole-2-carboxamide | 466.2 |

Examples 53-55

The compounds in Table 3 were prepared by a method similar to the one described for the preparation of N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide (Example 1). As is appreciated by those skilled in the art, these analogous examples may involve variations in general reaction conditions. 5-(4-pyridinyl)-1H-indole-2-carboxylic acid (Intermediate 1) was used for the preparation of Example 55 and its synthesis is described below.

TABLE 3

| Ex # | Structure | Name | LCMS [M + 1]+ |
|---|---|---|---|
| 53 | 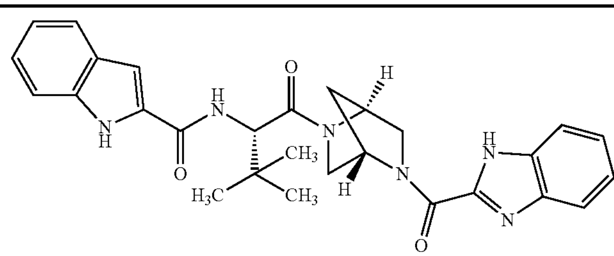 | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1H-indole-2-carboxamide | 499.4 |
| 54 | 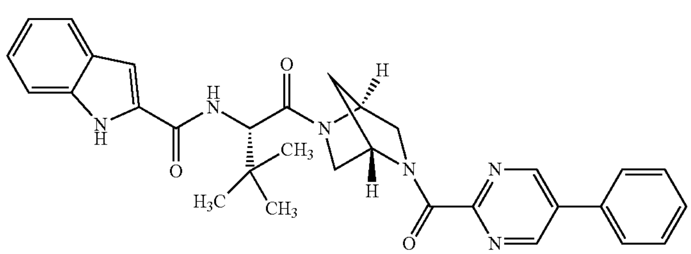 [SMILES: CC(C)(C)[C@H](NC(=O)c1cc2ccccc2[nH]1)C(=O)N1C[C@@H]2C[C@H]1CN2C(=O)c1ncc(-c2ccccc2)cn1] | N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-1H-indole-2-carboxamide | 537.3 |

| Ex # | Structure | Name | LCMS [M + 1]+ |
|---|---|---|---|
| 55 | 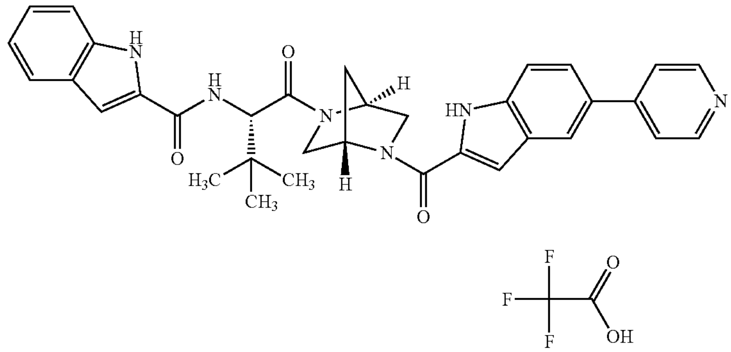 [SMILES: CC(C)(C)[C@H](NC(=O)c1cc2ccccc2[nH]1)C(=O)N1C[C@@H]2C[C@H]1CN2C(=O)c1cc2cc(-c3ccncc3)ccc2[nH]1 ; O=C(O)C(F)(F)F] | N-{(1S)-2,2-dimethyl-1-[((1S,4S)-5-{[5-(4-pyridinyl)-1H-indol-2-yl]carbonyl}-2,5-diazabicyclo[2.2.1]hept-2-yl)carbonyl]propyl}-1H-indole-2-carboxamide trifluoroacetate | 575.3 |

Intermediate 1

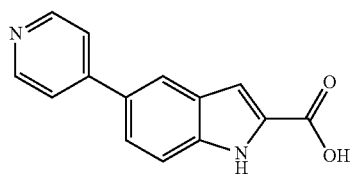 [SMILES: O=C(O)c1cc2cc(-c3ccncc3)ccc2[nH]1]

5-(4-Pyridinyl)-1H-indole-2-carboxylic acid

A solution of 5-bromo-1H-indole-2-carboxylic acid (25 mg), PdCl₂HPNor₂ (5 mg), K₃PO4 (45 mg), 4-pyridylboronic acid (26 mg), dioxane (1 mL) and H₂O (1 mL) was heated to 170° C. in a microwave for 2 h. The solution was passed thru a C18-SPE cartridge eluting with 3, 20, 60, and finally 95% CH₃CN in H₂O to yield the crude product. LCMS (m/z): 239.1 (M+H).

Example 56

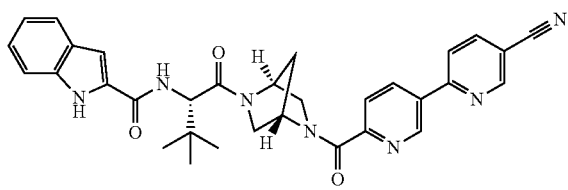 [SMILES: CC(C)(C)[C@H](NC(=O)c1cc2ccccc2[nH]1)C(=O)N1C[C@@H]2C[C@H]1CN2C(=O)c1ccc(-c2ccc(C#N)cn2)cn1]

N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide

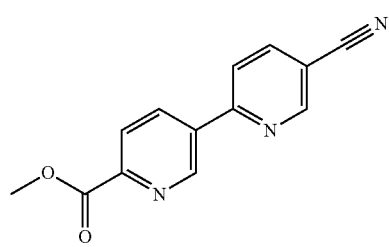 [SMILES: COC(=O)c1ccc(-c2ccc(C#N)cn2)cn1]

Methyl 5-cyano-2,3'-bipyridine-6'-carboxylate

To a microwave vial was added methyl 5-(4,4,5,5-tetramethyl-1,3,2-dioxaborolan-2-yl)-2-pyridinecarboxylate (2 g, 7.60 mmol), 6-bromo-3-pyridinecarbonitrile (2.09 g, 11.40 mmol), PdCl₂(dppf)-CH₂Cl₂ adduct (0.62 g, 0.760 mmol), NaHCO₃ (1.277 g, 15.20 mmol), 1,4-dioxane (8 ml) and water (2 ml). The mixture was microwaved for 15 min at 105° C. The resulting dark solution was diluted with water and CH₂Cl₂. The aqueous layer was extracted three times with CH₂Cl₂. The CH₂Cl₂ extracts were passed over a phase separator, concentrated and purified on a Biotage SP4 with a 65i column at a flow rate of 65 ml/min, 0.1% TFA eluting with 2CV water, the 0-100% ACN/Water over 10 CV. The fractions containing the product were combined and diluted with CH₂Cl₂ and sat. NaHCO₃. The layers were separated and the aqueous layer was extracted twice with CH₂Cl₂, then the combined organic extracts were dried and concentrated to afford the desired product (1.0 g, 1.75 mmol) as an off white solid. LCMS (m/z): 262.0 (M+Na).

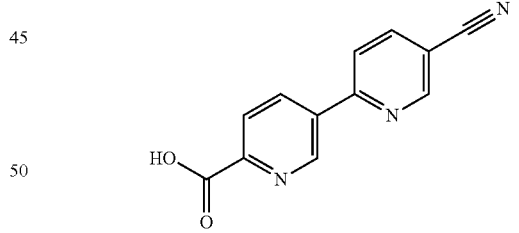

5-Cyano-2,3'-bipyridine-6'-carboxylic acid

To a 250 ml flask was added methyl 5-cyano-2,3'-bipyridine-6'-carboxylate (950 mg, 3.57 mmol), water (9.5 ml), tetrahydrofuran (38.4 ml) and LiOH (86 mg, 3.57 mmol). The mixture was stirred for 30 min, diluted with tetrahydrofuran (200 ml) and cooled to 0° C. (ice water batch). After an additional 30 min, the resulting suspension was filtered, washed with THF and dried under reduced pressure to afford the desired product as a light brown powder. LCMS (m/z): 226.1 (M+H).

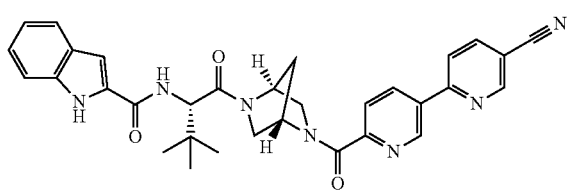 [SMILES: CC(C)(C)[C@H](NC(=O)c1cc2ccccc2[nH]1)C(=O)N1C[C@@H]2C[C@H]1CN2C(=O)c1ccc(-c2ccc(C#N)cn2)cn1]

N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide To a 10 ml vial was added N-{(1S)-1-[(1S,4S)-2,5-diazabicyclo[2.2.1]hept-2-ylcarbonyl]-2,2-dimethylpropyl}-1H-indole-2-carboxamide (100 mg, 0.268 mmol), EDC (128 mg, 0.670 mmol), HOBt (41.0 mg, 0.268 mmol), 5-cyano-2,3'-bipyridine-6'-carboxylic acid (74.7 mg, 0.322 mmol) mmol), $CH_2Cl_2$ (2.8 ml), DMF (5.0 ml) and DIEA (0.187 ml, 1.072 mmol). The mixture was stirred at room temperature for 1 h, then at 60° C. for 3 h. After cooling to room temperature, the mixture was diluted with $CH_2Cl_2$ and sat. $Na_2CO_3$. The organic layer was passed over a phase separator, concentrated and purified by reverse phase HPLC: 30×75 mm sunfire column 50 ml/min, 0.1% TFA, 20-60% ACN/Water over 14 min. The fractions containing the product were combined and diluted with $CH_2Cl_2$ and sat. $NaHCO_3$. The organic layer was separated, passed over a phase separator and concentrated to afford the desired product as an off white solid (75 mg, 0.132 mmol) as an off white solid. LCMS (m/z): 562.3 (M+H). 1H NMR (400 MHz, DMSO-$d_6$) δ ppm 0.99 (s, 1H), 1.02-1.07 (m, 4H), 1.10 (s, 4H), 1.74-2.12 (m, 2H), 3.37-4.10 (m, 4H), 4.25-5.26 (m, 3H), 6.82-7.68 (m, 5H), 7.87-7.79 (m, 5H), 8.85-9.52 (m, 2H), 11.44-11.92 (m, 1H).

Examples 57-58

The compounds in Table 4 were prepared by a method similar to the one described for the preparation of N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide (Example 56). As is appreciated by those skilled in the art, these analogous examples may involve variations in general reaction conditions.

TABLE 4

| Ex # | Structure | Name | LCMS [M + 1]+ |
|---|---|---|---|
| 57 | 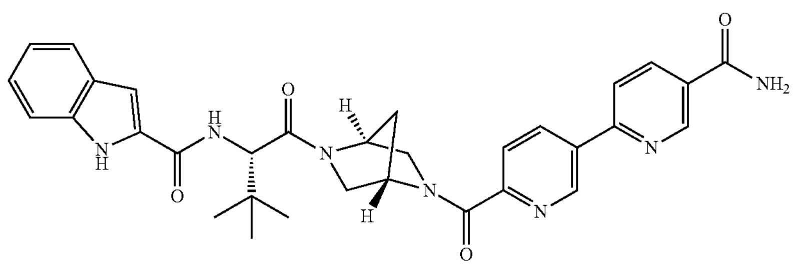 [SMILES: CC(C)(C)[C@H](NC(=O)c1cc2ccccc2[nH]1)C(=O)N1C[C@@H]2C[C@H]1CN2C(=O)c1ccc(-c2ccc(C(N)=O)cn2)cn1] | 6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxamide | 580.3 |
| 58 | 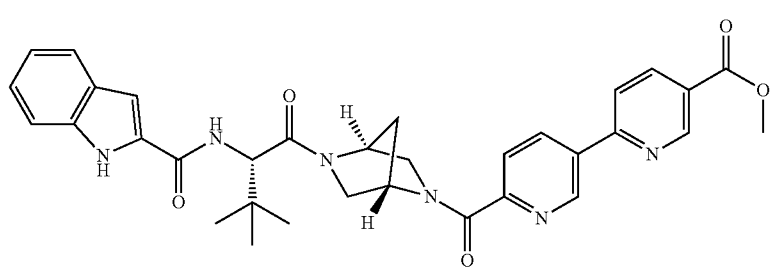 [SMILES: COC(=O)c1ccc(-c2ccc(C(=O)N3C[C@@H]4C[C@H]3CN4C(=O)[C@@H](NC(=O)c3cc4ccccc4[nH]3)C(C)(C)C)nc2)nc1] | methyl 6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxylate | 595.2 |

Example 59

N-{(1S)-2,2-dimethyl-1-[((1S,4S)-5-{[5-(1H-tetrazol-5-yl)-2,3'-bipyridin-6'-yl]carbonyl}-2,5-diazabicyclo[2.2.1]hept-2-yl)carbonyl]propyl}-1H-indole-2-carboxamide

N-{(1S)-1-[((1S,4S)-5-{[5-(4-cyanophenyl)-2-pyridinyl]carbonyl}-2,5-diazabicyclo[2.2.1]hept-2-yl)carbonyl]-2,2-dimethylpropyl}-1H-indole-2-carboxamide To a 200 ml flask was added 5-(4-cyanophenyl)-2-pyridinecarboxylic acid (0.76 g, 3.39 mmol), N-{(1S)-1-[(1S,4S)-2,

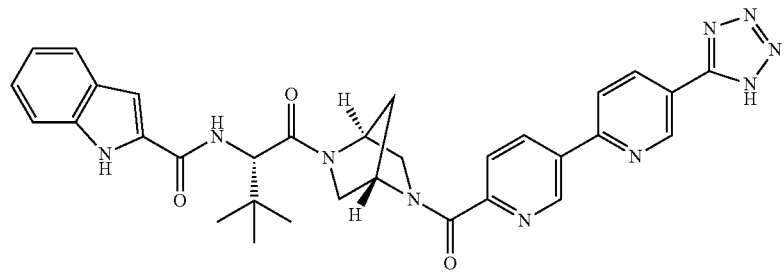 [SMILES: CC(C)(C)[C@H](NC(=O)c1cc2ccccc2[nH]1)C(=O)N1C[C@@H]2C[C@H]1CN2C(=O)c1ccc(-c2ccc(-c3nnn[nH]3)cn2)cn1]

To a 3 mL vial was added N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide (0.125 g, 0.120 mmol, contaminated with some methyl 6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxylate). Next N,N-dimethylformamide (1 mL) and toluene (1 mL) were added, followed by triethylamine hydrochloride (24.82 mg, 0.180 mmol) and sodium azide (11.72 mg, 0.180 mmol). The mixture was heated to 80° C. for 5 h, then 50° C. overnight. The next day the mixture was concentrated to remove the toluene and purified via reverse phase HPLC (20-60% CH$_3$CN/Water over 14 min). The fractions containing product were concentrated and combined to afford N-{(1S)-2,2-dimethyl-1-[(((1S,4S)-5-{[5-(1H-tetrazol-5-yl)-2,3'-bipyridin-6'-yl]carbonyl}-2,5-diazabicyclo[2.2.1]hept-2-yl)carbonyl]propyl}-1H-indole-2-carboxamide (0.050 g, 65% yield) as an off white solid. LCMS (m/z): 605.3 (M+H).

Example 60

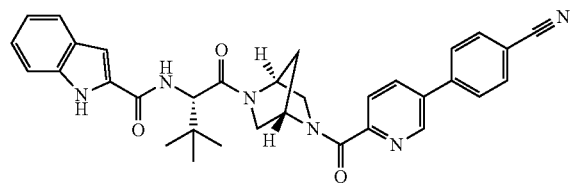 [SMILES: CC(C)(C)[C@H](NC(=O)c1cc2ccccc2[nH]1)C(=O)N1C[C@@H]2C[C@H]1CN2C(=O)c1ccc(-c2ccc(C#N)cc2)cn1]

5-diazabicyclo[2.2.1]hept-2-ylcarbonyl]-2,2-dimethylpropyl}-1H-indole-2-carboxamide (1 g, 2.82 mmol), EDC (1.30 g, 6.77 mmol), HOBt (0.52 g, 3.39 mmol), CH$_2$Cl$_2$ (28 ml), DIEA (1.971 ml, 11.29 mmol). The mixture was stirred at room temperature overnight then diluted with CH$_2$Cl$_2$, water and sat. Na$_2$CO$_3$. The two layers were separated and the organic washed with 2N HCl, sat. NaHCO$_3$ and brine. The CH$_2$Cl$_2$ was passed over a phase separator and concentrated to afford a brown residue. The residue was purified by reverse phase chromatography on a Biotage SP4 with a 65i column at a flow rate of 65 ml/min, 0.1% TFA eluting with 2CV water, the 0-100% ACN/Water over 20 CV. The fractions containing the product were combined and diluted with CH$_2$Cl$_2$ and sat. NaHCO$_3$. The layers were separated and the CH$_2$Cl$_2$ was dried and concentrated to afford the desired product (1.0 g, 1.75 mmol) as an off white solid. LCMS (m/z): 561.3 (M+H). 1H NMR (400 MHz, DMSO-d$_6$) δ ppm 0.99 (s, 1H), 1.02-1.07 (m, 4H), 1.10 (s, 4H), 1.74-2.12 (m, 2H), 3.37-4.03 (m, 4H), 4.55-5.26 (m, 3H), 6.87-7.24 (m, 2H), 7.26-7.68 (m, 3H), 7.78-8.41 (m, 7H), 8.48-9.18 (m, 1H), 11.52-11.87 (m, 1H).

Examples 61-130

The compounds in Table 5 were prepared by a method similar to the one described for the preparation of N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide (Example 1). As is appreciated by those skilled in the art, these analogous examples may involve variations in general reaction conditions.

TABLE 5

| Ex # | Structure | Name | LCMS [M + 1]+ |
|---|---|---|---|
| 61 | 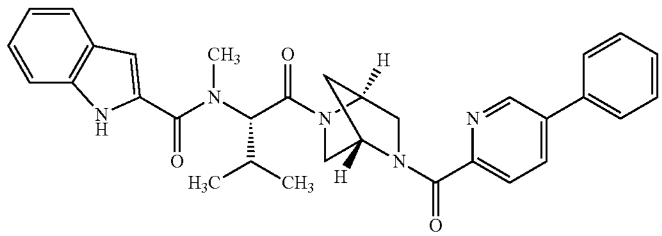 [SMILES: CC(C)[C@@H](C(=O)N1C[C@@H]2C[C@H]1CN2C(=O)c1ccc(-c2ccccc2)cn1)N(C)C(=O)c1cc2ccccc2[nH]1] | N-methyl-N-[(1S)-2-methyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide | 536.3 |
| 62 | 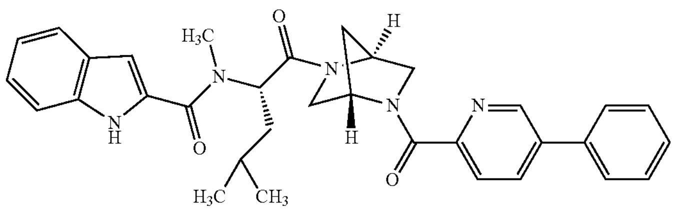 [SMILES: CC(C)C[C@@H](C(=O)N1C[C@@H]2C[C@H]1CN2C(=O)c1ccc(-c2ccccc2)cn1)N(C)C(=O)c1cc2ccccc2[nH]1] | N-methyl-N-[(1S)-3-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide | 550.3 |
| 63 | 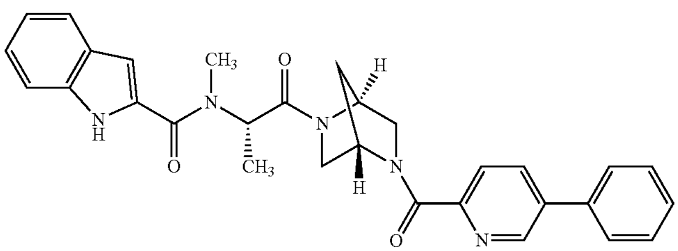 [SMILES: C[C@@H](C(=O)N1C[C@@H]2C[C@H]1CN2C(=O)c1ccc(-c2ccccc2)cn1)N(C)C(=O)c1cc2ccccc2[nH]1] | N-methyl-N-((1S)-1-methyl-2-oxo-2-{(1S,4S)-5-[(5-phenyl-2-pyridinyl)carbonyl]-2,5-diazabicyclo[2.2.1]hept-2-yl}ethyl)-1H-indole-2-carboxamide | 508.2 |
| 64 | 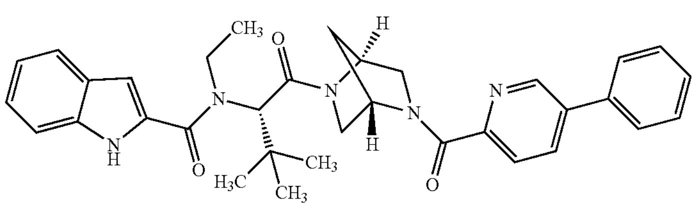 [SMILES: CCN(C(=O)c1cc2ccccc2[nH]1)[C@H](C(=O)N1C[C@@H]2C[C@H]1CN2C(=O)c1ccc(-c2ccccc2)cn1)C(C)(C)C] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-ethyl-1H-indole-2-carboxamide | 564.5 |
| 65 | 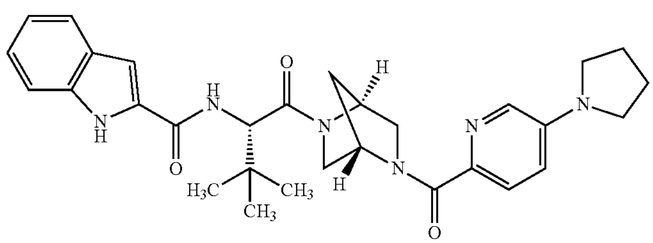 [SMILES: CC(C)(C)[C@H](NC(=O)c1cc2ccccc2[nH]1)C(=O)N1C[C@@H]2C[C@H]1CN2C(=O)c1ccc(N2CCCC2)cn1] | N-{(1S)-2,2-dimethyl-1-[((1S,4S)-5-{[5-(1-pyrrolidinyl)-2-pyridinyl]carbonyl}-2,5-diazabicyclo[2.2.1]hept-2-yl)carbonyl]propyl}-1H-indole-2-carboxamide | 529.1 |
| 66 | 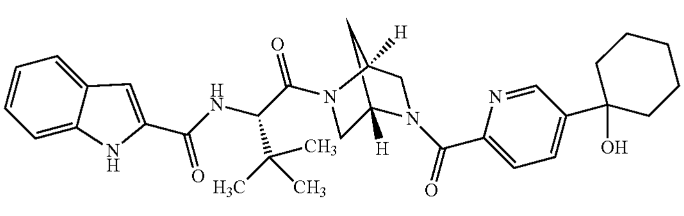 | N-{(1S)-1-[((1S,4S)-5-{[5-(1-hydroxycyclohexyl)-2-pyridinyl]carbonyl}-2,5-diazabicyclo[2.2.1]hept-2-yl)carbonyl]-2,2-dimethylpropyl}-1H-indole-2-carboxamide | 558.2 |

TABLE 5-continued

| Ex # | Structure | Name | LCMS [M + 1]+ |
|---|---|---|---|
| 67 | 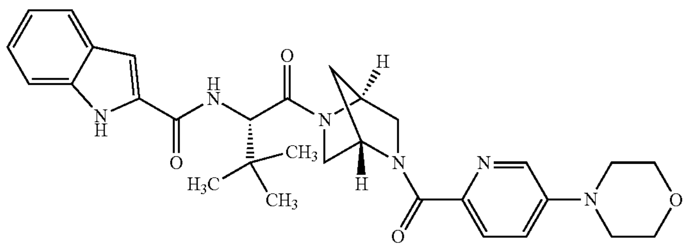 [SMILES: CC(C)(C)[C@H](NC(=O)c1cc2ccccc2[nH]1)C(=O)N1C[C@@H]2C[C@H]1CN2C(=O)c1ccc(N2CCOCC2)cn1] | N-{(1S)-2,2-dimethyl-1-[((1S,4S)-5-{[5-(4-morpholinyl)-2-pyridinyl]carbonyl}-2,5-diazabicyclo[2.2.1]hept-2-yl)carbonyl]propyl}-1H-indole-2-carboxamide | 545.3 |
| 68 | 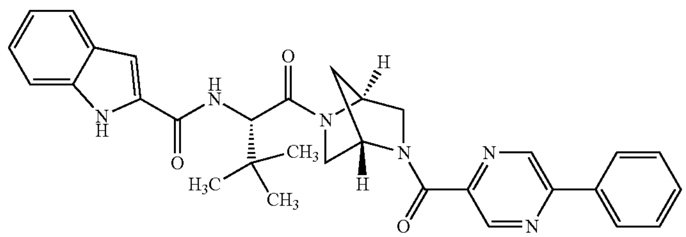 [SMILES: CC(C)(C)[C@H](NC(=O)c1cc2ccccc2[nH]1)C(=O)N1C[C@@H]2C[C@H]1CN2C(=O)c1cnc(-c2ccccc2)cn1] | N-[(1S)-2,2-dimethyl-1-({(1S,4S)-5-[(5-phenyl-2-pyrazinyl)carbonyl]-2,5-diazabicyclo[2.2.1]hept-2-yl}carbonyl)propyl]-1H-indole-2-carboxamide | 537.3 |
| 69 | 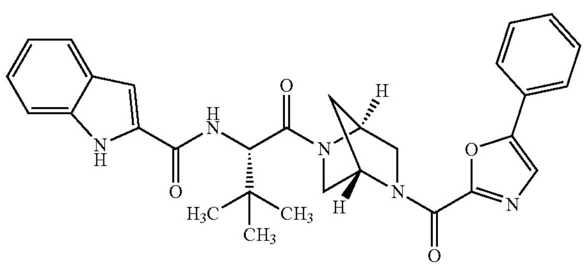 [SMILES: CC(C)(C)[C@H](NC(=O)c1cc2ccccc2[nH]1)C(=O)N1C[C@@H]2C[C@H]1CN2C(=O)c1ncc(-c2ccccc2)o1] | N-[(1S)-2,2-dimethyl-1-({(1S,4S)-5-[(5-phenyl-1,3-oxazol-2-yl)carbonyl]-2,5-diazabicyclo[2.2.1]hept-2-yl}carbonyl)propyl]-1H-indole-2-carboxamide | 526.3 |
| 70 | 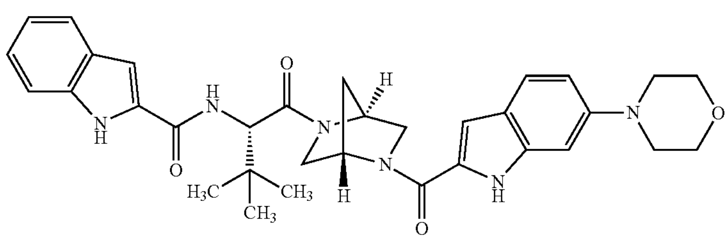 [SMILES: CC(C)(C)[C@H](NC(=O)c1cc2ccccc2[nH]1)C(=O)N1C[C@@H]2C[C@H]1CN2C(=O)c1cc2ccc(N3CCOCC3)cc2[nH]1] | N-{(1S)-2,2-dimethyl-1-[((1S,4S)-5-{[6-(4-morpholinyl)-1H-indol-2-yl]carbonyl}-2,5-diazabicyclo[2.2.1]hept-2-yl)carbonyl]propyl}-1H-indole-2-carboxamide | 583.3 |
| 71 | 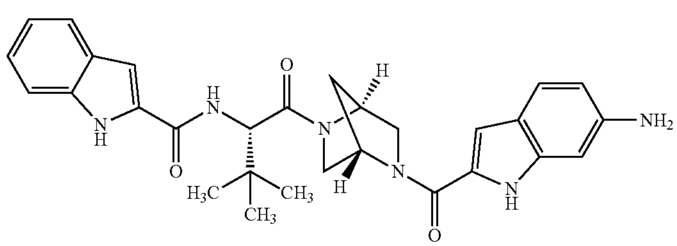 [SMILES: CC(C)(C)[C@H](NC(=O)c1cc2ccccc2[nH]1)C(=O)N1C[C@@H]2C[C@H]1CN2C(=O)c1cc2ccc(N)cc2[nH]1] | N-[(1S)-1-({(1S,4S)-5-[(6-amino-1H-indol-2-yl)carbonyl]-2,5-diazabicyclo[2.2.1]hept-2-yl}carbonyl)-2,2-dimethylpropyl]-1H-indole-2-carboxamide | 513.2 |
| 72 | 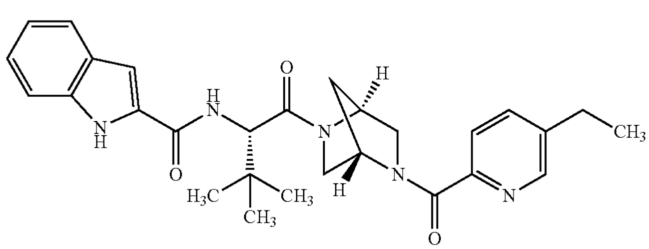 [SMILES: CCc1ccc(C(=O)N2C[C@@H]3C[C@H]2CN3C(=O)[C@@H](NC(=O)c2cc3ccccc3[nH]2)C(C)(C)C)nc1] | N-[(1S)-1-({(1S,4S)-5-[(5-ethyl-2-pyridinyl)carbonyl]-2,5-diazabicyclo[2.2.1]hept-2-yl}carbonyl)-2,2-dimethylpropyl]-1H-indole-2-carboxamide | 488.3 |

TABLE 5-continued

| Ex # | Structure | Name | LCMS [M + 1]+ |
|---|---|---|---|
| 73 | 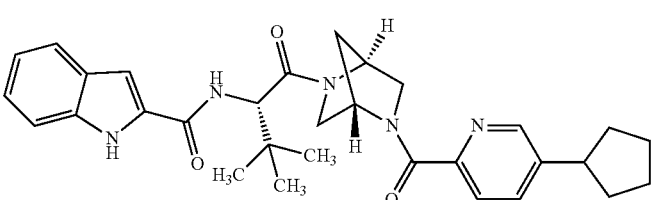 | N-[(1S)-1-({(1S,4S)-5-[(5-cyclopentyl-2-pyridinyl)carbonyl]-2,5-diazabicyclo[2.2.1]hept-2-yl}carbonyl)-2,2-dimethylpropyl]-1H-indole-2-carboxamide | 528.3 |
| 74 | 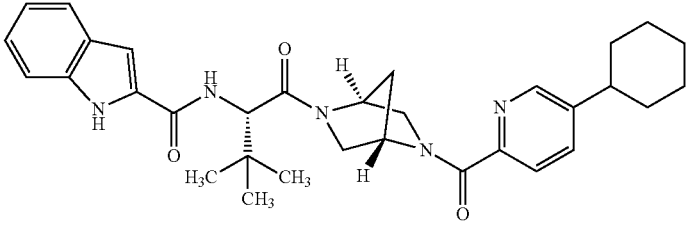 [SMILES: CC(C)(C)[C@H](NC(=O)c1cc2ccccc2[nH]1)C(=O)N1C[C@@H]2C[C@H]1CN2C(=O)c1ccc(C2CCCCC2)cn1] | N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide | 542.4 |
| 75 | 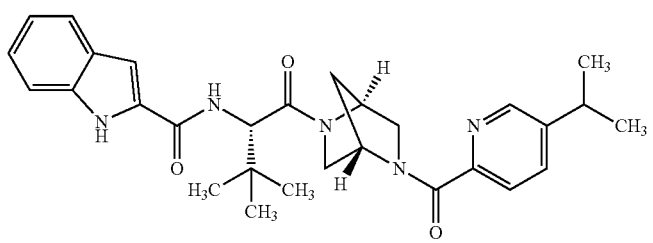 [SMILES: CC(C)c1ccc(C(=O)N2C[C@@H]3C[C@H]2CN3C(=O)[C@@H](NC(=O)c2cc3ccccc3[nH]2)C(C)(C)C)nc1] | N-{(1S)-2,2-dimethyl-1-[((1S,4S)-5-{[5-(1-methylethyl)-2-pyridinyl]carbonyl}-2,5-diazabicyclo[2.2.1]hept-2-yl)carbonyl]propyl}-1H-indole-2-carboxamide | 502.3 |
| 76 | 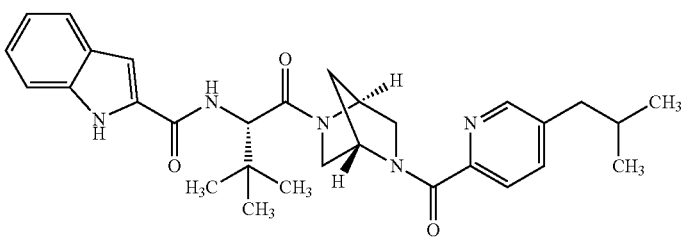 [SMILES: CC(C)Cc1ccc(C(=O)N2C[C@@H]3C[C@H]2CN3C(=O)[C@@H](NC(=O)c2cc3ccccc3[nH]2)C(C)(C)C)nc1] | N-{(1S)-2,2-dimethyl-1-[((1S,4S)-5-{[5-(2-methylpropyl)-2-pyridinyl]carbonyl}-2,5-diazabicyclo[2.2.1]hept-2-yl)carbonyl]propyl}-1H-indole-2-carboxamide | 516.3 |
| 77 | 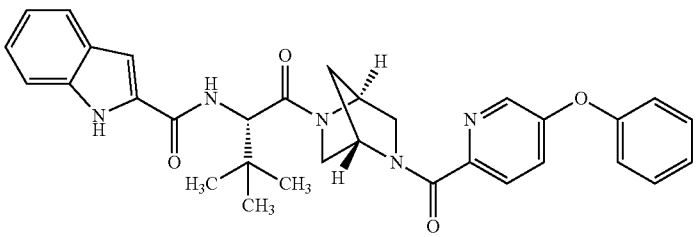 [SMILES: CC(C)(C)[C@H](NC(=O)c1cc2ccccc2[nH]1)C(=O)N1C[C@@H]2C[C@H]1CN2C(=O)c1ccc(Oc2ccccc2)cn1] | N-{(1S)-2,2-dimethyl-1-[((1S,4S)-5-{[5-(phenyloxy)-2-pyridinyl]carbonyl}-2,5-diazabicyclo[2.2.1]hept-2-yl)carbonyl]propyl}-1H-indole-2-carboxamide | 552.1 |
| 78 | 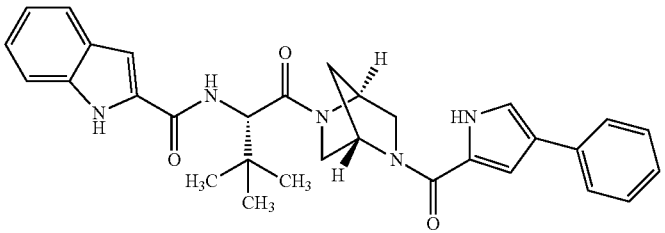 [SMILES: CC(C)(C)[C@H](NC(=O)c1cc2ccccc2[nH]1)C(=O)N1C[C@@H]2C[C@H]1CN2C(=O)c1cc(-c2ccccc2)c[nH]1] | N-[(1S)-2,2-dimethyl-1-({(1S,4S)-5-[(4-phenyl-1H-pyrrol-2-yl)carbonyl]-2,5-diazabicyclo[2.2.1]hept-2-yl}carbonyl)propyl]-1H-indole-2-carboxamide | 524.4 |

TABLE 5-continued

| Ex # | Structure | Name | LCMS [M + 1]+ |
|---|---|---|---|
| 79 | 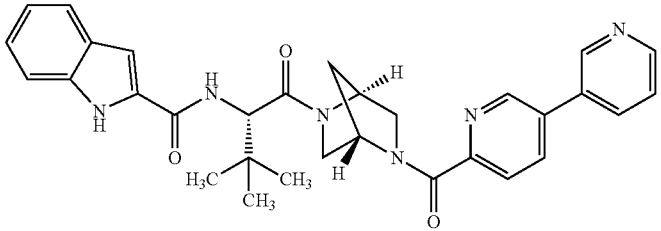 [SMILES: CC(C)(C)[C@H](NC(=O)c1cc2ccccc2[nH]1)C(=O)N1C[C@@H]2C[C@H]1CN2C(=O)c1ccc(-c2cccnc2)cn1] | N-((1S)-1-{[(1S,4S)-5-(3,3'-bipyridin-6-ylcarbonyl)-2,5-diazabicyclo[2.2.1]hept-2-yl]carbonyl}-2,2-dimethylpropyl)-1H-indole-2-carboxamide | 537.3 |
| 80 | 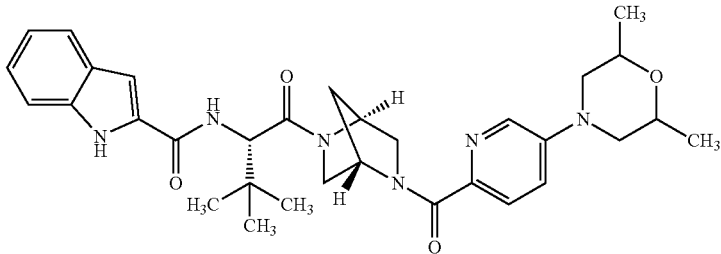 [SMILES: CC1CN(c2ccc(C(=O)N3C[C@@H]4C[C@H]3CN4C(=O)[C@@H](NC(=O)c3cc4ccccc4[nH]3)C(C)(C)C)nc2)CC(C)O1] | N-{(1S)-1-[((1S,4S)-5-{[5-(2,6-dimethyl-4-morpholinyl)-2-pyridinyl]carbonyl}-2,5-diazabicyclo[2.2.1]hept-2-yl)carbonyl]-2,2-dimethylpropyl}-1H-indole-2-carboxamide | 573.3 |
| 81 | 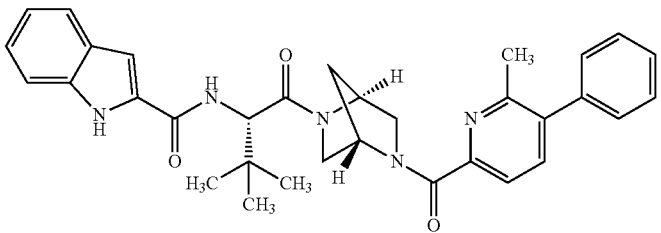 [SMILES: Cc1nc(C(=O)N2C[C@@H]3C[C@H]2CN3C(=O)[C@@H](NC(=O)c2cc3ccccc3[nH]2)C(C)(C)C)ccc1-c1ccccc1] | N-[(1S)-2,2-dimethyl-1-({(1S,4S)-5-[(6-methyl-5-phenyl-2-pyridinyl)carbonyl]-2,5-diazabicyclo[2.2.1]hept-2-yl}carbonyl)propyl]-1H-indole-2-carboxamide | 550.2 |
| 82 | 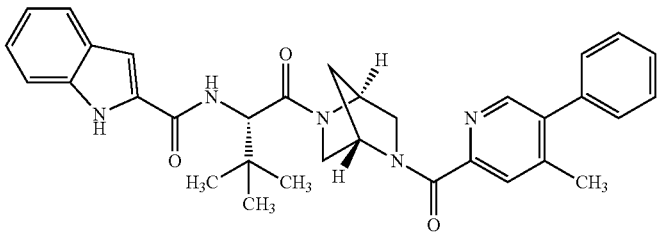 [SMILES: Cc1cc(C(=O)N2C[C@@H]3C[C@H]2CN3C(=O)[C@@H](NC(=O)c2cc3ccccc3[nH]2)C(C)(C)C)ncc1-c1ccccc1] | N-[(1S)-2,2-dimethyl-1-({(1S,4S)-5-[(4-methyl-5-phenyl-2-pyridinyl)carbonyl]-2,5-diazabicyclo[2.2.1]hept-2-yl}carbonyl)propyl]-1H-indole-2-carboxamide | 550.2 |
| 83 | 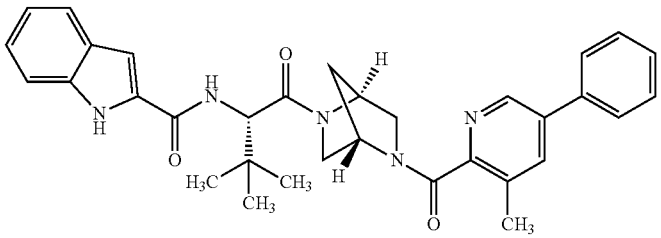 [SMILES: Cc1cc(-c2ccccc2)cnc1C(=O)N1C[C@@H]2C[C@H]1CN2C(=O)[C@@H](NC(=O)c1cc2ccccc2[nH]1)C(C)(C)C] | N-[(1S)-2,2-dimethyl-1-({(1S,4S)-5-[(3-methyl-5-phenyl-2-pyridinyl)carbonyl]-2,5-diazabicyclo[2.2.1]hept-2-yl}carbonyl)propyl]-1H-indole-2-carboxamide | 550.4 |
| 84 | 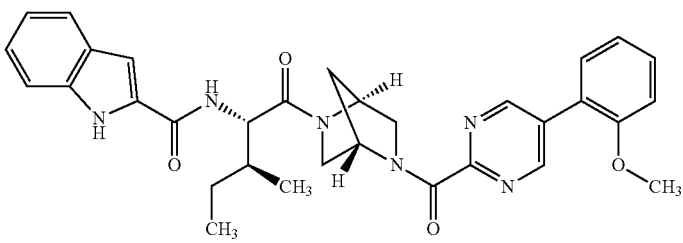 [SMILES: CC[C@H](C)[C@H](NC(=O)c1cc2ccccc2[nH]1)C(=O)N1C[C@@H]2C[C@H]1CN2C(=O)c1ncc(-c2ccccc2OC)cn1] | N-((1S,2S)-2-methyl-1-{[(1S,4S)-5-({5-[2-(methyloxy)phenyl]-2-pyrimidinyl}carbonyl)-2,5-diazabicyclo[2.2.1]hept-2-yl]carbonyl}butyl)-1H-indole-2-carboxamide | 567.2 |

TABLE 5-continued

| Ex # | Structure | Name | LCMS [M + 1]+ |
|---|---|---|---|
| 85 | 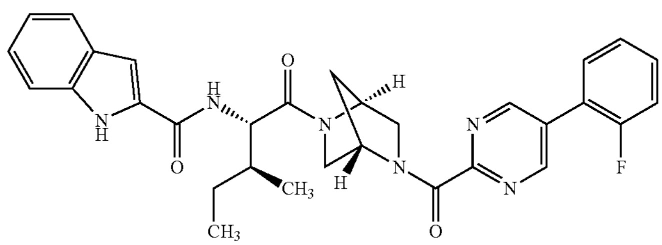 [SMILES: CC[C@H](C)[C@H](NC(=O)c1cc2ccccc2[nH]1)C(=O)N1C[C@@H]2C[C@H]1CN2C(=O)c1ncc(-c2ccccc2F)cn1] | N-{(1S,2S)-1-[((1S,4S)-5-{[5-(2-fluorophenyl)-2-pyrimidinyl]carbonyl}-2,5-diazabicyclo[2.2.1]hept-2-yl)carbonyl]-2-methylbutyl}-1H-indole-2-carboxamide | 555.2 |
| 86 | 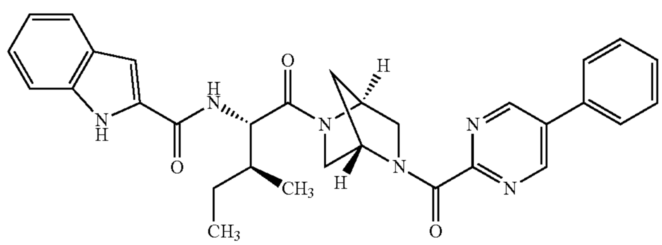 [SMILES: CC[C@H](C)[C@H](NC(=O)c1cc2ccccc2[nH]1)C(=O)N1C[C@@H]2C[C@H]1CN2C(=O)c1ncc(-c2ccccc2)cn1] | N-[(1S,2S)-2-methyl-1-({(1S,4S)-5-[(5-phenyl-2-pyrimidinyl)carbonyl]-2,5-diazabicyclo[2.2.1]hept-2-yl}carbonyl)butyl]-1H-indole-2-carboxamide | 537.3 |
| 87 | 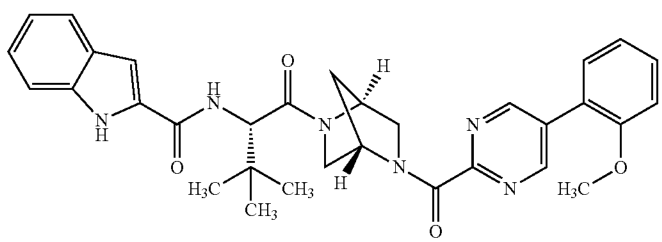 [SMILES: COc1ccccc1-c1cnc(C(=O)N2C[C@@H]3C[C@H]2CN3C(=O)[C@@H](NC(=O)c2cc3ccccc3[nH]2)C(C)(C)C)nc1] | N-((1S)-2,2-dimethyl-1-{[(1S,4S)-5-({5-[2-(methyloxy)phenyl]-2-pyrimidinyl}carbonyl)-2,5-diazabicyclo[2.2.1]hept-2-yl]carbonyl}propyl)-1H-indole-2-carboxamide | 567.3 |
| 88 | 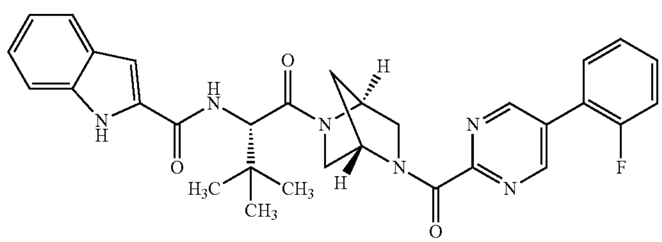 [SMILES: CC(C)(C)[C@H](NC(=O)c1cc2ccccc2[nH]1)C(=O)N1C[C@@H]2C[C@H]1CN2C(=O)c1ncc(-c2ccccc2F)cn1] | N-{(1S)-1-[((1S,4S)-5-{[5-(2-fluorophenyl)-2-pyrimidinyl]carbonyl}-2,5-diazabicyclo[2.2.1]hept-2-yl)carbonyl]-2,2-dimethylpropyl}-1H-indole-2-carboxamide | 555.3 |
| 89 | 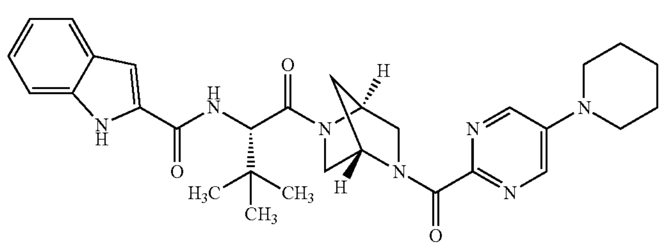 [SMILES: CC(C)(C)[C@H](NC(=O)c1cc2ccccc2[nH]1)C(=O)N1C[C@@H]2C[C@H]1CN2C(=O)c1ncc(N2CCCCC2)cn1] | N-{(1S)-2,2-dimethyl-1-[((1S,4S)-5-{[5-(1-piperidinyl)-2-pyrimidinyl]carbonyl}-2,5-diazabicyclo[2.2.1]hept-2-yl)carbonyl]propyl}-1H-indole-2-carboxamide | 544.3 |
| 90 | 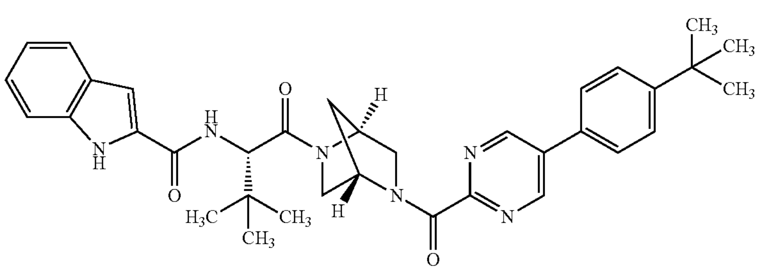 [SMILES: CC(C)(C)c1ccc(-c2cnc(C(=O)N3C[C@@H]4C[C@H]3CN4C(=O)[C@@H](NC(=O)c3cc4ccccc4[nH]3)C(C)(C)C)nc2)cc1] | N-((1S)-1-{[(1S,4S)-5-({5-[4-(1-hydroxy-1-methylethyl)phenyl]-2-pyrimidinyl}carbonyl)-2,5-diazabicyclo[2.2.1]hept-2-yl]carbonyl}-2,2-dimethylpropyl)-1H-indole-2-carboxamide | 594.4 |

TABLE 5-continued

| Ex # | Structure | Name | LCMS [M + 1]+ |
|---|---|---|---|
| 91 | 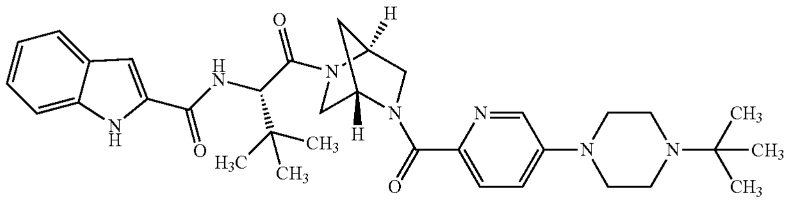 [SMILES: CC(C)(C)[C@H](NC(=O)c1cc2ccccc2[nH]1)C(=O)N1C[C@@H]2C[C@H]1CN2C(=O)c1ccc(N2CCN(C(C)(C)C)CC2)cn1] | N-((1S)-1-{[(1S,4S)-5-({5-[4-(1,1-dimethylethyl)-1-piperazinyl]-2-pyridinyl}carbonyl)-2,5-diazabicyclo[2.2.1]hept-2-yl]carbonyl}-2,2-dimethylpropyl)-1H-indole-2-carboxamide | 600.3 |
| 92 | 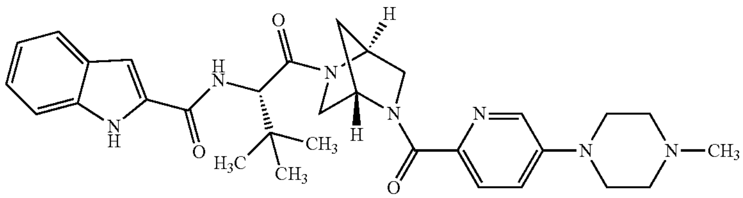 [SMILES: CN1CCN(c2ccc(C(=O)N3C[C@@H]4C[C@H]3CN4C(=O)[C@@H](NC(=O)c3cc4ccccc4[nH]3)C(C)(C)C)nc2)CC1] | N-{(1S)-2,2-dimethyl-1-[((1S,4S)-5-{[5-(4-methyl-1-piperazinyl)-2-pyridinyl]carbonyl}-2,5-diazabicyclo[2.2.1]hept-2-yl)carbonyl]propyl}-1H-indole-2-carboxamide | 558.3 |
| 93 | 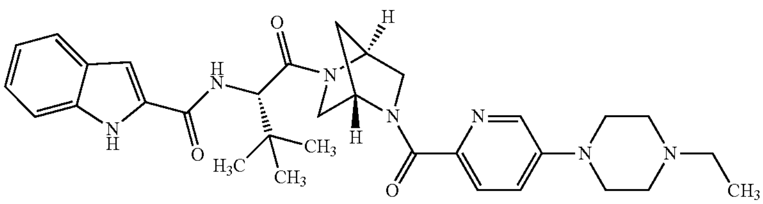 [SMILES: CCN1CCN(c2ccc(C(=O)N3C[C@@H]4C[C@H]3CN4C(=O)[C@@H](NC(=O)c3cc4ccccc4[nH]3)C(C)(C)C)nc2)CC1] | N-{(1S)-1-[((1S,4S)-5-{[5-(4-ethyl-1-piperazinyl)-2-pyridinyl]carbonyl}-2,5-diazabicyclo[2.2.1]hept-2-yl)carbonyl]-2,2-dimethylpropyl}-1H-indole-2-carboxamide | 572.4 |
| 94 | 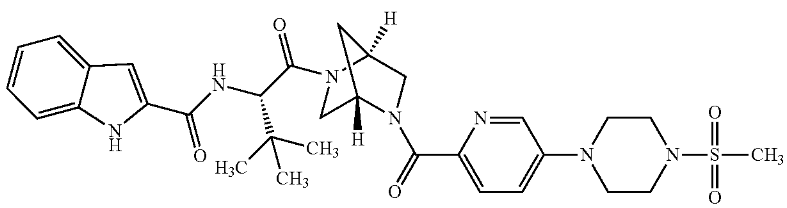 [SMILES: CC(C)(C)[C@H](NC(=O)c1cc2ccccc2[nH]1)C(=O)N1C[C@@H]2C[C@H]1CN2C(=O)c1ccc(N2CCN(S(C)(=O)=O)CC2)cn1] | N-((1S)-2,2-dimethyl-1-{[(1S,4S)-5-({5-[4-(methylsulfonyl)-1-piperazinyl]-2-pyridinyl}carbonyl)-2,5-diazabicyclo[2.2.1]hept-2-yl]carbonyl}propyl)-1H-indole-2-carboxamide | 622.2 |
| 95 | 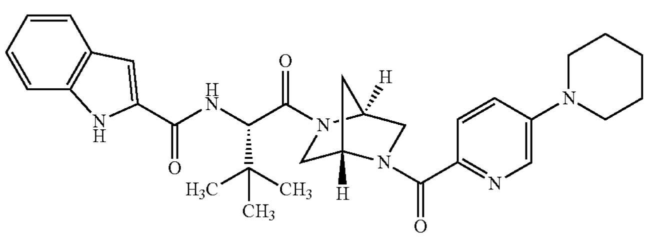 [SMILES: CC(C)(C)[C@H](NC(=O)c1cc2ccccc2[nH]1)C(=O)N1C[C@@H]2C[C@H]1CN2C(=O)c1ccc(N2CCCCC2)cn1] | N-{(1S)-2,2-dimethyl-1-[((1S,4S)-5-{[5-(1-piperidinyl)-2-pyridinyl]carbonyl}-2,5-diazabicyclo[2.2.1]hept-2-yl)carbonyl]propyl}-1H-indole-2-carboxamide | 543.2 |
| 96 | 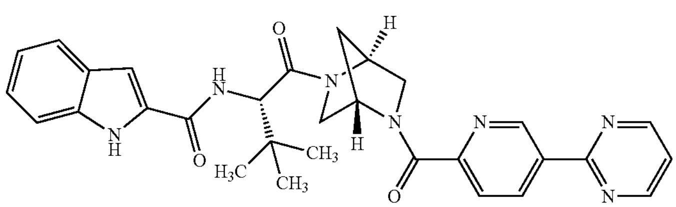 [SMILES: CC(C)(C)[C@H](NC(=O)c1cc2ccccc2[nH]1)C(=O)N1C[C@@H]2C[C@H]1CN2C(=O)c1ccc(-c2ncccn2)cn1] | N-{(1S)-2,2-dimethyl-1-[((1S,4S)-5-{[5-(2-pyrimidinyl)-2-pyridinyl]carbonyl}-2,5-diazabicyclo[2.2.1]hept-2-yl)carbonyl]propyl}-1H-indole-2-carboxamide | 538.3 |
| 97 | 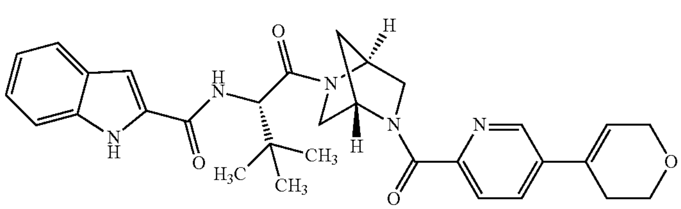 [SMILES: CC(C)(C)[C@H](NC(=O)c1cc2ccccc2[nH]1)C(=O)N1C[C@@H]2C[C@H]1CN2C(=O)c1ccc(C2=CCOCC2)cn1] | N-{(1S)-1-[((1S,4S)-5-{[5-(3,6-dihydro-2H-pyran-4-yl)-2-pyridinyl]carbonyl}-2,5-diazabicyclo[2.2.1]hept-2-yl)carbonyl]-2,2-dimethylpropyl}-1H-indole-2-carboxamide | 542.3 |

TABLE 5-continued

| Ex # | Structure | Name | LCMS [M + 1]+ |
|---|---|---|---|
| 98 | 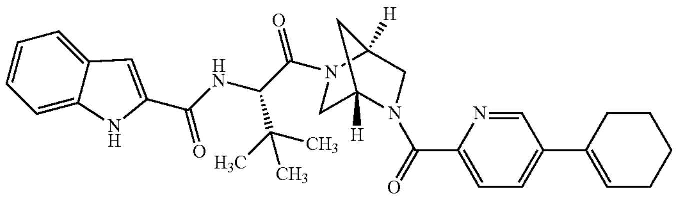 [SMILES: CC(C)(C)[C@H](NC(=O)c1cc2ccccc2[nH]1)C(=O)N1C[C@@H]2C[C@H]1CN2C(=O)c1ccc(C2=CCCCC2)cn1] | N-{(1S)-1-[((1S,4S)-5-{[5-(1-cyclohexen-1-yl)-2-pyridinyl]carbonyl}-2,5-diazabicyclo[2.2.1]hept-2-yl)carbonyl]-2,2-dimethylpropyl}-1H-indole-2-carboxamide | 540.3 |
| 99 | 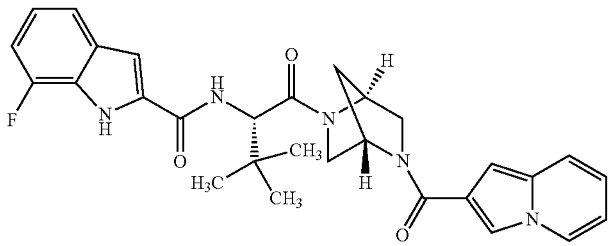 [SMILES: CC(C)(C)[C@H](NC(=O)c1cc2cccc(F)c2[nH]1)C(=O)N1C[C@@H]2C[C@H]1CN2C(=O)c1cc2ccccn2c1] | 7-fluoro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide | 516.2 |
| 100 | 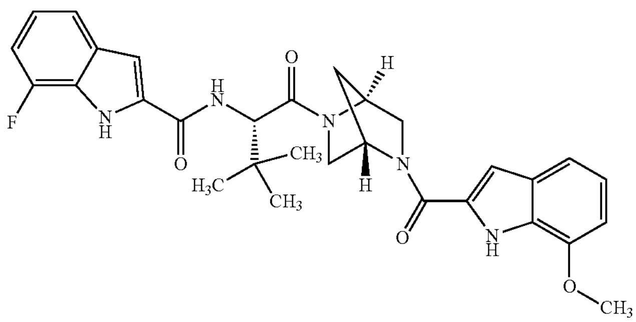 [SMILES: COc1cccc2cc(C(=O)N3C[C@@H]4C[C@H]3CN4C(=O)[C@@H](NC(=O)c3cc4cccc(F)c4[nH]3)C(C)(C)C)[nH]c12] | N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-7-fluoro-1H-indole-2-carboxamide | 546.3 |
| 101 | 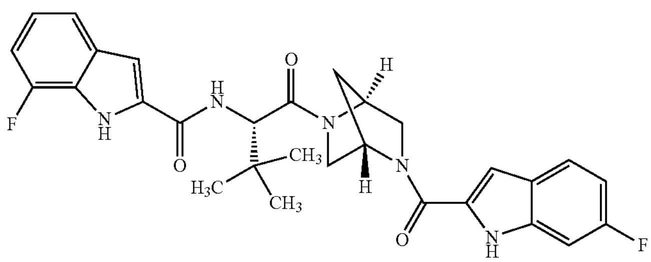 [SMILES: CC(C)(C)[C@H](NC(=O)c1cc2cccc(F)c2[nH]1)C(=O)N1C[C@@H]2C[C@H]1CN2C(=O)c1cc2ccc(F)cc2[nH]1] | 7-fluoro-N-[(1S)-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide | 534.2 |
| 102 | 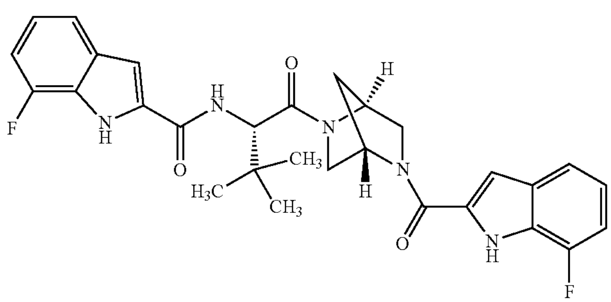 [SMILES: CC(C)(C)[C@H](NC(=O)c1cc2cccc(F)c2[nH]1)C(=O)N1C[C@@H]2C[C@H]1CN2C(=O)c1cc2cccc(F)c2[nH]1] | 7-fluoro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide | 534.2 |
| 103 | 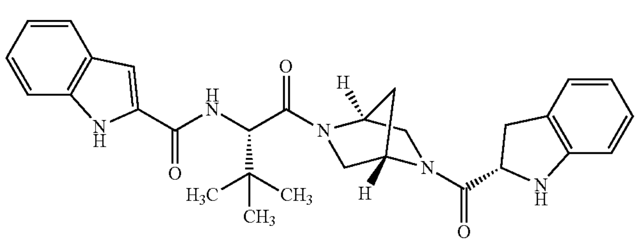 [SMILES: CC(C)(C)[C@H](NC(=O)c1cc2ccccc2[nH]1)C(=O)N1C[C@@H]2C[C@H]1CN2C(=O)[C@@H]1Cc2ccccc2N1] | N-[(1S)-1-({(1S,4S)-5-[(2S)-2,3-dihydro-1H-indol-2-ylcarbonyl]-2,5-diazabicyclo[2.2.1]hept-2-yl}carbonyl)-2,2-dimethylpropyl]-1H-indole-2-carboxamide | 500.2 |

TABLE 5-continued

| Ex # | Structure | Name | LCMS [M + 1]+ |
|---|---|---|---|
| 104 | 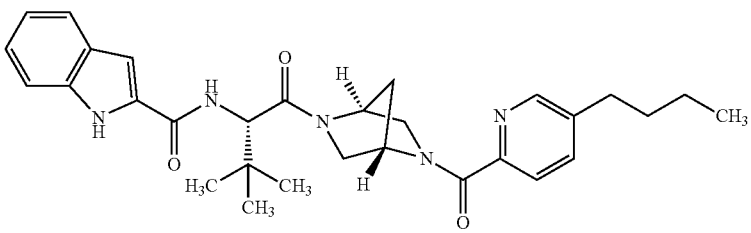 [SMILES: CCCCc1ccc(C(=O)N2C[C@@H]3C[C@H]2CN3C(=O)[C@@H](NC(=O)c2cc3ccccc3[nH]2)C(C)(C)C)nc1] | N-[(1S)-1-({(1S,4S)-5-[(5-butyl-2-pyridinyl)carbonyl]-2,5-diazabicyclo[2.2.1]hept-2-yl}carbonyl)-2,2-dimethylpropyl]-1H-indole-2-carboxamide | 516.2 |
| 105 | 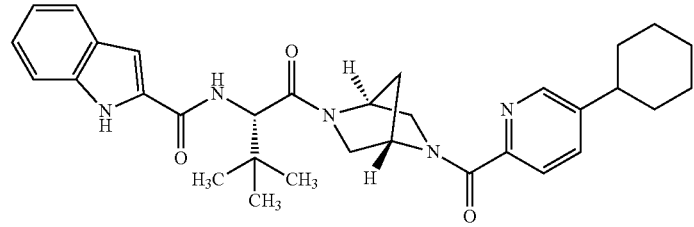 [SMILES: CC(C)(C)[C@H](NC(=O)c1cc2ccccc2[nH]1)C(=O)N1C[C@@H]2C[C@H]1CN2C(=O)c1ccc(C2CCCCC2)cn1] | N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide | 542.2 |
| 106 | 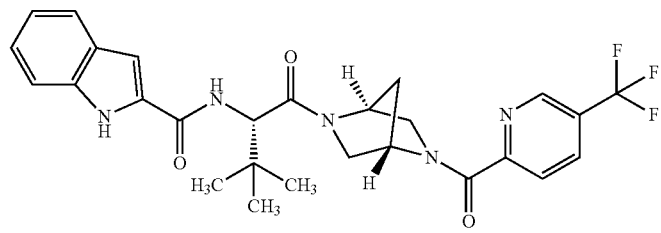 [SMILES: CC(C)(C)[C@H](NC(=O)c1cc2ccccc2[nH]1)C(=O)N1C[C@@H]2C[C@H]1CN2C(=O)c1ccc(C(F)(F)F)cn1] | N-{(1S)-2,2-dimethyl-1-[((1S,4S)-5-{[5-(trifluoromethyl)-2-pyridinyl]carbonyl}-2,5-diazabicyclo[2.2.1]hept-2-yl)carbonyl]propyl}-1H-indole-2-carboxamide] | 528.2 |
| 107 | 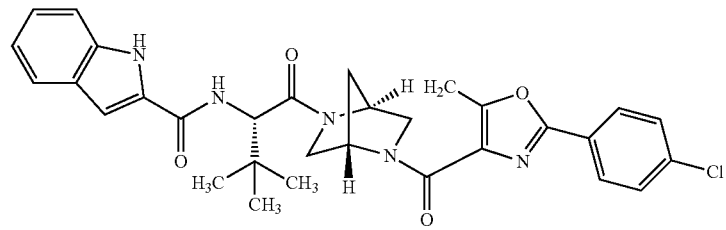 [SMILES: Cc1oc(-c2ccc(Cl)cc2)nc1C(=O)N1C[C@@H]2C[C@H]1CN2C(=O)[C@@H](NC(=O)c1cc2ccccc2[nH]1)C(C)(C)C] | N-{(1S)-1-[((1S,4S)-5-{[2-(4-chlorophenyl)-5-methyl-1,3-oxazol-4-yl]carbonyl}-2,5-diazabicyclo[2.2.1]hept-2-yl)carbonyl]-2,2-dimethylpropyl}-1H-indole-2-carboxamide | 574.2 |
| 108 | 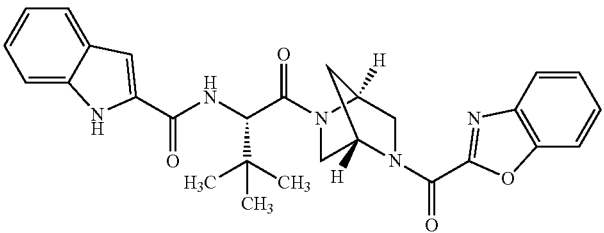 [SMILES: CC(C)(C)[C@H](NC(=O)c1cc2ccccc2[nH]1)C(=O)N1C[C@@H]2C[C@H]1CN2C(=O)c1nc2ccccc2o1] | N-((1S)-1-{[(1S,4S)-5-(1,3-benzoxazol-2-ylcarbonyl)-2,5-diazabicyclo[2.2.1]hept-2-yl]carbonyl}-2,2-dimethylpropyl)-1H-indole-2-carboxamide | 500.2 |
| 109 | 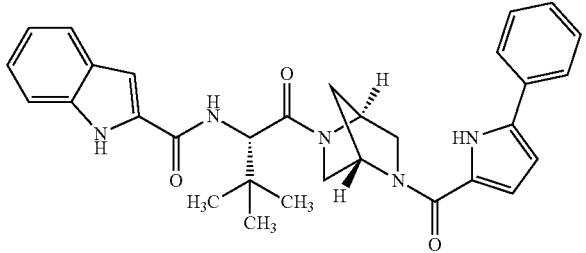 [SMILES: CC(C)(C)[C@H](NC(=O)c1cc2ccccc2[nH]1)C(=O)N1C[C@@H]2C[C@H]1CN2C(=O)c1ccc(-c2ccccc2)[nH]1] | N-[(1S)-2,2-dimethyl-1-({(1S,4S)-5-[(5-phenyl-1H-pyrrol-2-yl)carbonyl]-2,5-diazabicyclo[2.2.1]hept-2-yl}carbonyl)propyl]-1H-indole-2-carboxamide | 524.3 |

TABLE 5-continued

| Ex # | Structure | Name | LCMS [M + 1]+ |
|---|---|---|---|
| 110 | 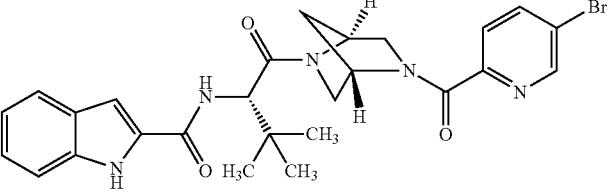 | N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide | 540.2 |
| 111 | 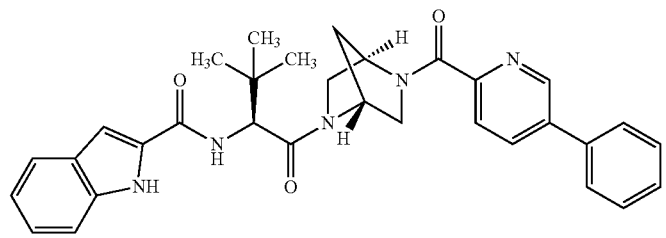 [SMILES: CC(C)(C)[C@H](NC(=O)c1cc2ccccc2[nH]1)C(=O)N1C[C@H]2C[C@@H]1CN2C(=O)c1ccc(-c2ccccc2)cn1] | N-[(1S)-2,2-dimethyl-1-({(1R,4R)-5-[(5-phenyl-2-pyridinyl)carbonyl]-2,5-diazabicyclo[2.2.1]hept-2-yl}carbonyl)propyl]-1H-indole-2-carboxamide | 536.3 |
| 112 | 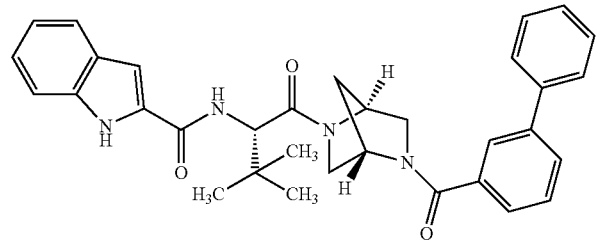 [SMILES: CC(C)(C)[C@H](NC(=O)c1cc2ccccc2[nH]1)C(=O)N1C[C@@H]2C[C@H]1CN2C(=O)c1cccc(-c2ccccc2)c1] | N-((1S)-1-{[(1S,4S)-5-(3-biphenylylcarbonyl)-2,5-diazabicyclo[2.2.1]hept-2-yl]carbonyl}-2,2-dimethylpropyl)-1H-indole-2-carboxamide | 535.4 |
| 113 | 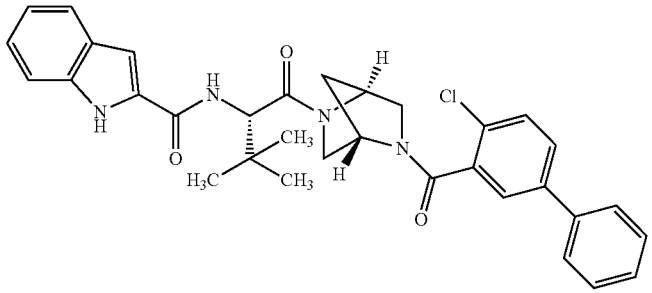 [SMILES: CC(C)(C)[C@H](NC(=O)c1cc2ccccc2[nH]1)C(=O)N1C[C@@H]2C[C@H]1CN2C(=O)c1cc(-c2ccccc2)ccc1Cl] | N-[(1S)-1-({(1S,4S)-5-[(4-chloro-3-biphenylyl)carbonyl]-2,5-diazabicyclo[2.2.1]hept-2-yl}carbonyl)-2,2-dimethylpropyl]-1H-indole-2-carboxamide | 569.3 |
| 114 | 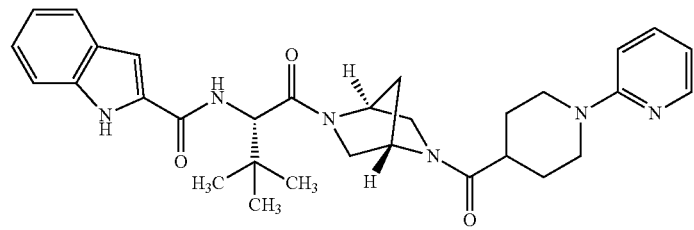 [SMILES: CC(C)(C)[C@H](NC(=O)c1cc2ccccc2[nH]1)C(=O)N1C[C@@H]2C[C@H]1CN2C(=O)C1CCN(c2ccccn2)CC1] | N-{(1S)-2,2-dimethyl-1-[((1S,4S)-5-{[1-(2-pyridinyl)-4-piperidinyl]carbonyl}-2,5-diazabicyclo[2.2.1]hept-2-yl)carbonyl]propyl}-1H-indole-2-carboxamide | 543.3 |
| 115 | 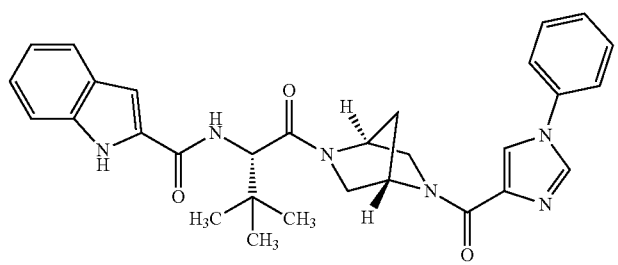 [SMILES: CC(C)(C)[C@H](NC(=O)c1cc2ccccc2[nH]1)C(=O)N1C[C@@H]2C[C@H]1CN2C(=O)c1cn(-c2ccccc2)cn1] | N-[(1S)-2,2-dimethyl-1-({(1S,4S)-5-[(1-phenyl-1H-imidazol-4-yl)carbonyl]-2,5-diazabicyclo[2.2.1]hept-2-yl}carbonyl)propyl]-1H-indole-2-carboxamide | 525.2 |

TABLE 5-continued

| Ex # | Structure | Name | LCMS [M + 1]+ |
|---|---|---|---|
| 116 | 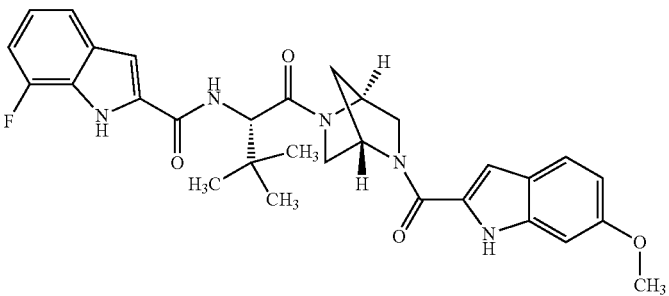 [SMILES: COc1ccc2cc(C(=O)N3C[C@@H]4C[C@H]3CN4C(=O)[C@@H](NC(=O)c3cc4cccc(F)c4[nH]3)C(C)(C)C)[nH]c2c1] | N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-7-fluoro-1H-indole-2-carboxamide | 546.2 |
| 117 | 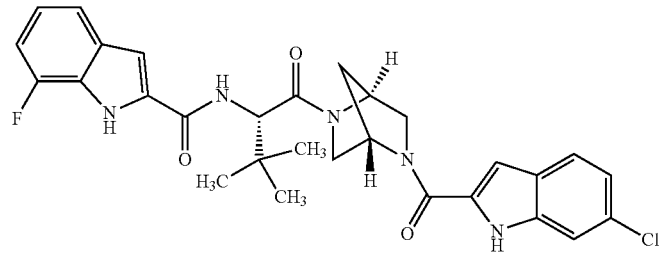 [SMILES: CC(C)(C)[C@H](NC(=O)c1cc2cccc(F)c2[nH]1)C(=O)N1C[C@@H]2C[C@H]1CN2C(=O)c1cc2ccc(Cl)cc2[nH]1] | N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-7-fluoro-1H-indole-2-carboxamide | 550.2 |
| 118 | 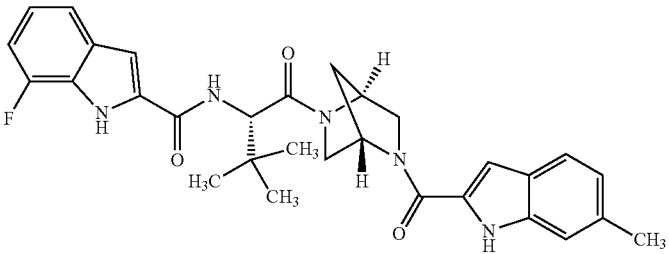 [SMILES: Cc1ccc2cc(C(=O)N3C[C@@H]4C[C@H]3CN4C(=O)[C@@H](NC(=O)c3cc4cccc(F)c4[nH]3)C(C)(C)C)[nH]c2c1] | N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-7-fluoro-1H-indole-2-carboxamide | 530.3 |
| 119 | 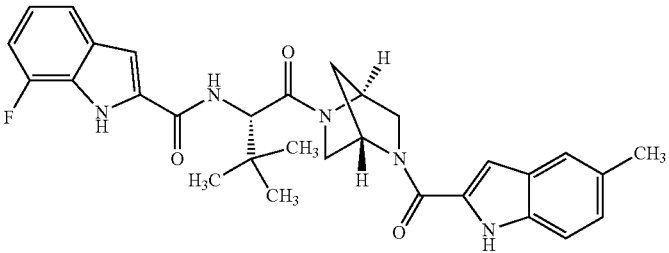 [SMILES: Cc1ccc2[nH]c(C(=O)N3C[C@@H]4C[C@H]3CN4C(=O)[C@@H](NC(=O)c3cc4cccc(F)c4[nH]3)C(C)(C)C)cc2c1] | N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-7-fluoro-1H-indole-2-carboxamide | 530.1 |
| 120 | 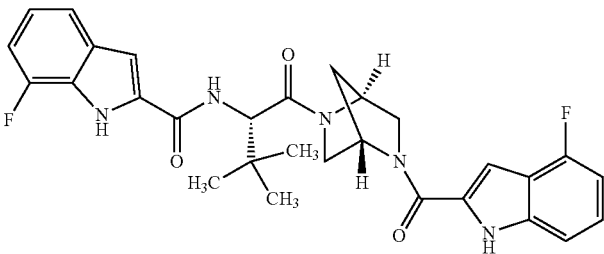 [SMILES: CC(C)(C)[C@H](NC(=O)c1cc2cccc(F)c2[nH]1)C(=O)N1C[C@@H]2C[C@H]1CN2C(=O)c1cc2c(F)cccc2[nH]1] | 7-fluoro-N-[(1S)-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide | 534.2 |
| 121 | 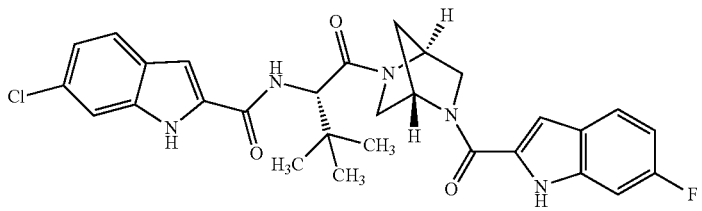 [SMILES: CC(C)(C)[C@H](NC(=O)c1cc2ccc(Cl)cc2[nH]1)C(=O)N1C[C@@H]2C[C@H]1CN2C(=O)c1cc2ccc(F)cc2[nH]1] | 6-chloro-N-[(1S)-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide | 550.2 |

TABLE 5-continued

| Ex # | Structure | Name | LCMS [M + 1]+ |
|---|---|---|---|
| 122 | 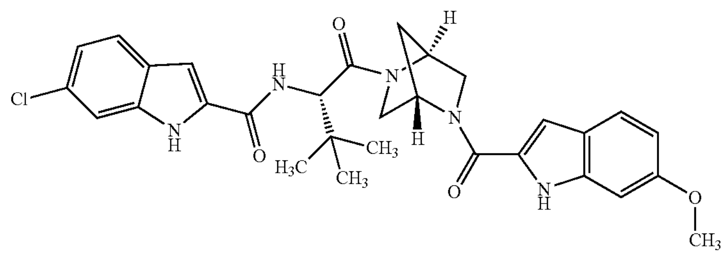 [SMILES: COc1ccc2cc(C(=O)N3C[C@@H]4C[C@H]3CN4C(=O)[C@@H](NC(=O)c3cc4ccc(Cl)cc4[nH]3)C(C)(C)C)[nH]c2c1] | 6-chloro-N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide | 562.3 |
| 123 | 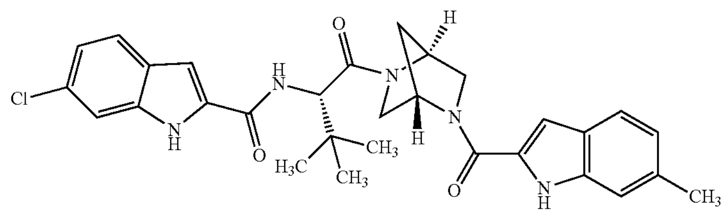 [SMILES: Cc1ccc2cc(C(=O)N3C[C@@H]4C[C@H]3CN4C(=O)[C@@H](NC(=O)c3cc4ccc(Cl)cc4[nH]3)C(C)(C)C)[nH]c2c1] | 6-chloro-N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide | 546.3 |
| 124 | 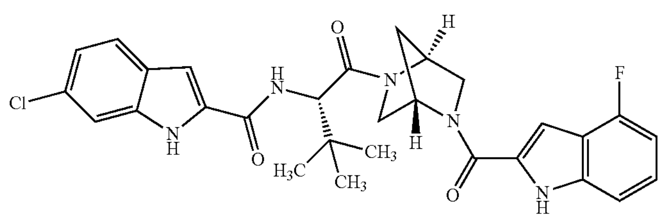 [SMILES: CC(C)(C)[C@H](NC(=O)c1cc2ccc(Cl)cc2[nH]1)C(=O)N1C[C@@H]2C[C@H]1CN2C(=O)c1cc2c(F)cccc2[nH]1] | 6-chloro-N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide | 550.3 |
| 125 | 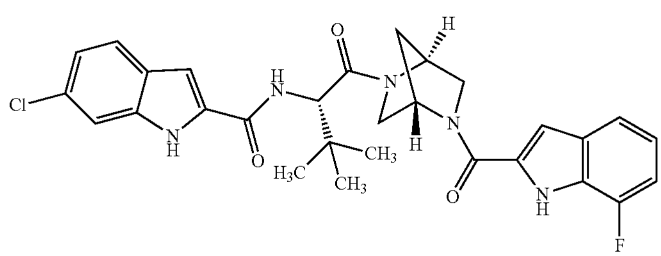 [SMILES: CC(C)(C)[C@H](NC(=O)c1cc2ccc(Cl)cc2[nH]1)C(=O)N1C[C@@H]2C[C@H]1CN2C(=O)c1cc2cccc(F)c2[nH]1] | 6-chloro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide | 550.2 |
| 126 | 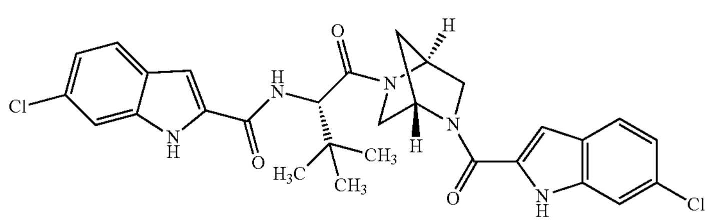 [SMILES: CC(C)(C)[C@H](NC(=O)c1cc2ccc(Cl)cc2[nH]1)C(=O)N1C[C@@H]2C[C@H]1CN2C(=O)c1cc2ccc(Cl)cc2[nH]1] | 6-chloro-N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide | 174: (M − 392 |
| 127 | 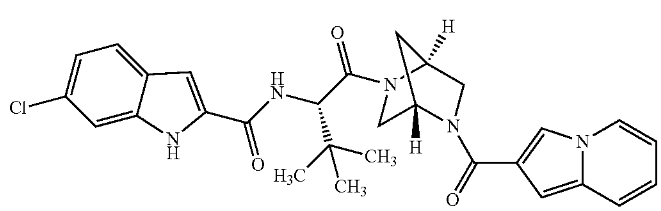 [SMILES: CC(C)(C)[C@H](NC(=O)c1cc2ccc(Cl)cc2[nH]1)C(=O)N1C[C@@H]2C[C@H]1CN2C(=O)c1cc2ccccn2c1] | 6-chloro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide | 532.3 |

TABLE 5-continued

| Ex # | Structure | Name | LCMS [M + 1]+ |
|---|---|---|---|
| 128 | 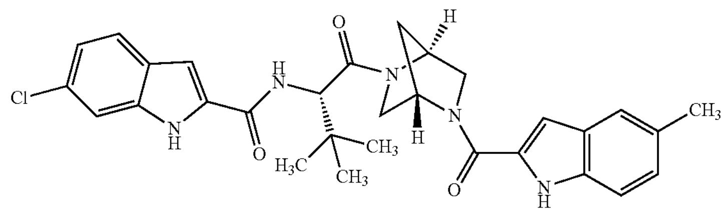 [SMILES: Cc1ccc2[nH]c(C(=O)N3C[C@@H]4C[C@H]3CN4C(=O)[C@@H](NC(=O)c3cc4ccc(Cl)cc4[nH]3)C(C)(C)C)cc2c1] | 6-chloro-N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide | 546.2 |
| 129 | 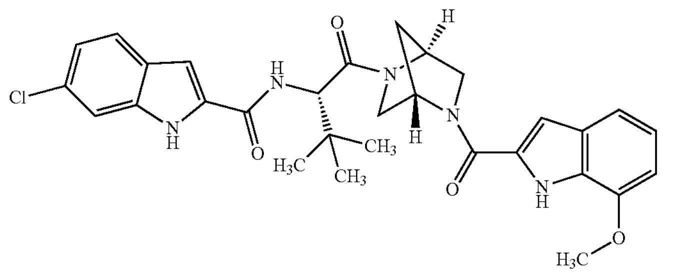 [SMILES: COc1cccc2cc(C(=O)N3C[C@@H]4C[C@H]3CN4C(=O)[C@@H](NC(=O)c3cc4ccc(Cl)cc4[nH]3)C(C)(C)C)[nH]c12] | 6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide | 562.3 |
| 130 | 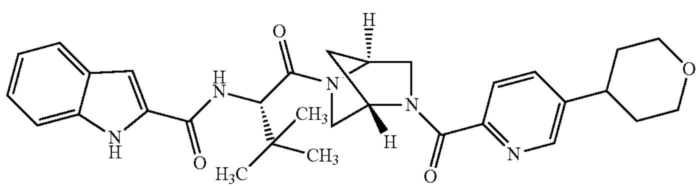 [SMILES: CC(C)(C)[C@H](NC(=O)c1cc2ccccc2[nH]1)C(=O)N1C[C@@H]2C[C@H]1CN2C(=O)c1ccc(C2CCOCC2)cn1] | 6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide | 544.4 |

Example 131

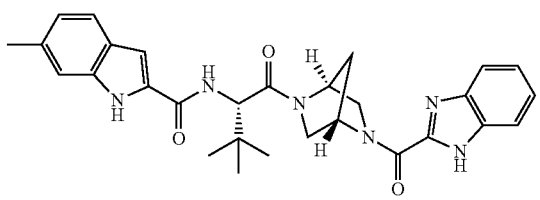 [SMILES: Cc1ccc2cc(C(=O)N[C@H](C(=O)N3C[C@@H]4C[C@H]3CN4C(=O)c3nc4ccccc4[nH]3)C(C)(C)C)[nH]c2c1]

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-methyl-1H-indole-2-carboxamide

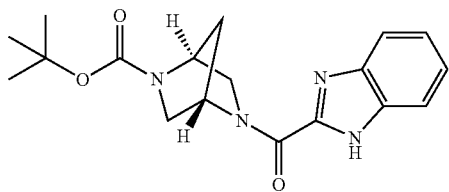 [SMILES: CC(C)(C)OC(=O)N1C[C@@H]2C[C@H]1CN2C(=O)c1nc2ccccc2[nH]1]

1,1-Dimethylethyl (1S,4S)-5-(1H-benzimidazol-2-ylcarbonyl)-2,5-diazabicyclo[2.2.1]heptane-2-carboxylate A mixture of 1,1-dimethylethyl (1S,4S)-2,5-diazabicyclo[2.2.1]heptane-2-carboxylate (18.3 g, 92.5 mmol), 1H-benzimidazole-2-carboxylic acid, (15.0 g, 92.5 mmol), EDC (21.3 g, 111 mmol), HOBt (2.5 g, 18.5 mmol), NMM (28 g, 277.5 mmol) in CH$_2$Cl$_2$ (250 mL) was stirred at room temperature for 18 h. The reaction was diluted with water and CH$_2$Cl$_2$ then washed with sat. NaHCO$_3$ (200 mL) and brine (200 mL). The solution was dried over anhydrous Na$_2$SO$_4$ and concentrated to give a crude product which was purified by column chromatography on silica gel (petroleum ether/ethyl acetate: 2/1) to give the title compound (20 g) as a white solid. LCMS (m/z): 343.2 (M+H).

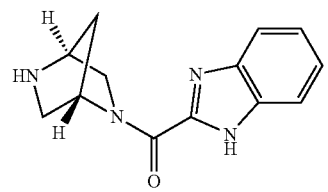 [SMILES: O=C(c1nc2ccccc2[nH]1)N1C[C@@H]2C[C@H]1CN2]

2-[(1S,4S)-2,5-diazabicyclo[2.2.1]hept-2-ylcarbonyl]-1H-benzimidazole

A solution of 1,1-Dimethylethyl (1S,4S)-5-(1H-benzimidazol-2-ylcarbonyl)-2,5-diazabicyclo[2.2.1]heptane-2-carboxylate (20 g, 58.5 mmol) in 200 ml TFA/DCM (20%) was stirred at room temperature for 1 h. The reaction mixture was basified by addition of sat. aqueous Na$_2$CO$_3$ and then extracted with DCM (4×200 mL). The DCM solution was dried over anhydrous Na$_2$SO$_4$ and concentrated to give the title compound (6.5 g) as a pale yellow solid. LCMS (m/z): 243.1 (M+H).

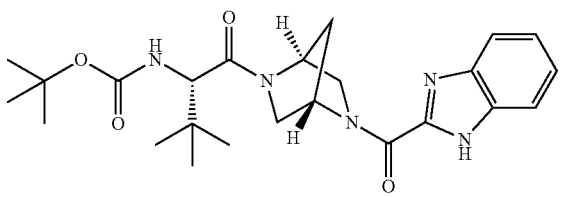 [SMILES: CC(C)(C)OC(=O)N[C@H](C(=O)N1C[C@@H]2C[C@H]1CN2C(=O)c1nc2ccccc2[nH]1)C(C)(C)C]

1,1-Dimethylethyl ((1S)-1-{[(1S,4S)-5-(1H-benzimidazol-2-ylcarbonyl)-2,5-diazabicyclo[2.2.1]hept-2-yl]carbonyl}-2,2-dimethylpropyl)carbamate A solution of N-{[(1,1-dimethylethyl)oxy]carbonyl}-3-methyl-L-valine (3 g, 13 mmol) (2-[(1S,4S)-2,5-diazabicyclo[2.2.1]hept-2-ylcarbonyl]-1H-benzimidazole (3 g, 12.4 mmol), EDC (2.8 g, 14.8 mmol), HOBt (334 mg, 2.5 mmol), NMM (3.7 g, 37.1 mmol) in $CH_2Cl_2$ (50 mL) was stirred at room temperature for 18 h. The reaction was diluted with water and $CH_2Cl_2$ then washed with sat. $NaHCO_3$ (50 mL) and brine (50 mL). The solution was dried over anhydrous $Na_2SO_4$ and concentrated to give the title compound (5.6 g) as a pale yellow solid. LCMS (m/z): 456.3 (M+H).

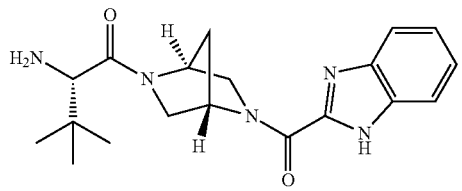 [SMILES: CC(C)(C)[C@H](N)C(=O)N1C[C@@H]2C[C@H]1CN2C(=O)c1nc2ccccc2[nH]1]

(2S)-1-[(1S,4S)-5-(1H-benzimidazol-2-ylcarbonyl)-2,5-diazabicyclo[2.2.1]hept-2-yl]-3,3-dimethyl-1-oxo-2-butanamine A solution of 1,1-Dimethylethyl ((1S)-1-{[(1S,4S)-5-(1H-benzimidazol-2-ylcarbonyl)-2,5-diazabicyclo[2.2.1]hept-2-yl]carbonyl}-2,2-dimethylpropyl)carbamate (5.8 g, 12.7 mmol) in 60 ml TFA/DCM (20%) was stirred at room temperature for 1 h. The reaction mixture was basified by addition of sat. aqueous $Na_2CO_3$ and then extracted with DCM (3×50 mL). The DCM solution was dried over anhydrous $Na_2SO_4$ and concentrated to give the title compound (3.6 g) as a pale yellow solid. LCMS (m/z): 356.2 (M+H).

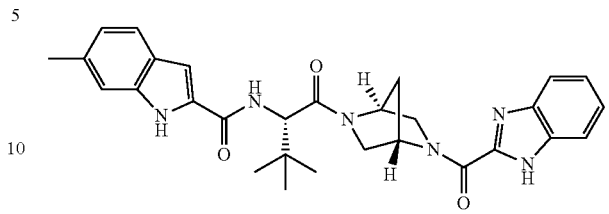

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-methyl-1H-indole-2-carboxamide A solution of (2S)-1-[(1S,4S)-5-(1H-benzimidazol-2-ylcarbonyl)-2,5-diazabicyclo[2.2.1]hept-2-yl]-3,3-dimethyl-1-oxo-2-butanamine (120 mg, 0.34 mmol), 6-methyl-1H-indole-2-carboxylic acid (60 mg, 0.34 mmol), EDC (78 mg, 0.41 mmol), HOBt (9 mg, 0.068 mmol), NMM (103 mg, 1.02 mmol) in $CH_2Cl_2$ (2 mL) was stirred at room temperature for 18 h. The reaction was diluted with water and $CH_2Cl_2$ then washed with sat. $NaHCO_3$ (20 mL) and brine (20 mL). The solution was dried over anhydrous $Na_2SO_4$ and concentrated to give the crude product, which was purified by reverse phase HPLC: 50-80% ACN/Water (0.1% TFA). Concentration of the fractions containing product afforded the title compound (105 mg) as a white solid. LCMS (m/z): 513.1 (M+H). 1H NMR (400 MHz, $CDCl_3$) δ ppm: 0.90-1.10 (m, 9H), 1.75-2.20 (m, 2H), 2.30-2.40 (m, 3H), 3.45-3.95 (m, 3H), 4.00-5.25 m, 4H), 6.20-6.75 (m, 1H), 6.80-7.70 (m, 9H), 9.30-9.70 (m, 1H)

Examples 132-177

The compounds in Table 6 were prepared by a method similar to the one described for the preparation of N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-methyl-1H-indole-2-carboxamide (Example 131). As is appreciated by those skilled in the art, these analogous examples may involve variations in general reaction conditions.

TABLE 6

| Ex # | Structure | Name | LCMS [M + 1]+ |
|---|---|---|---|
| 132 | 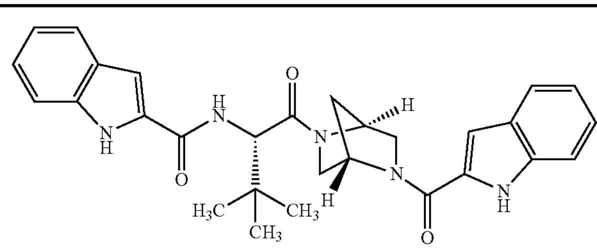 | N-((1R)-1-{[(1S,4R)-5-(1H-indol-2-ylcarbonyl)-2,5-diazabicyclo[2.2.1]hept-2-yl]carbonyl}-2,2-dimethylpropyl)-1H-indole-2-carboxamide | 498.3 |

TABLE 6-continued

| Ex # | Structure | Name | LCMS [M + 1]+ |
|---|---|---|---|
| 133 | 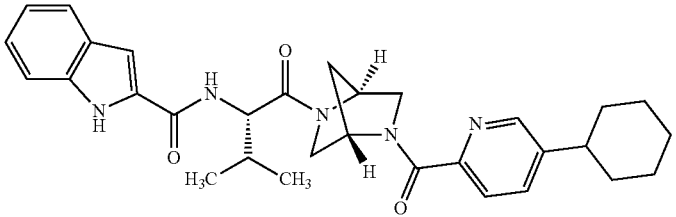 [SMILES: CC(C)[C@H](NC(=O)c1cc2ccccc2[nH]1)C(=O)N1C[C@@H]2C[C@H]1CN2C(=O)c1ccc(C2CCCCC2)cn1] | N-[(1S)-1-({(1S,4S)-5-[(5-cyclohexyl-2-pyridinyl)carbonyl]-2,5-diazabicyclo[2.2.1]hept-2-yl}carbonyl)-2-methylpropyl]-1H-indole-2-carboxamide | 528.4 |
| 134 | 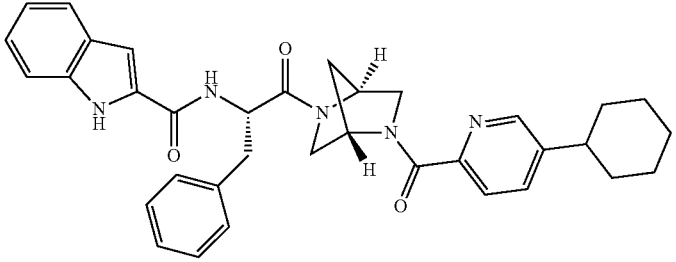 [SMILES: O=C(N[C@@H](Cc1ccccc1)C(=O)N1C[C@@H]2C[C@H]1CN2C(=O)c1ccc(C2CCCCC2)cn1)c1cc2ccccc2[nH]1] | N-[(1S)-2-{(1S,4S)-5-[(5-cyclohexyl-2-pyridinyl)carbonyl]-2,5-diazabicyclo[2.2.1]hept-2-yl}-2-oxo-1-(phenylmethyl)ethyl]-1H-indole-2-carboxamide | 576.3 |
| 135 | 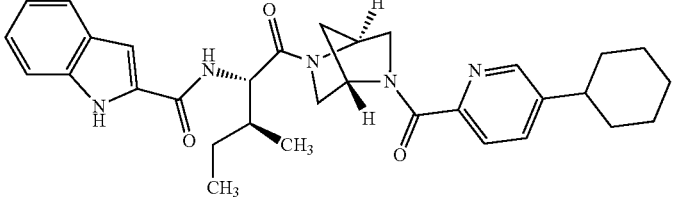 | N-[(1S,2S)-1-({(1S,4S)-5-[(5-cyclohexyl-2-pyridinyl)carbonyl]-2,5-diazabicyclo[2.2.1]hept-2-yl}carbonyl)-2-methylbutyl]-1H-indole-2-carboxamide | 542.3 |
| 136 | 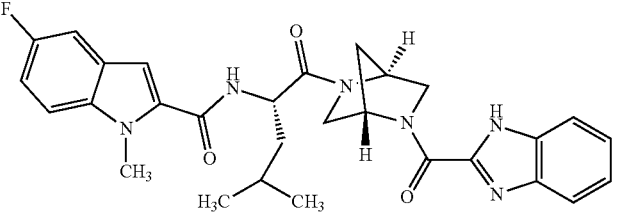 [SMILES: CC(C)C[C@H](NC(=O)c1cc2cc(F)ccc2n1C)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1-methyl-1H-indole-2-carboxamide | 531.3 |
| 137 | 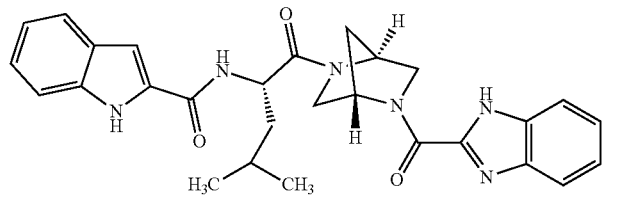 [SMILES: CC(C)C[C@H](NC(=O)c1cc2ccccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-1H-indole-2-carboxamide | 499.2 |
| 138 | 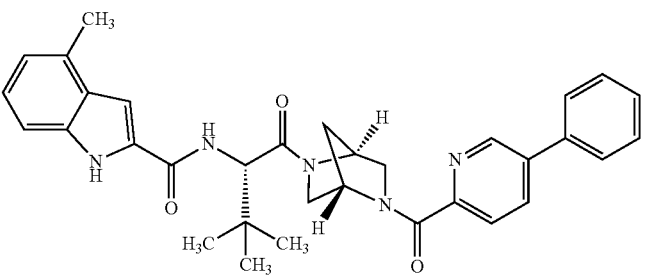 [SMILES: Cc1cccc2[nH]c(C(=O)N[C@H](C(=O)N3C[C@@H]4C[C@H]3CN4C(=O)c3ccc(-c4ccccc4)cn3)C(C)(C)C)cc12] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-methyl-1H-indole-2-carboxamide} | 550.3 |

TABLE 6-continued

| Ex # | Structure | Name | LCMS [M + 1]+ |
|---|---|---|---|
| 139 | 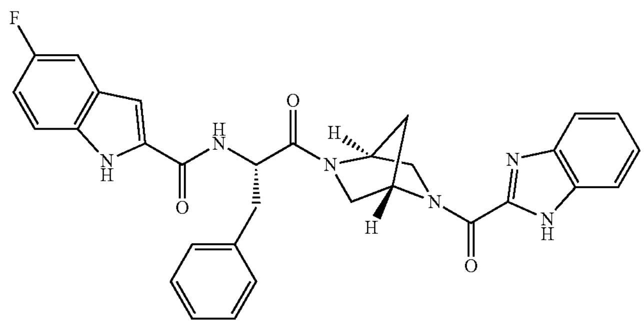 [SMILES: O=C(N[C@@H](Cc1ccccc1)C(=O)N1C[C@@H]2C[C@H]1CN2C(=O)c1nc2ccccc2[nH]1)c1cc2cc(F)ccc2[nH]1] | N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-5-fluoro-1H-indole-2-carboxamide | 551.3 |
| 140 | 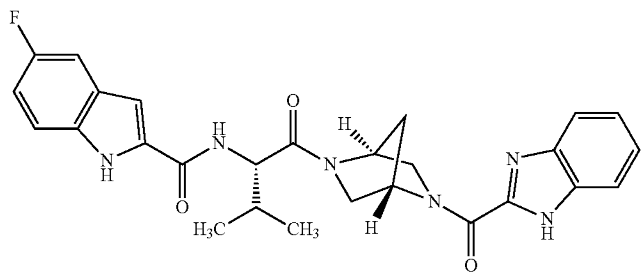 [SMILES: CC(C)[C@H](NC(=O)c1cc2cc(F)ccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2-methylpropyl)-5-fluoro-1H-indole-2-carboxamide | 503.3 |
| 141 | 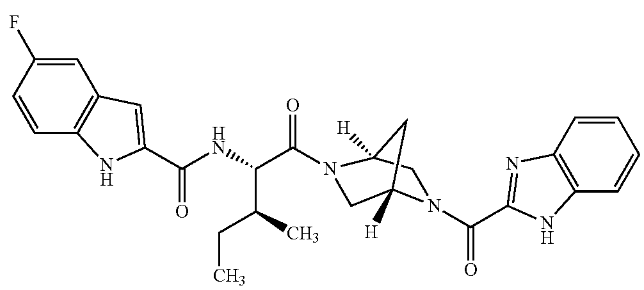 [SMILES: CC[C@H](C)[C@H](NC(=O)c1cc2cc(F)ccc2[nH]1)C(=O)N1C[C@@H]2C[C@H]1CN2C(=O)c1nc2ccccc2[nH]1] | N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-5-fluoro-1H-indole-2-carboxamide | 517.3 |
| 142 | 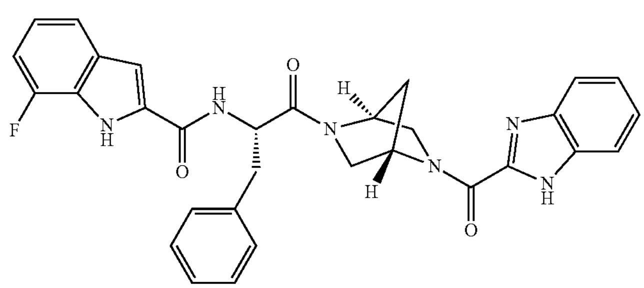 [SMILES: O=C(N[C@@H](Cc1ccccc1)C(=O)N1C[C@@H]2C[C@H]1CN2C(=O)c1nc2ccccc2[nH]1)c1cc2cccc(F)c2[nH]1] | N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-7-fluoro-1H-indole-2-carboxamide | 551.1 |
| 143 | 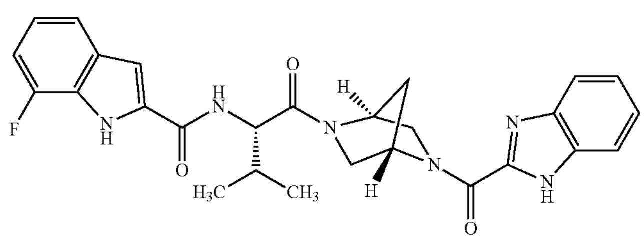 [SMILES: CC(C)[C@H](NC(=O)c1cc2cccc(F)c2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2-methylpropyl)-7-fluoro-1H-indole-2-carboxamide | 503.3 |

TABLE 6-continued

| Ex # | Structure | Name | LCMS [M + 1]+ |
|---|---|---|---|
| 144 | 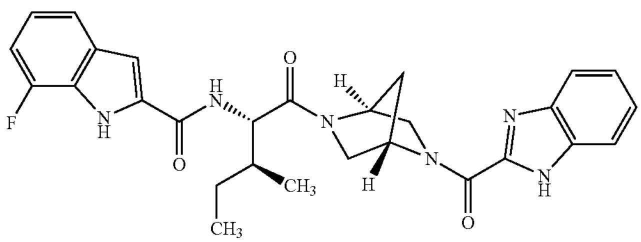 [SMILES: CC[C@H](C)[C@H](NC(=O)c1cc2cccc(F)c2[nH]1)C(=O)N1C[C@@H]2C[C@H]1CN2C(=O)c1nc2ccccc2[nH]1] | N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-7-fluoro-1H-indole-2-carboxamide | 517.3 |
| 145 | 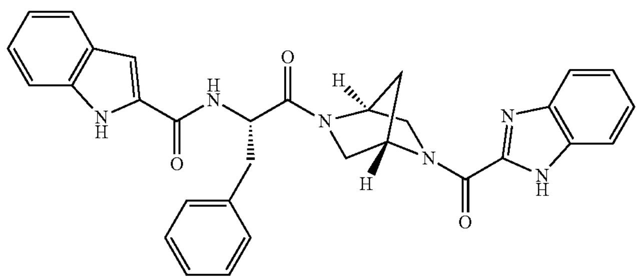 [SMILES: O=C(N[C@@H](Cc1ccccc1)C(=O)N1C[C@@H]2C[C@H]1CN2C(=O)c1nc2ccccc2[nH]1)c1cc2ccccc2[nH]1] | N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-1H-indole-2-carboxamide | 533.2 |
| 146 | 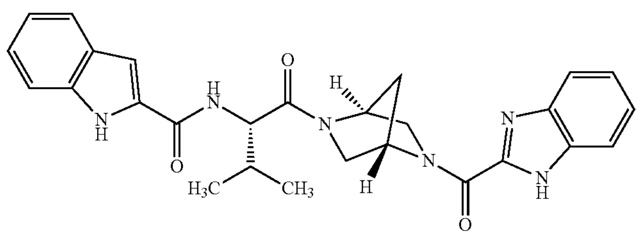 [SMILES: CC(C)[C@H](NC(=O)c1cc2ccccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2-methylpropyl)-1H-indole-2-carboxamide | 485.2 |
| 147 | 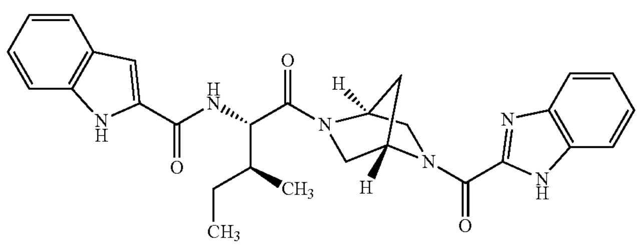 [SMILES: CC[C@H](C)[C@H](NC(=O)c1cc2ccccc2[nH]1)C(=O)N1C[C@@H]2C[C@H]1CN2C(=O)c1nc2ccccc2[nH]1] | N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-1H-indole-2-carboxamide | 499.3 |
| 148 | 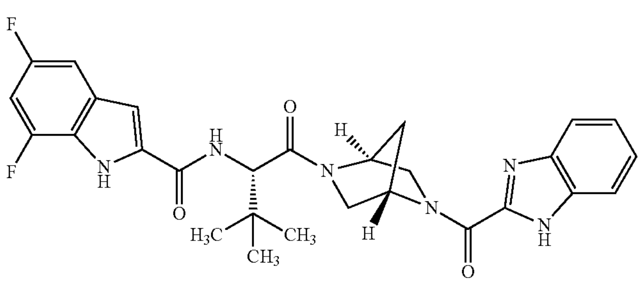 [SMILES: CC(C)(C)[C@H](NC(=O)c1cc2cc(F)cc(F)c2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,7-difluoro-1H-indole-2-carboxamide | 535.1 |
| 149 | 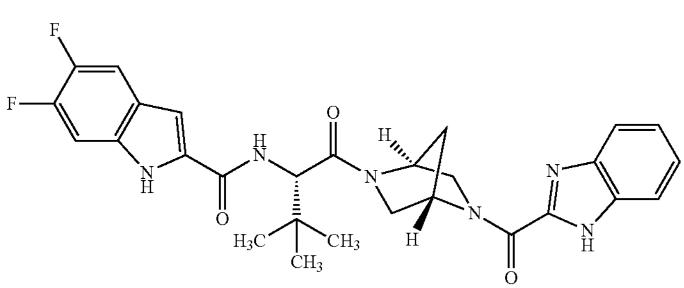 [SMILES: CC(C)(C)[C@H](NC(=O)c1cc2cc(F)c(F)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,6-difluoro-1H-indole-2-carboxamide | 535.1 |

TABLE 6-continued

| Ex # | Structure | Name | LCMS [M + 1]+ |
|---|---|---|---|
| 150 | 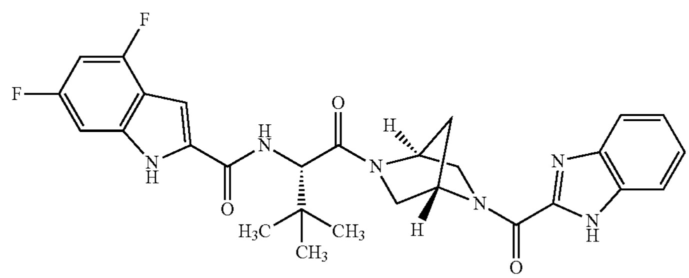 [SMILES: CC(C)(C)[C@H](NC(=O)c1cc2c(F)cc(F)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4,6-difluoro-1H-indole-2-carboxamide | 535.2 |
| 151 | 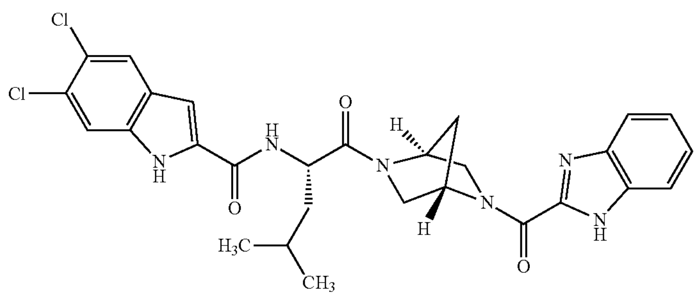 [SMILES: CC(C)C[C@H](NC(=O)c1cc2cc(Cl)c(Cl)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-dichloro-1H-indole-2-carboxamide | 567.3 |
| 152 | 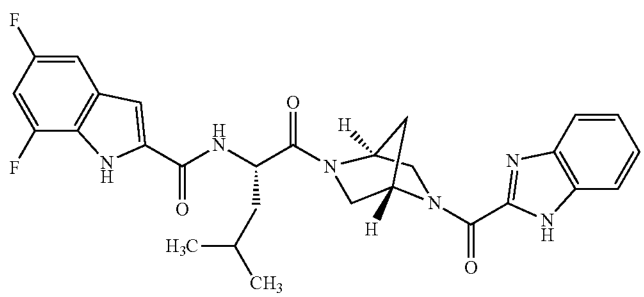 [SMILES: CC(C)C[C@H](NC(=O)c1cc2cc(F)cc(F)c2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5,7-difluoro-1H-indole-2-carboxamide | 535.3 |
| 153 | 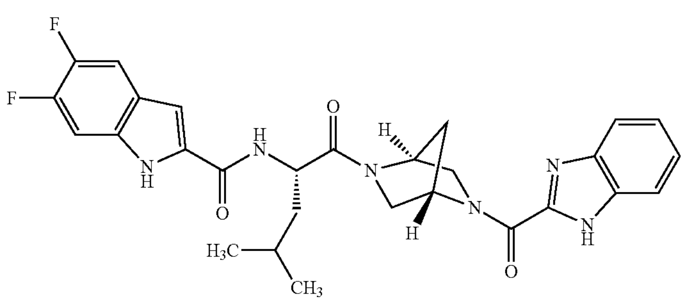 [SMILES: CC(C)C[C@H](NC(=O)c1cc2cc(F)c(F)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-difluoro-1H-indole-2-carboxamide | 535.3 |
| 154 | 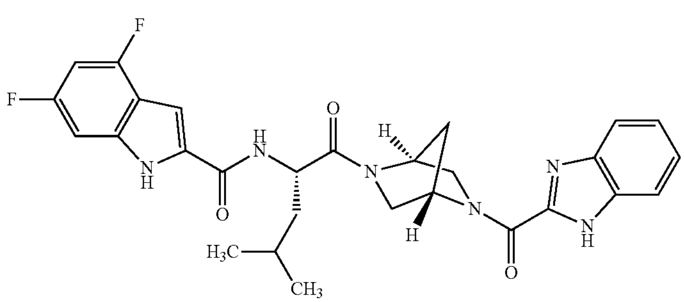 [SMILES: CC(C)C[C@H](NC(=O)c1cc2c(F)cc(F)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-4,6-difluoro-1H-indole-2-carboxamide | 535.3 |

TABLE 6-continued

| Ex # | Structure | Name | LCMS [M + 1]+ |
|---|---|---|---|
| 155 | 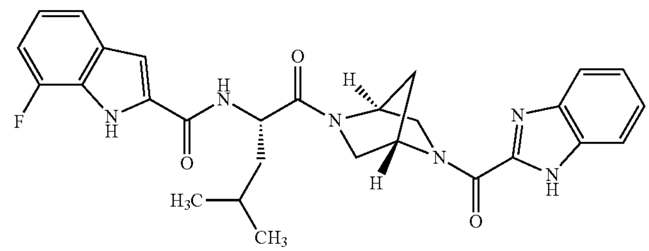 [SMILES: CC(C)C[C@H](NC(=O)c1cc2cccc(F)c2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-7-fluoro-1H-indole-2-carboxamide | 517.3 |
| 156 | 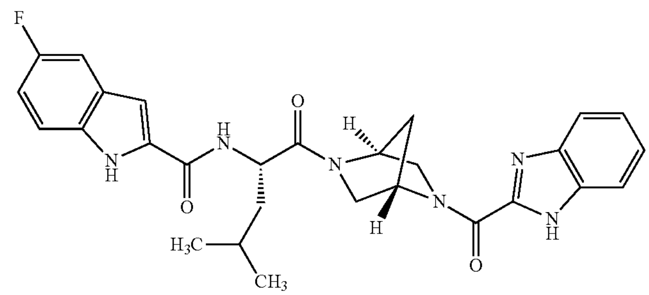 [SMILES: CC(C)C[C@H](NC(=O)c1cc2cc(F)ccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1H-indole-2-carboxamide | 517.3 |
| 157 | 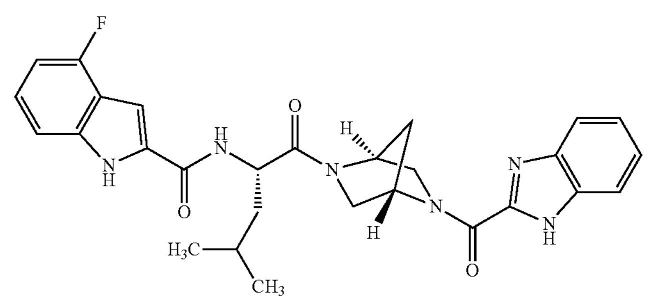 [SMILES: CC(C)C[C@H](NC(=O)c1cc2c(F)cccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-4-fluoro-1H-indole-2-carboxamide | 517.3 |
| 158 | 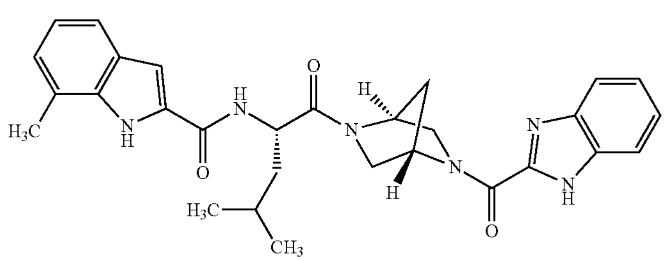 [SMILES: Cc1cccc2cc(C(=O)N[C@@H](CC(C)C)C(=O)N3C[C@@H]4C[C@H]3CN4C(=O)c3nc4ccccc4[nH]3)[nH]c12] | N-((1S)-1-{[(1S,4S)-5-(1H-benzimidazol-2-ylcarbonyl)-2,5-diazabicyclo[2.2.1]hept-2-yl]carbonyl}-3-methylbutyl)-7-methyl-1H-indole-2-carboxamide | 513.3 |
| 159 | 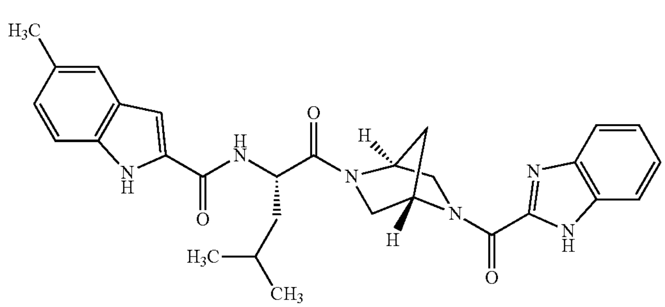 [SMILES: Cc1ccc2[nH]c(C(=O)N[C@@H](CC(C)C)C(=O)N3C[C@@H]4C[C@H]3CN4C(=O)c3nc4ccccc4[nH]3)cc2c1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5-methyl-1H-indole-2-carboxamide | 513.3 |

TABLE 6-continued

| Ex # | Structure | Name | LCMS [M + 1]+ |
|---|---|---|---|
| 160 | 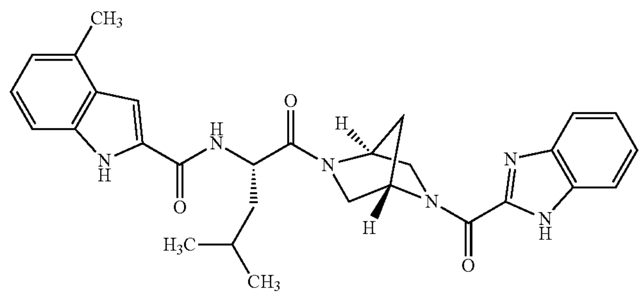 [SMILES: Cc1cccc2[nH]c(C(=O)N[C@@H](CC(C)C)C(=O)N3C[C@@H]4C[C@H]3CN4C(=O)c3nc4ccccc4[nH]3)cc12] | N-((1S)-1-{[(1S,4S)-5-(1H-benzimidazol-2-ylcarbonyl)-2,5-diazabicyclo[2.2.1]hept-2-yl]carbonyl}-3-methylbutyl)-4-methyl-1H-indole-2-carboxamide | 513.3 |
| 161 | 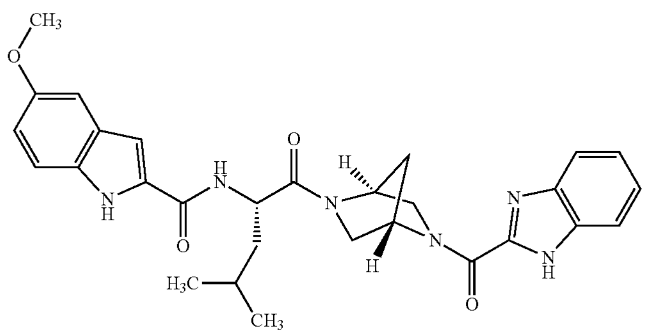 [SMILES: COc1ccc2[nH]c(C(=O)N[C@@H](CC(C)C)C(=O)N3C[C@@H]4C[C@H]3CN4C(=O)c3nc4ccccc4[nH]3)cc2c1] | N-((1S)-1-{[(1S,4S)-5-(1H-benzimidazol-2-ylcarbonyl)-2,5-diazabicyclo[2.2.1]hept-2-yl]carbonyl}-3-methylbutyl)-5-(methyloxy)-1H-indole-2-carboxamide | 529.2 |
| 162 | 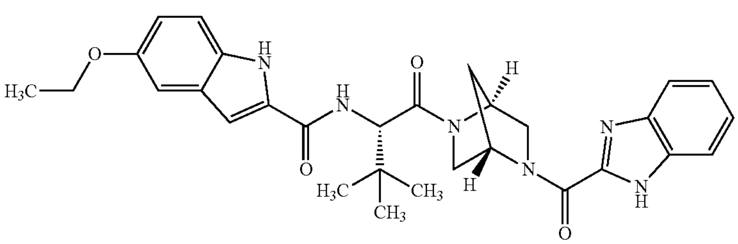 [SMILES: CCOc1ccc2[nH]c(C(=O)N[C@H](C(=O)N3C[C@@H]4C[C@H]3CN4C(=O)c3nc4ccccc4[nH]3)C(C)(C)C)cc2c1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(ethyloxy)-1H-indole-2-carboxamide | 543.1 |
| 163 | 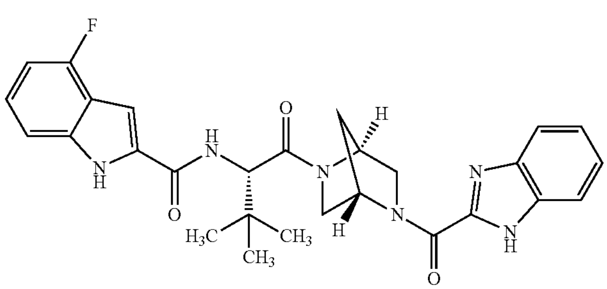 [SMILES: CC(C)(C)[C@H](NC(=O)c1cc2c(F)cccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-fluoro-1H-indole-2-carboxamide | 517.3 |
| 164 | 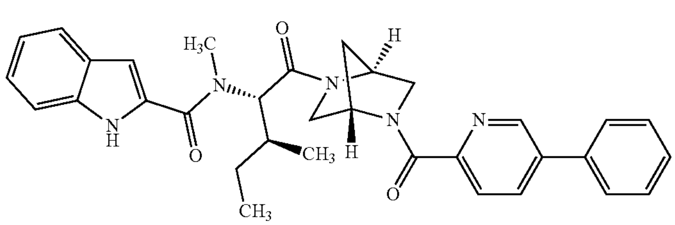 [SMILES: CC[C@H](C)[C@@H](C(=O)N1C[C@@H]2C[C@H]1CN2C(=O)c1ccc(-c2ccccc2)cn1)N(C)C(=O)c1cc2ccccc2[nH]1] | N-methyl-N-[(1S,2S)-2-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide | 550.3 |

TABLE 6-continued

| Ex # | Structure | Name | LCMS [M + 1]+ |
|---|---|---|---|
| 165 | 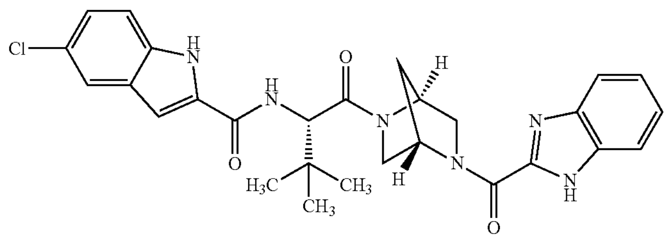 [SMILES: CC(C)(C)[C@H](NC(=O)c1cc2cc(Cl)ccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-chloro-1H-indole-2-carboxamide | 533.1 |
| 166 | 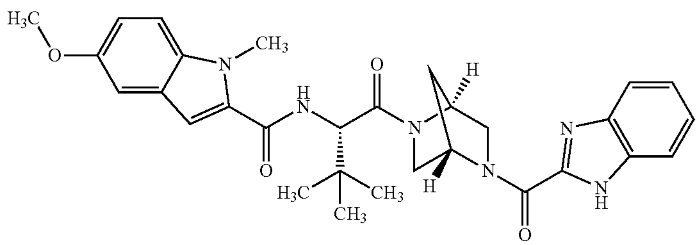 [SMILES: COc1ccc2c(c1)cc(C(=O)N[C@H](C(=O)N1C[C@@H]3C[C@H]1CN3C(=O)c1nc3ccccc3[nH]1)C(C)(C)C)n2C] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1-methyl-5-(methyloxy)-1H-indole-2-carboxamide | 543.3 |
| 167 | 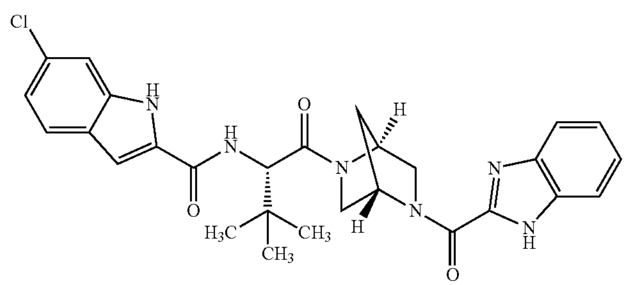 [SMILES: CC(C)(C)[C@H](NC(=O)c1cc2ccc(Cl)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-chloro-1H-indole-2-carboxamide | 533.3 |
| 168 | 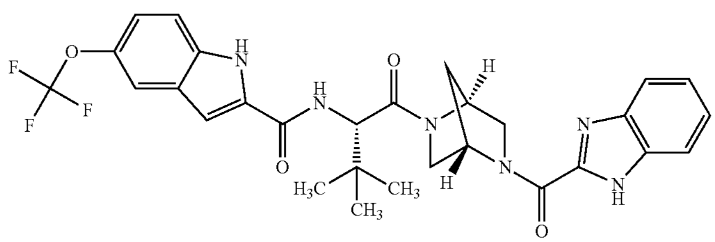 [SMILES: CC(C)(C)[C@H](NC(=O)c1cc2cc(OC(F)(F)F)ccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-[(trifluoromethyl)oxy]-1H-indole-2-carboxamide | 583.3 |
| 169 | 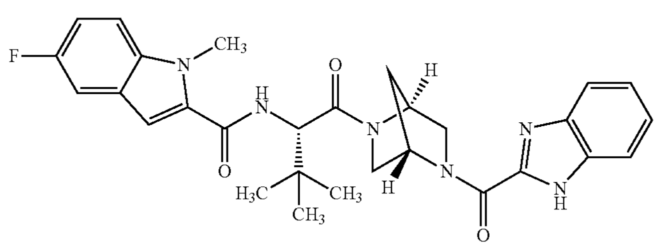 [SMILES: Cn1c(C(=O)N[C@H](C(=O)N2C[C@@H]3C[C@H]2CN3C(=O)c2nc3ccccc3[nH]2)C(C)(C)C)cc2cc(F)ccc21] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1-methyl-1H-indole-2-carboxamide | 531.1 |
| 170 | 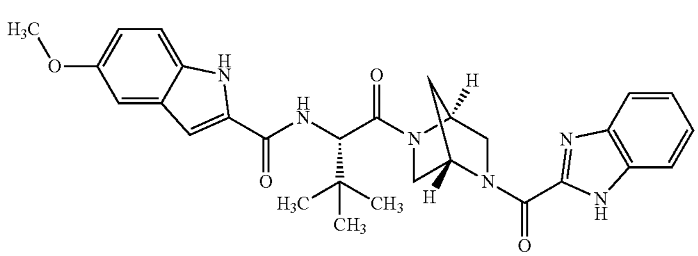 [SMILES: COc1ccc2[nH]c(C(=O)N[C@H](C(=O)N3C[C@@H]4C[C@H]3CN4C(=O)c3nc4ccccc4[nH]3)C(C)(C)C)cc2c1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(methyloxy)-1H-indole-2-carboxamide | 529.3 |

TABLE 6-continued

| Ex # | Structure | Name | LCMS [M + 1]+ |
|---|---|---|---|
| 171 | 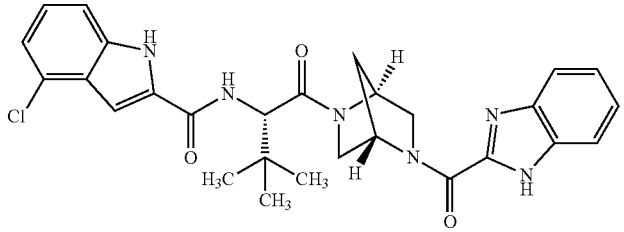 [SMILES: CC(C)(C)[C@H](NC(=O)c1cc2c(Cl)cccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-chloro-1H-indole-2-carboxamide | 533.2 |
| 172 | 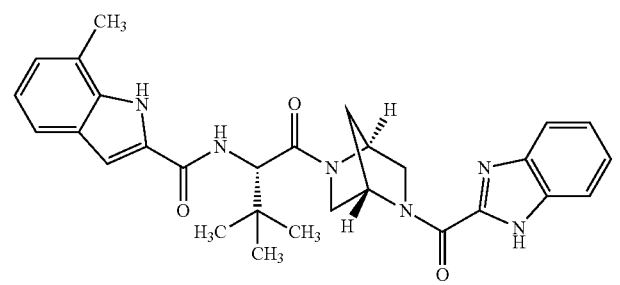 [SMILES: Cc1cccc2cc(C(=O)N[C@H](C(=O)N3C[C@@H]4C[C@H]3CN4C(=O)c3nc4ccccc4[nH]3)C(C)(C)C)[nH]c12] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-methyl-1H-indole-2-carboxamide | 513.3 |
| 173 | 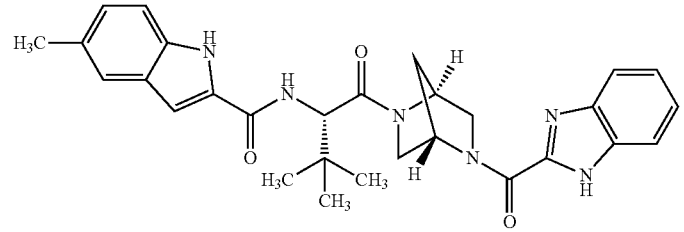 [SMILES: Cc1ccc2[nH]c(C(=O)N[C@H](C(=O)N3C[C@@H]4C[C@H]3CN4C(=O)c3nc4ccccc4[nH]3)C(C)(C)C)cc2c1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-methyl-1H-indole-2-carboxamide | 513.3 |
| 174 | 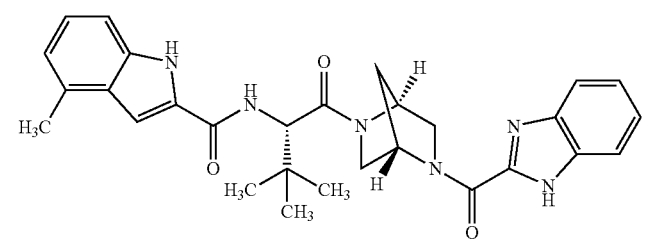 [SMILES: Cc1cccc2[nH]c(C(=O)N[C@H](C(=O)N3C[C@@H]4C[C@H]3CN4C(=O)c3nc4ccccc4[nH]3)C(C)(C)C)cc12] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-methyl-1H-indole-2-carboxamide | 513.3 |
| 175 | 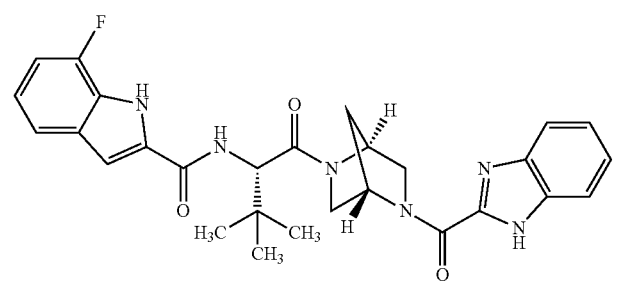 [SMILES: CC(C)(C)[C@H](NC(=O)c1cc2cccc(F)c2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-fluoro-1H-indole-2-carboxamide | 517.3 |

TABLE 6-continued

| Ex # | Structure | Name | LCMS [M + 1]+ |
|---|---|---|---|
| 176 | 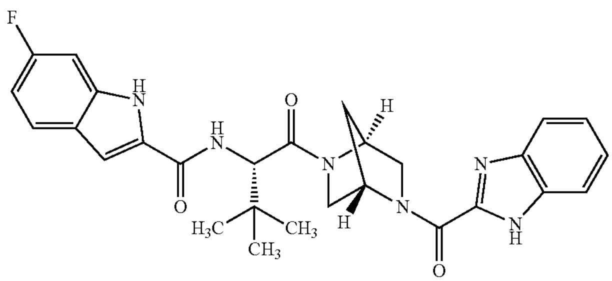 [SMILES: CC(C)(C)[C@H](NC(=O)c1cc2ccc(F)cc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-fluoro-1H-indole-2-carboxamide | 517.3 |
| 177 | 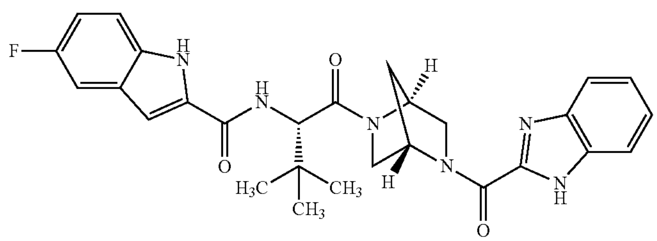 [SMILES: CC(C)(C)[C@H](NC(=O)c1cc2cc(F)ccc2[nH]1)C(=O)N1C[C@@H]2C[C@H]1CN2C(=O)c1nc2ccccc2[nH]1] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1H-indole-2-carboxamide | 517.3 |

Example 178

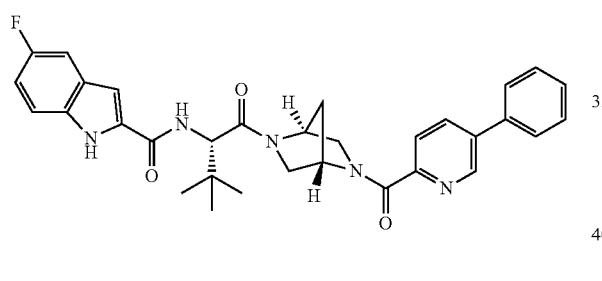

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-5-fluoro-1H-indole-2-carboxamide

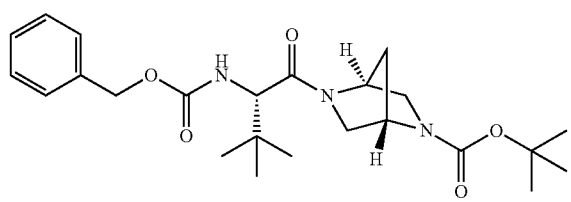 [SMILES: CC(C)(C)OC(=O)N1C[C@@H]2C[C@H]1CN2C(=O)[C@@H](NC(=O)OCc1ccccc1)C(C)(C)C]

1,1-dimethylethyl (1S,4S)-5-(3-methyl-N-{[(phenylmethyl)oxy]carbonyl}-L-valyl)-2,5-diazabicyclo[2.2.1]heptane-2-carboxylate A mixture of 3-methyl-N-{[(phenylmethyl)oxy]carbonyl}-L-valine (1.55 g, 5.84 mmol), 1,1-dimethylethyl (1S,4S)-2,5-diazabicyclo[2.2.1]heptane-2-carboxylate (1.1 g, 5.56 mmol), EDC (1.28 g, 111 mmol), HOBt (150 mg, 1.11 mmol), NMM (1.69 g, 16.7 mmol) in $CH_2Cl_2$ (20 mL) was stirred at room temperature for 18 h. The reaction was diluted with water and $CH_2Cl_2$. The two layers were separated; the organic dried over anhydrous $Na_2SO_4$ and concentrated to give the title compound (2.5 g) as a pale yellow solid. LCMS (m/z): 446.2 (M+H).

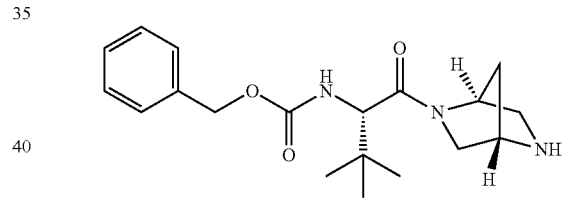

phenylmethyl {(1S)-1-[(1S,4S)-2,5-diazabicyclo[2.2.1]hept-2-ylcarbonyl]-2,2-dimethylpropyl}carbamate A solution of 1,1-dimethylethyl (1S,4S)-5-(3-methyl-N-{[(phenylmethyl)oxy]carbonyl}-L-valyl)-2,5-diazabicyclo[2.2.1]heptane-2-carboxylate (2.5 g, 5.5 mmol) in 30 ml TFA/DCM (20%) was stirred at room temperature for 1 h. The reaction mixture was made basic by addition of sodium hydroxide, then extracted with DCM (3×50 mL). The DCM was dried over anhydrous $Na_2SO_4$ and concentrated to give the title compound (1.8 g) as a pale brown oil. LCMS (m/z): 346.1 (M+H).

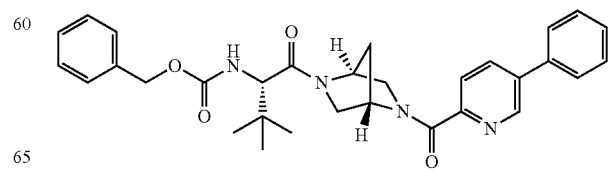

phenylmethyl [(1S)-2,2-dimethyl-1-({(1S,4S)-5-[(5-phenyl-2-pyridinyl)carbonyl]-2,5-diazabicyclo[2.2.1]hept-2-yl}carbonyl)propyl]carbamate A mixture of phenylmethyl {(1S)-1-[(1S,4S)-2,5-diazabicyclo[2.2.1]hept-2-ylcarbonyl]-2,2-dimethylpropyl}carbamate (826 mg, 2.39 mmol), 5-phenyl-2-pyridinecarboxylic acid (500 mg, 2.5 mmol), EDC (550 mg, 2.87 mmol), HOBt (65 mg, 0.48 mmol), NMM (736 mg, 7.17 mmol) in $CH_2Cl_2$ (10 mL) was stirred at room temperature for 18 h. The reaction was diluted with water and $CH_2Cl_2$. The two layers were separated; the organic dried over anhydrous $Na_2SO_4$ and concentrated to give the title compound (1.3 g) as a pale brown oil. LCMS (m/z): 527.3 (M+H).

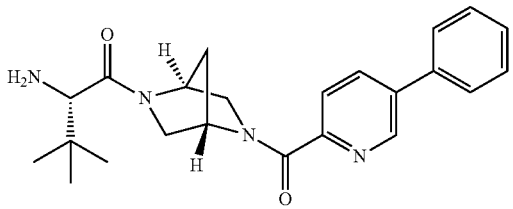 [SMILES: CC(C)(C)[C@H](N)C(=O)N1C[C@@H]2C[C@H]1CN2C(=O)c1ccc(-c2ccccc2)cn1]

[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]amine phenylmethyl [(1S)-2,2-dimethyl-1-({(1S,4S)-5-[(5-phenyl-2-pyridinyl)carbonyl]-2,5-diazabicyclo[2.2.1]hept-2-yl}carbonyl)propyl]carbamate (1.3 g, 2.47 mmol) was dissolved in methanol (40 ml). Next, 5% Pd/C (200 mg) was added under nitrogen. The reaction was hydrogenated at 45 psi under a hydrogen atmosphere for 18 h at room temperature. The reaction mixture was filtered and the filtrate concentrated to afford the title compound (0.9 g) as a yellow oil. LCMS (m/z): 393.1 (M+H).

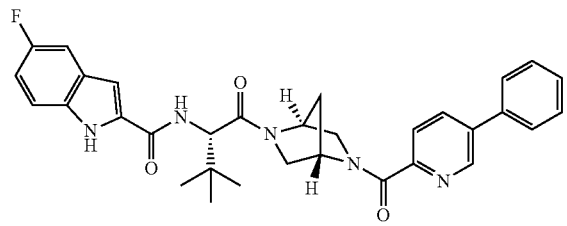 [SMILES: CC(C)(C)[C@H](NC(=O)c1cc2cc(F)ccc2[nH]1)C(=O)N1C[C@@H]2C[C@H]1CN2C(=O)c1ccc(-c2ccccc2)cn1]

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-5-fluoro-1H-indole-2-carboxamide A solution of [(1S)-2,2-dimethyl-1-({(1S,4S)-5-[(5-phenyl-2-pyridinyl)carbonyl]-2,5-diazabicyclo[2.2.1]hept-2-yl}carbonyl)propyl]amine (100 mg, 0.25 mmol), 5-fluoro-1H-indole-2-carboxylic acid (48 mg, 0.26 mmol), EDC (58 mg, 0.3 mmol), HOBt (7 mg, 0.05 mmol), NMM (77 mg, 0.76 mmol) in $CH_2Cl_2$ (3 mL) was stirred at room temperature for 2 h. The mixture was washed with 1N sodium hydroxide (2×3 mL), water (2×10 mL). The combined aqueous washes were extracted with $CH_2Cl_2$ (2×5 mL). The combined organic extracts were dried over anhydrous $Na_2SO_4$, filtered concentrated to give the crude product, which was purified by reverse phase HPLC. Concentration of the desired fractions containing product afforded the title compound (66 mg) as a pale yellow solid. LCMS (m/z): 554.3 (M+H). 1H NMR (400 MHz, CDCl$_3$) δ ppm: 0.90-1.10 (m, 9H), 1.80-2.15 (m, 2H), 3.45-4.20 (m, 4H), 4.60-5.55 (m, 3H), 6.90-7.60 (m, 10H), 7.80-8.10 (m, 2H), 8.55-8.90 (m, 1H), 9.20-9.55 (m, 1H)

Examples 179-192

The compounds in Table 7 were prepared by a method similar to the one described for the preparation of N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-5-fluoro-1H-indole-2-carboxamide (Example 178). As is appreciated by those skilled in the art, these analogous examples may involve variations in general reaction conditions.

TABLE 7

| Ex # | Structure | Name | LCMS [M + 1]$^+$ |
|---|---|---|---|
| 179 | 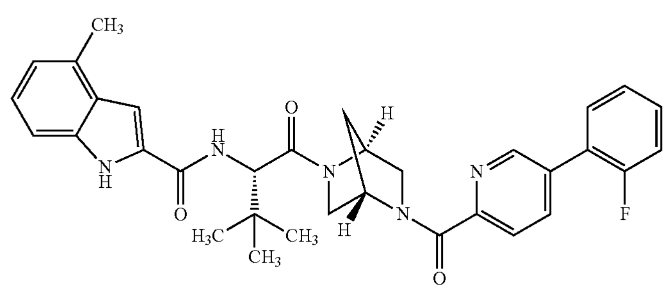 [SMILES: Cc1cccc2[nH]c(C(=O)N[C@H](C(=O)N3C[C@@H]4C[C@H]3CN4C(=O)c3ccc(-c4ccccc4F)cn3)C(C)(C)C)cc12] | N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-4-methyl-1H-indole-2-carboxamide | 568.2 |

TABLE 7-continued

| Ex # | Structure | Name | LCMS [M + 1]+ |
|---|---|---|---|
| 180 | 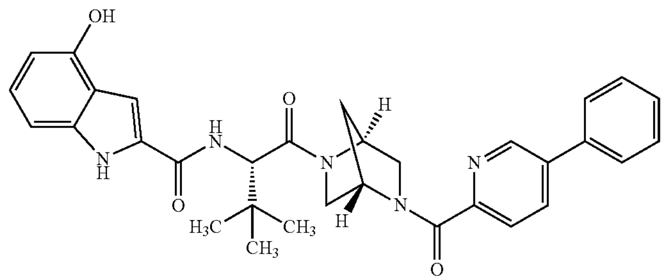 [SMILES: CC(C)(C)[C@H](NC(=O)c1cc2c(O)cccc2[nH]1)C(=O)N1C[C@@H]2C[C@H]1CN2C(=O)c1ccc(-c2ccccc2)cn1] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-hydroxy-1H-indole-2-carboxamide | 552.3 |
| 181 | 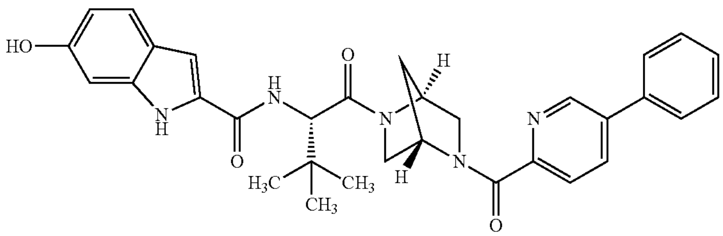 [SMILES: CC(C)(C)[C@H](NC(=O)c1cc2ccc(O)cc2[nH]1)C(=O)N1C[C@@H]2C[C@H]1CN2C(=O)c1ccc(-c2ccccc2)cn1] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-hydroxy-1H-indole-2-carboxamide | 552.3 |
| 182 | 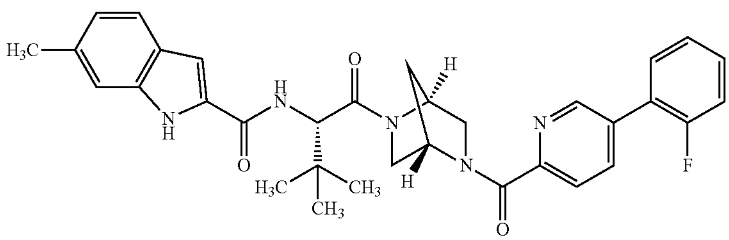 [SMILES: Cc1ccc2cc(C(=O)N[C@H](C(=O)N3C[C@@H]4C[C@H]3CN4C(=O)c3ccc(-c4ccccc4F)cn3)C(C)(C)C)[nH]c2c1] | N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-6-methyl-1H-indole-2-carboxamide | 568.3 |
| 183 | 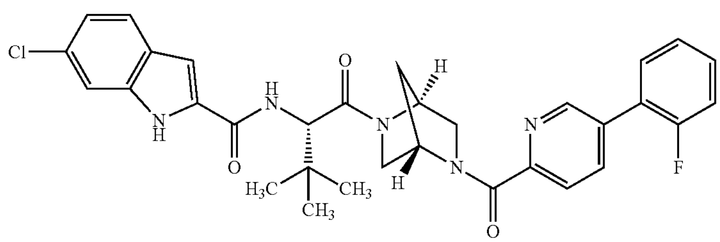 [SMILES: CC(C)(C)[C@H](NC(=O)c1cc2ccc(Cl)cc2[nH]1)C(=O)N1C[C@@H]2C[C@H]1CN2C(=O)c1ccc(-c2ccccc2F)cn1] | 6-chloro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide | 588.1 |
| 184 | 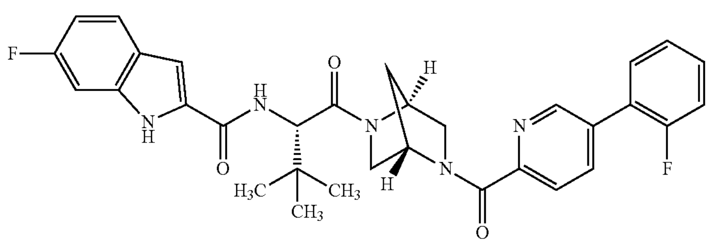 [SMILES: CC(C)(C)[C@H](NC(=O)c1cc2ccc(F)cc2[nH]1)C(=O)N1C[C@@H]2C[C@H]1CN2C(=O)c1ccc(-c2ccccc2F)cn1] | 6-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide | 572.3 |
| 185 | 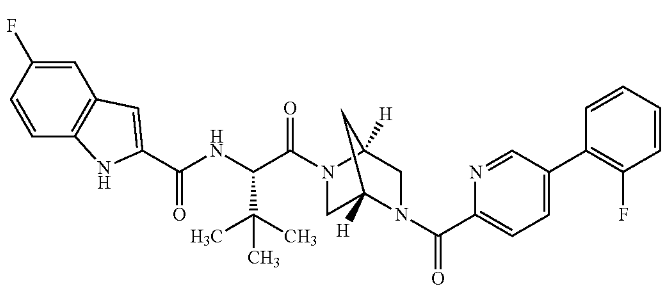 [SMILES: CC(C)(C)[C@H](NC(=O)c1cc2cc(F)ccc2[nH]1)C(=O)N1C[C@@H]2C[C@H]1CN2C(=O)c1ccc(-c2ccccc2F)cn1] | 5-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide | 572.2 |

TABLE 7-continued

| Ex # | Structure | Name | LCMS [M + 1]+ |
|---|---|---|---|
| 186 | 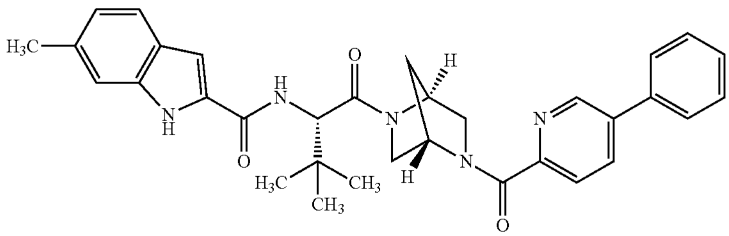 [SMILES: Cc1ccc2cc(C(=O)N[C@H](C(=O)N3C[C@@H]4C[C@H]3CN4C(=O)c3ccc(-c4ccccc4)cn3)C(C)(C)C)[nH]c2c1] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-methyl-1H-indole-2-carboxamide | 550.3 |
| 187 | 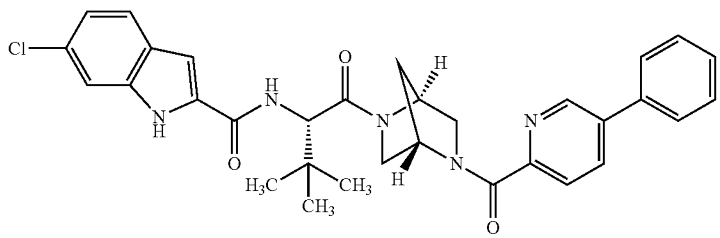 [SMILES: CC(C)(C)[C@H](NC(=O)c1cc2ccc(Cl)cc2[nH]1)C(=O)N1C[C@@H]2C[C@H]1CN2C(=O)c1ccc(-c2ccccc2)cn1] | 6-chloro-N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide | 570.3 |
| 188 | 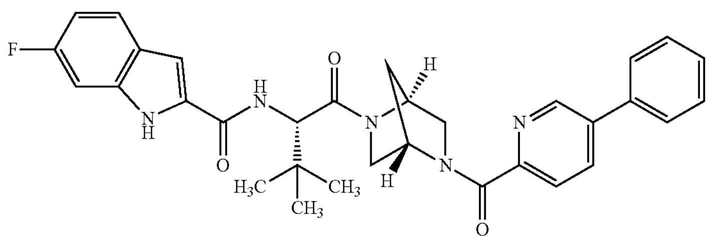 [SMILES: CC(C)(C)[C@H](NC(=O)c1cc2ccc(F)cc2[nH]1)C(=O)N1C[C@@H]2C[C@H]1CN2C(=O)c1ccc(-c2ccccc2)cn1] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-fluoro-1H-indole-2-carboxamide | 554.3 |
| 189 | 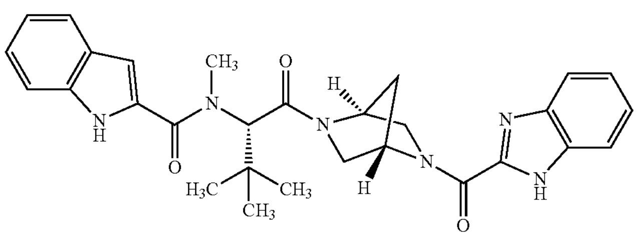 [SMILES: CN(C(=O)c1cc2ccccc2[nH]1)[C@H](C(=O)N1C[C@@H]2C[C@H]1CN2C(=O)c1nc2ccccc2[nH]1)C(C)(C)C] | N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-N-methyl-1H-indole-2-carboxamide | 513.3 |
| 190 | 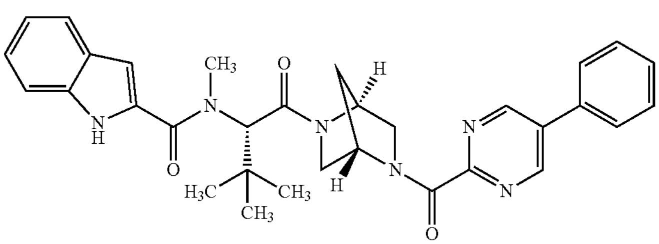 [SMILES: CN(C(=O)c1cc2ccccc2[nH]1)[C@H](C(=O)N1C[C@@H]2C[C@H]1CN2C(=O)c1ncc(-c2ccccc2)cn1)C(C)(C)C] | N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-N-methyl-1H-indole-2-carboxamide} | 551.2 |
| 191 | 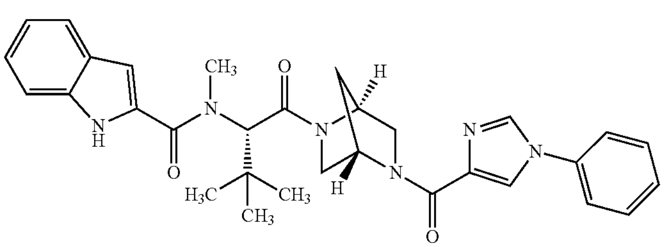 [SMILES: CN(C(=O)c1cc2ccccc2[nH]1)[C@H](C(=O)N1C[C@@H]2C[C@H]1CN2C(=O)c1cn(-c2ccccc2)cn1)C(C)(C)C] | N-[(1S)-2,2-dimethyl-1-({(1S,4S)-5-[(1-phenyl-1H-imidazol-4-yl)carbonyl]-2,5-diazabicyclo[2.2.1]hept-2-yl}carbonyl)propyl]-N-methyl-1H-indole-2-carboxamide | 539.3 |

TABLE 7-continued

| Ex # | Structure | Name | LCMS [M + 1]+ |
|---|---|---|---|
| 192 | 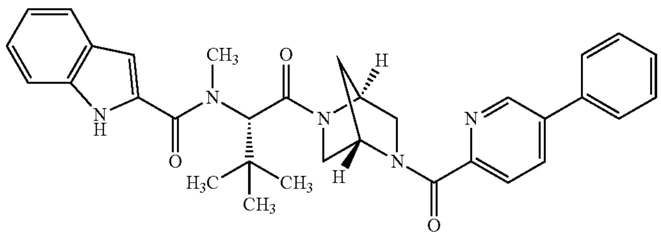 [SMILES: CN(C(=O)c1cc2ccccc2[nH]1)[C@H](C(=O)N1C[C@@H]2C[C@H]1CN2C(=O)c1ccc(-c2ccccc2)cn1)C(C)(C)C] | N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-methyl-1H-indole-2-carboxamide | 550.2 |

Example 193

N-((1S)-1-{[(1S,4S)-5-({5-[4-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide A mixture of N-{(1S)-1-[(1S,4S)-2,5-diazabicyclo[2.2.1]hept-2-ylcarbonyl]-2,2-dimethylpropyl}-1H-indole-2-carboxamide (5 g, 14.11 mmol), 5-bromo-2-pyridinecarboxylic acid (2.85 g, 14.11 mmol), EDC (2.7 g, 14.11 mmol), HOBt (1.91 g, 14.11 mmol), NMM (2.14 g, 21.14 mmol) in CH$_2$Cl$_2$ (50 mL) was stirred at room temperature for 12 h. The reaction was diluted with water. The two layers were separated and the organic washed with sat. NaHCO$_3$ and 1N HCl. The resulting organic solution was dried over anhydrous Na$_2$SO$_4$ and concentrated to give the title compound (7 g) as a yellow solid. LCMS (m/z): 540.2 (M+H).

N-((1S)-1-{[(1S,4S)-5-({5-[4-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide A mixture of N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide (100 mg, 0.186 mmol), [4-(dimethylamino)phenyl]boronic acid (31 mg, 0.186 mmol), Pd(Ph$_3$P)$_4$ (10 mg, 0.009 mmol), potassium carbonate (26 mg, 0.186 mmol) in toluene (6 mL), ethanol (2 mL), and water (0.5 mL) was heated to 80° C. for 10 h under a nitrogen atmosphere. The solution was concentrated and the resulting residue was purified by reverse phase HPLC. Concentration of the desired fractions containing product afforded the title compound (45 mg) as a pale brown solid. LCMS (m/z): 579.3 (M+H). 1H NMR (400 MHz, CDCl$_3$) δ ppm: 0.90-1.20 (m, 9H), 1.80-2.20 (m, 2H), 2.90-3.15 (m, 6H), 3.50-4.20 (m, 4H), 4.60-5.60 (m, 4H), 6.90-7.70 (m, 9H), 7.80-8.10 (m, 2H), 8.60-8.85 (m, 1H), 9.15-9.45 (m, 1H)

Examples 194-213

The compounds in Table 8 were prepared by a method similar to the one described for the preparation of N-((1S)-1-{[(1S,4S)-5-({5-[4-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide (Example 193). As is appreciated by those skilled in the art, these analogous examples may involve variations in general reaction conditions.

TABLE 8

| Ex # | Structure | Name | LCMS [M + 1]+ |
|---|---|---|---|
| 194 | 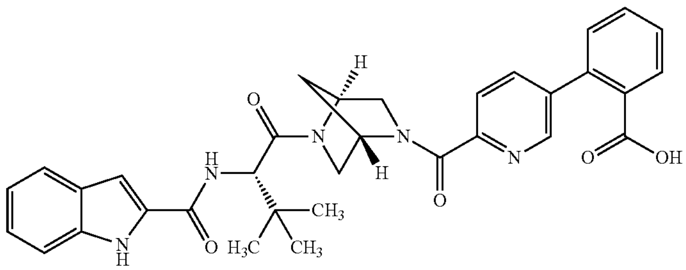 [SMILES: CC(C)(C)[C@H](NC(=O)c1cc2ccccc2[nH]1)C(=O)N1C[C@@H]2C[C@H]1CN2C(=O)c1ccc(-c2ccccc2C(=O)O)cn1] | 2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic acid | 580.3 |
| 195 | 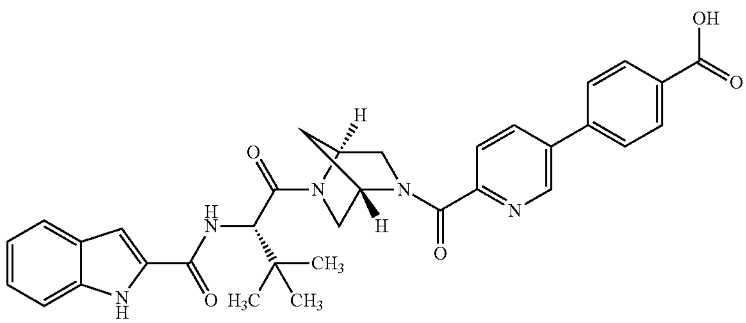 [SMILES: CC(C)(C)[C@H](NC(=O)c1cc2ccccc2[nH]1)C(=O)N1C[C@@H]2C[C@H]1CN2C(=O)c1ccc(-c2ccc(C(=O)O)cc2)cn1] | 4-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic acid | 580.3 |
| 196 | 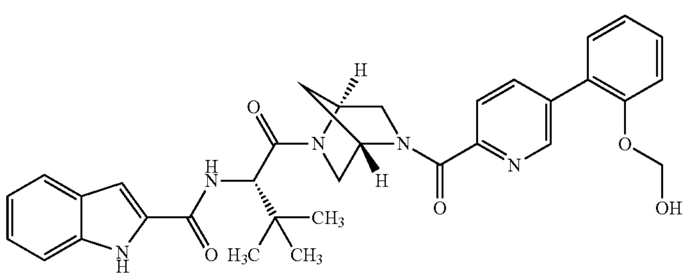 [SMILES: CC(C)(C)[C@H](NC(=O)c1cc2ccccc2[nH]1)C(=O)N1C[C@@H]2C[C@H]1CN2C(=O)c1ccc(-c2ccccc2OCO)cn1] | N-((1S)-1-{[(1S,4S)-5-({5-[2-(ethyloxy)phenyl]-2-pyridinyl}carbonyl)-2,5-diazabicyclo[2.2.1]hept-2-yl]carbonyl}-2,2-dimethylpropyl)-1H-indole-2-carboxamide | 580.3 |
| 197 | 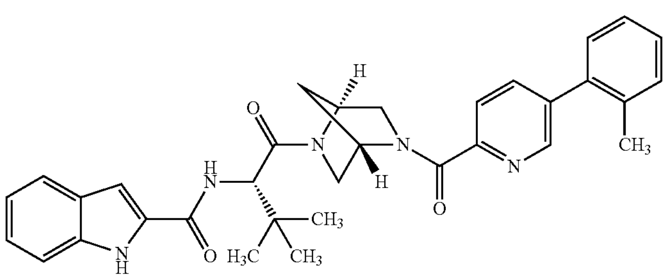 [SMILES: Cc1ccccc1-c1ccc(C(=O)N2C[C@@H]3C[C@H]2CN3C(=O)[C@@H](NC(=O)c2cc3ccccc3[nH]2)C(C)(C)C)nc1] | N-{(1S)-2,2-dimethyl-1-[((1S,4S)-5-{[5-(2-methylphenyl)-2-pyridinyl]carbonyl}-2,5-diazabicyclo[2.2.1]hept-2-yl)carbonyl]propyl}-1H-indole-2-carboxamide | 550.3 |
| 198 | 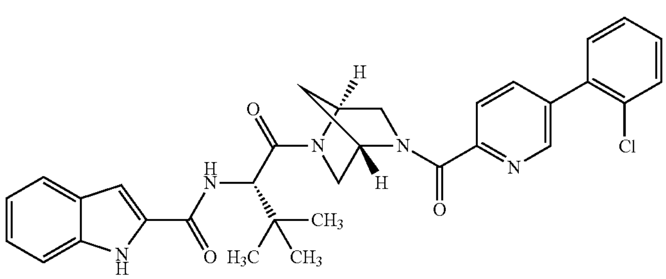 [SMILES: CC(C)(C)[C@H](NC(=O)c1cc2ccccc2[nH]1)C(=O)N1C[C@@H]2C[C@H]1CN2C(=O)c1ccc(-c2ccccc2Cl)cn1] | N-{(1S)-1-[((1S,4S)-5-{[5-(2-chlorophenyl)-2-pyridinyl]carbonyl}-2,5-diazabicyclo[2.2.1]hept-2-yl)carbonyl]-2,2-dimethylpropyl}-1H-indole-2-carboxamide | 570.2 |

TABLE 8-continued

| Ex # | Structure | Name | LCMS [M + 1]+ |
|---|---|---|---|
| 199 | 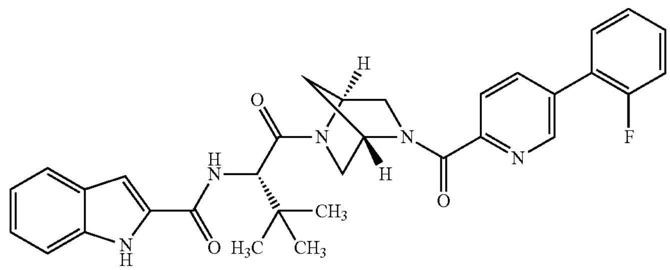 [SMILES: CC(C)(C)[C@H](NC(=O)c1cc2ccccc2[nH]1)C(=O)N1C[C@@H]2C[C@H]1CN2C(=O)c1ccc(-c2ccccc2F)cn1] | N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide | 554.3 |
| 200 | 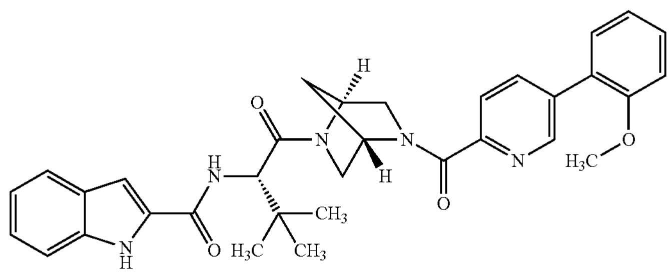 [SMILES: COc1ccccc1-c1ccc(C(=O)N2C[C@@H]3C[C@H]2CN3C(=O)[C@@H](NC(=O)c2cc3ccccc3[nH]2)C(C)(C)C)nc1] | N-((1S)-2,2-dimethyl-1-{[(1S,4S)-5-({5-[2-(methyloxy)phenyl]-2-pyridinyl}carbonyl)-2,5-diazabicyclo[2.2.1]hept-2-yl]carbonyl}propyl)-1H-indole-2-carboxamide | 566.2 |
| 201 | 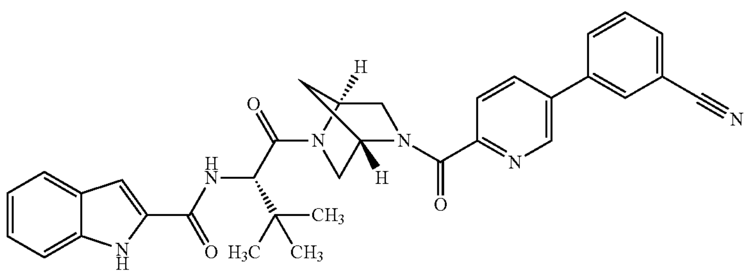 [SMILES: CC(C)(C)[C@H](NC(=O)c1cc2ccccc2[nH]1)C(=O)N1C[C@@H]2C[C@H]1CN2C(=O)c1ccc(-c2cccc(C#N)c2)cn1] | N-{(1S)-1-[((1S,4S)-5-{[5-(3-cyanophenyl)-2-pyridinyl]carbonyl}-2,5-diazabicyclo[2.2.1]hept-2-yl)carbonyl]-2,2-dimethylpropyl}-1H-indole-2-carboxamide | 561.3 |
| 202 | 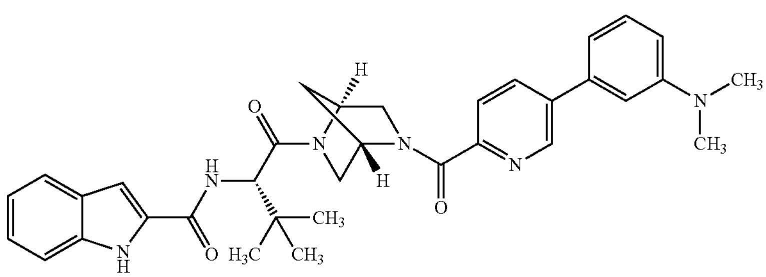 [SMILES: CN(C)c1cccc(-c2ccc(C(=O)N3C[C@@H]4C[C@H]3CN4C(=O)[C@@H](NC(=O)c3cc4ccccc4[nH]3)C(C)(C)C)nc2)c1] | N-((1S)-1-{[(1S,4S)-5-({5-[3-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide | 579.4 |
| 203 | 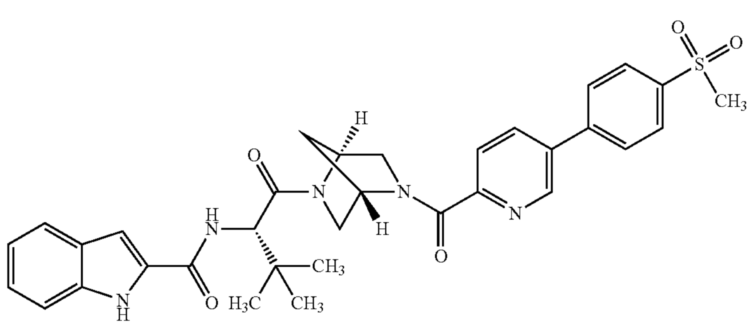 [SMILES: CC(C)(C)[C@H](NC(=O)c1cc2ccccc2[nH]1)C(=O)N1C[C@@H]2C[C@H]1CN2C(=O)c1ccc(-c2ccc(S(C)(=O)=O)cc2)cn1] | N-((1S)-2,2-dimethyl-1-{[(1S,4S)-5-({5-[4-(methylsulfonyl)phenyl]-2-pyridinyl}carbonyl)-2,5-diazabicyclo[2.2.1]hept-2-yl]carbonyl}propyl)-1H-indole-2-carboxamide | 614.3 |

TABLE 8-continued

| Ex # | Structure | Name | LCMS [M + 1]+ |
|---|---|---|---|
| 204 | 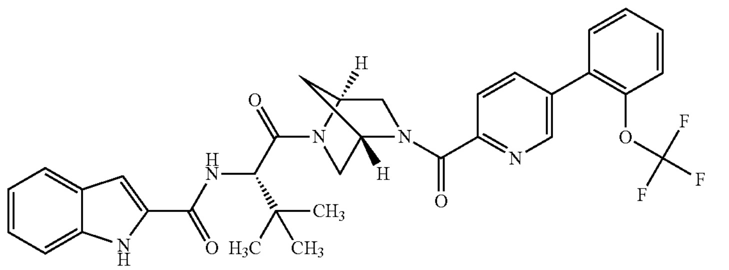 [SMILES: CC(C)(C)[C@H](NC(=O)c1cc2ccccc2[nH]1)C(=O)N1C[C@@H]2C[C@H]1CN2C(=O)c1ccc(-c2ccccc2OC(F)(F)F)cn1] | N-[(1S)-2,2-dimthyl-1-({(1S,4S)-5-[(5-{2-[(trifluoromethyl)oxy]phenyl}-2-pyridinyl)carbonyl]-2,5-diazabicyclo[2.2.1]hept-2-yl}carbonyl)propyl]-1H-indole-2-carboxamide | 620.3 |
| 205 | 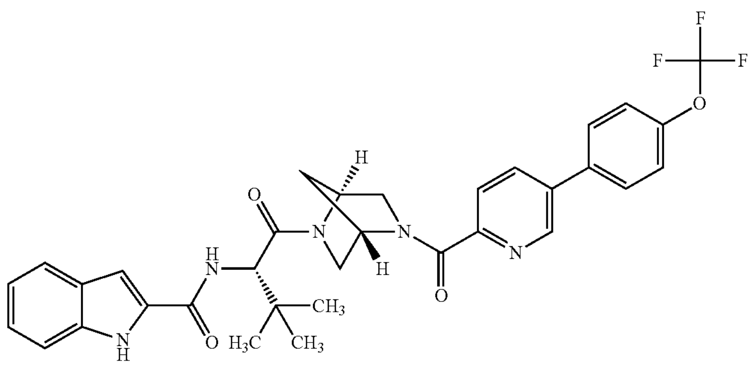 [SMILES: CC(C)(C)[C@H](NC(=O)c1cc2ccccc2[nH]1)C(=O)N1C[C@@H]2C[C@H]1CN2C(=O)c1ccc(-c2ccc(OC(F)(F)F)cc2)cn1] | N-[(1S)-2,2-dimethyl-1-({(1S,4S)-5-[(5-{4-[(trifluoromethyl)oxy]phenyl}-2-pyridinyl)carbonyl]-2,5-diazabicyclo[2.2.1]hept-2-yl}carbonyl)propyl]-1H-indole-2-carboxamide | 620.3 |
| 206 | 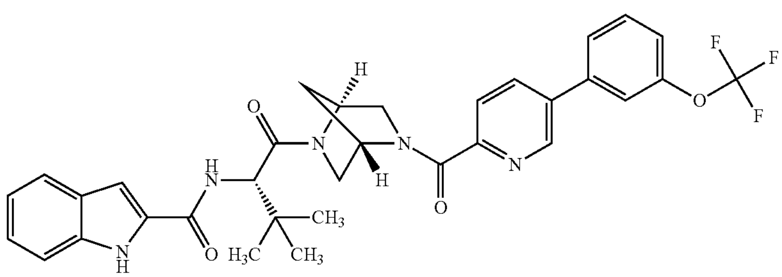 [SMILES: CC(C)(C)[C@H](NC(=O)c1cc2ccccc2[nH]1)C(=O)N1C[C@@H]2C[C@H]1CN2C(=O)c1ccc(-c2cccc(OC(F)(F)F)c2)cn1] | N-[(1S)-2,2-dimethyl-1-({(1S,4S)-5-[(5-{3-[(trifluoromethyl)oxy]phenyl}-2-pyridinyl)carbonyl]-2,5-diazabicyclo[2.2.1]hept-2-yl}carbonyl)propyl]-1H-indole-2-carboxamide | 620.3 |
| 207 | 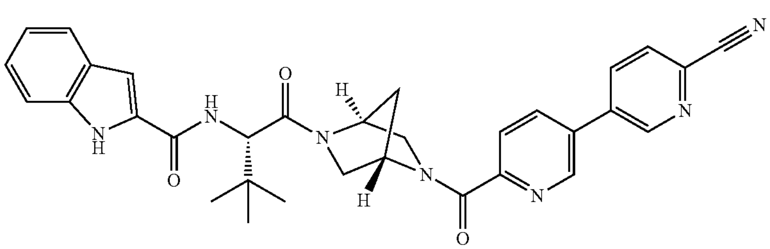 [SMILES: CC(C)(C)[C@H](NC(=O)c1cc2ccccc2[nH]1)C(=O)N1C[C@@H]2C[C@H]1CN2C(=O)c1ccc(-c2ccc(C#N)nc2)cn1] | N-[(1S)-1-({(1S,4S)-5-[(6'-cyano-3,3'-bipyridin-6-yl)carbonyl]-2,5-diazabicyclo[2.2.1]hept-2-yl}carbonyl)-2,2-dimethylpropyl]-1H-indole-2-carboxamide | 562.3 |
| 208 | 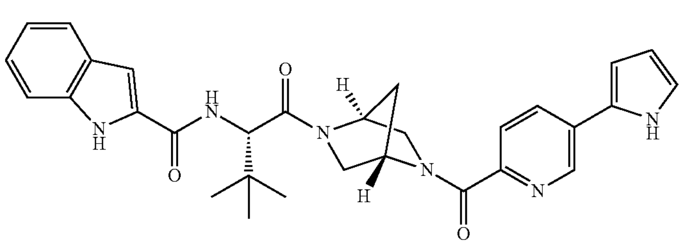 [SMILES: CC(C)(C)[C@H](NC(=O)c1cc2ccccc2[nH]1)C(=O)N1C[C@@H]2C[C@H]1CN2C(=O)c1ccc(-c2ccc[nH]2)cn1] | N-{(1S)-2,2-dimethyl-1-[((1S,4S)-5-{[5-(1H-pyrrol-2-yl)-2-pyridinyl]carbonyl}-2,5-diazabicyclo[2.2.1]hept-2-yl)carbonyl]propyl}-1H-indole-2-carboxamide | 525.3 |

TABLE 8-continued

| Ex # | Structure | Name | LCMS [M + 1]+ |
|---|---|---|---|
| 209 | 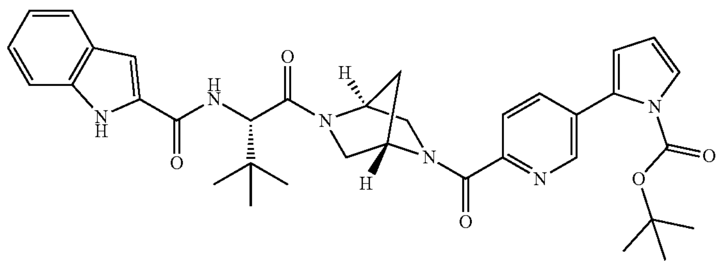 [SMILES: CC(C)(C)OC(=O)n1cccc1-c1ccc(C(=O)N2C[C@@H]3C[C@H]2CN3C(=O)[C@@H](NC(=O)c2cc3ccccc3[nH]2)C(C)(C)C)nc1] | 1,1-dimethylethyl 2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]-1H-pyrrole-1-carboxylate | 625.3 |
| 210 | 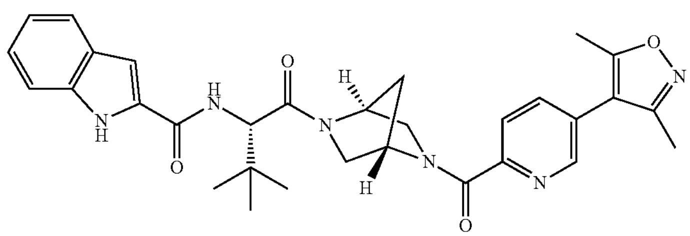 [SMILES: Cc1noc(C)c1-c1ccc(C(=O)N2C[C@@H]3C[C@H]2CN3C(=O)[C@@H](NC(=O)c2cc3ccccc3[nH]2)C(C)(C)C)nc1] | N-{(1S)-1-[((1S,4S)-5-{[5-(3,5-dimethyl-4-isoxazolyl)-2-pyridinyl]carbonyl}-2,5-diazabicyclo[2.2.1]hept-2-yl)carbonyl]-2,2-dimethylpropyl}-1H-indole-2-carboxamide | 555.3 |
| 211 | 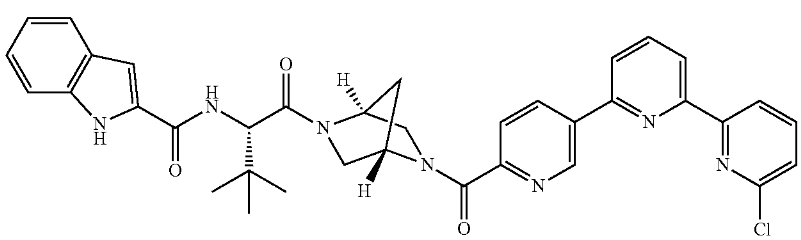 [SMILES: CC(C)(C)[C@H](NC(=O)c1cc2ccccc2[nH]1)C(=O)N1C[C@@H]2C[C@H]1CN2C(=O)c1ccc(-c2cccc(-c3cccc(Cl)n3)n2)cn1] | N-[(1S)-1-({(1S,4S)-5-[(6-chloro-2,2':6',3''-terpyridin-6''-yl)carbonyl]-2,5-diazabicyclo[2.2.1]hept-2-yl}carbonyl)-2,2-dimethylpropyl]-1H-indole-2-carboxamide | 648.2 |
| 212 | 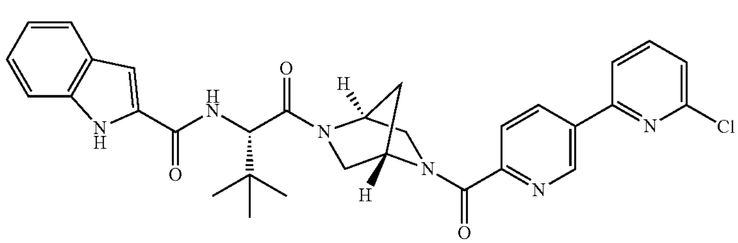 [SMILES: CC(C)(C)[C@H](NC(=O)c1cc2ccccc2[nH]1)C(=O)N1C[C@@H]2C[C@H]1CN2C(=O)c1ccc(-c2cccc(Cl)n2)cn1] | N-[(1S)-1-({(1S,4S)-5-[(6-chloro-2,3'-bipyridin-6'-yl)carbonyl]-2,5-diazabicyclo[2.2.1]hept-2-yl}carbonyl)-2,2-dimethylpropyl]-1H-indole-2-carboxamide | 571.2 |
| 213 | 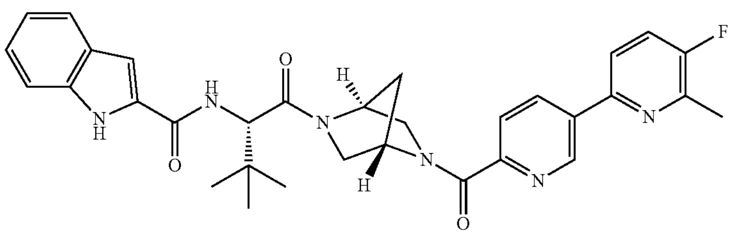 [SMILES: Cc1nc(-c2ccc(C(=O)N3C[C@@H]4C[C@H]3CN4C(=O)[C@@H](NC(=O)c3cc4ccccc4[nH]3)C(C)(C)C)nc2)ccc1F] | N-[(1S)-1-({(1S,4S)-5-[(5-fluoro-6-methyl-2,3'-bipyridin-6'-yl)carbonyl]-2,5-diazabicyclo[2.2.1]hept-2-yl}carbonyl)-2,2-dimethylpropyl]-1H-indole-2-carboxamide | 569.3 |

Example 214

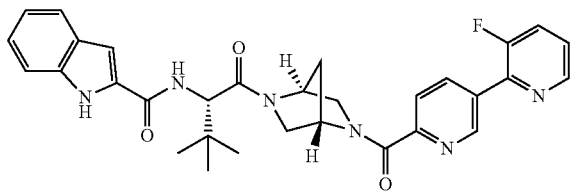 [SMILES: CC(C)(C)[C@H](NC(=O)c1cc2ccccc2[nH]1)C(=O)N1C[C@@H]2C[C@H]1CN2C(=O)c1ccc(-c2ncccc2F)cn1]

N-[(1S)-1-({(1S,4S)-5-[(3-fluoro-2,3'-bipyridin-6'-yl)carbonyl]-2,5-diazabicyclo[2.2.1]hept-2-yl}carbonyl)-2,2-dimethylpropyl]-1H-indole-2-carboxamide

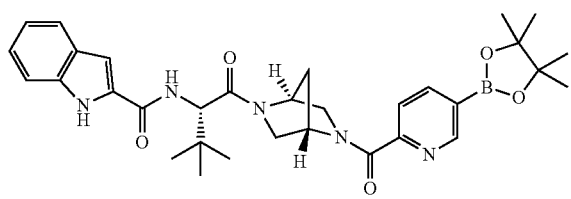 [SMILES: CC(C)(C)[C@H](NC(=O)c1cc2ccccc2[nH]1)C(=O)N1C[C@@H]2C[C@H]1CN2C(=O)c1ccc(B2OC(C)(C)C(C)(C)O2)cn1]

N-{(1S)-2,2-dimethyl-1-[((1S,4S)-5-{[5-(4,4,5,5-tetramethyl-1,3,2-dioxaborolan-2-yl)-2-pyridinyl]carbonyl}-2,5-diazabicyclo[2.2.1]hept-2-yl)carbonyl]propyl}-1H-indole-2-carboxamide A mixture of N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide (600 mg, 1.1 mmol), bis(pinacolato)diboron (624 mg, 1.67 mmol), Pd(dppf)Cl$_2$ (60 mg, 0.073 mmol), potassium acetate (327 mg, 3.33 mmol) was refluxed in dry 1,4-dioxane (10 mL) under a nitrogen atmosphere for 16 h. After completion, the mixture was cooled to room temperature, diluted with water (60 mL) and extracted with EtOAc (3×18 mL). The organic layer was dried over Na$_2$SO$_4$, filtered and concentrated to give the title compound (800 mg) as a black oil. LCMS (m/z): 504.2 (M-81).

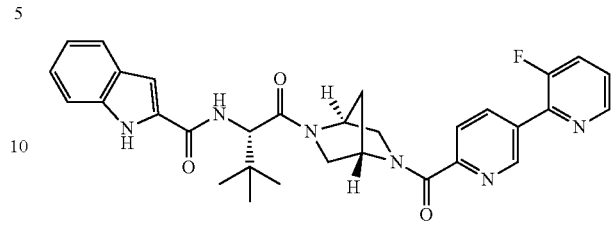

N-[(1S)-1-({(1S,4S)-5-[(3-fluoro-2,3'-bipyridin-6'-yl)carbonyl]-2,5-diazabicyclo[2.2.1]hept-2-yl}carbonyl)-2,2-dimethylpropyl]-1H-indole-2-carboxamide A mixture of N-{(1S)-2,2-dimethyl-1-[((1S,4S)-5-{[5-(4,4,5,5-tetramethyl-1,3,2-dioxaborolan-2-yl)-2-pyridinyl]carbonyl}-2,5-diazabicyclo[2.2.1]hept-2-yl)carbonyl]propyl}-1H-indole-2-carboxamide (150 mg, 0.26 mmol), 2-bromo-3-fluoropyridine (69 mg, 0.38 mmol), Pd(dppf)Cl$_2$ (15 mg, 0.018 mmol), sodium carbonate (55 mg, 0.52 mmol) in dry 1,4-dioxane (2 mL) and water (1 mL) was refluxed for 16 h under a nitrogen atmosphere. The solution was concentrated and the resulting residue was purified by reverse phase HPLC. Concentration of the desired fractions containing product afforded the title compound (21 mg) as a pale brown solid. LCMS (m/z): 555.3 (M+H). 1H NMR (400 MHz, CDCl$_3$) δ ppm: 0.90-1.10 (m, 9H), 1.80-2.25 (m, 2H), 3.50-4.30 (m, 4H), 4.15-5.10 (m, 3H), 7.00-7.75 (m, 8H), 7.95-8.70 (m, 3H), 9.00-9.30 (m, 1H), 9.40-9.70 (m, 1H)

Examples 215-217

The compounds in Table 7 were prepared by a method similar to the one described for the preparation of N-[(1S)-1-({(1S,4S)-5-[(3-fluoro-2,3'-bipyridin-6'-yl)carbonyl]-2,5-diazabicyclo[2.2.1]hept-2-yl}carbonyl)-2,2-dimethylpropyl]-1H-indole-2-carboxamide (Example 214). As is appreciated by those skilled in the art, these analogous examples may involve variations in general reaction conditions.

TABLE 9

| Ex # | Structure | Name | LCMS [M + 1]$^+$ |
|---|---|---|---|
| 215 | 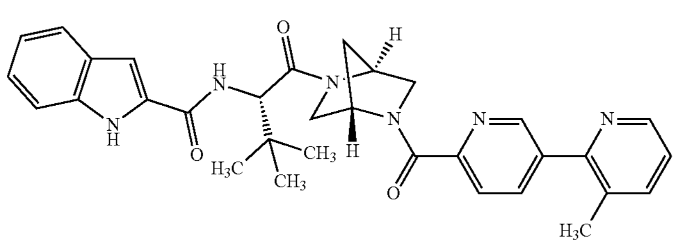 [SMILES: Cc1cccnc1-c1ccc(C(=O)N2C[C@@H]3C[C@H]2CN3C(=O)[C@@H](NC(=O)c2cc3ccccc3[nH]2)C(C)(C)C)nc1] | N-[(1S)-2,2-dimethyl-1-({(1S,4S)-5-[(3-methyl-2,3'-bipyridin-6'-yl)carbonyl]-2,5-diazabicyclo[2.2.1]hept-2-yl}carbonyl)propyl]-1H-indole-2-carboxamide | 551.3 |

| Ex # | Structure | Name | LCMS [M + 1]+ |
|---|---|---|---|
| 216 | 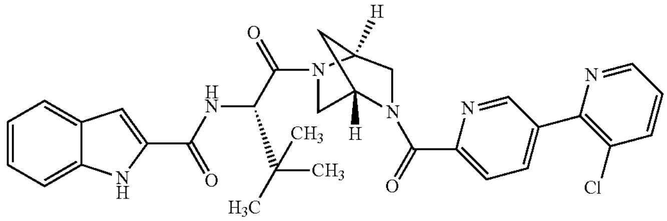 [SMILES: CC(C)(C)[C@H](NC(=O)c1cc2ccccc2[nH]1)C(=O)N1C[C@@H]2C[C@H]1CN2C(=O)c1ccc(-c2ncccc2Cl)cn1] | N-[(1S)-1-({(1S,4S)-5-[(3-chloro-2,3'-bipyridin-6'-yl)carbonyl]-2,5-diazabicyclo[2.2.1]hept-2-yl}carbonyl)-2,2-dimethylpropyl]-1H-indole-2-carboxamide | 571.2 |
| 217 | 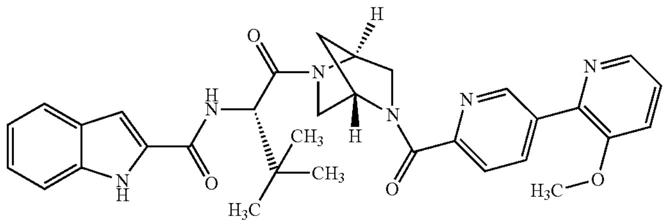 [SMILES: COc1cccnc1-c1ccc(C(=O)N2C[C@@H]3C[C@H]2CN3C(=O)[C@@H](NC(=O)c2cc3ccccc3[nH]2)C(C)(C)C)nc1] | N-{(1S)-2,2-dimethyl-1-[((1S,4S)-5-{[3-(methyloxy)-2,3'-bipyridin-6'-yl]carbonyl}-2,5-diazabicyclo[2.2.1]hept-2-yl)carbonyl]propyl}-1H-indole-2-carboxamide | 567.3 |

The invention claimed is:
1. A compound selected from the group consisting of:
N-((1S)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide;
N-[(1S)-2,2-dimethyl-1-({(1S,4S)-5-[(5-phenyl-2-thienyl)carbonyl]-2,5-diazabicyclo[2.2.1]hept-2-yl}carbonyl)propyl]-1H-indole-2-carboxamide;
N-[(1S)-1-({(1S,4S)-5-[(2R)-2,3-dihydro-1H-indol-2-yl)carbonyl]-2,5-diazabicyclo[2.2.1]hept-2-yl}carbonyl)-2,2-dimethylpropyl]-1H-indole-2-carboxamide;
N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;
N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;
N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;
N-((1S)-1-{[(1S,4S)-5-(1H-indazol-3-ylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(1H-indol-7-ylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(1H-indol-6-ylcarbonyl)-2,5-diazabicyclo[2.2.1]hept-2-yl]carbonyl}-2,2-dimethylpropyl)-1H-indole-2-carboxamide;
N-[(1S)-2,2-dimethyl-1-({(1S,4S)-5-[(7-methyl-1H-indol-2-yl)carbonyl]-2,5-diazabicyclo[2.2.1]hept-2-yl}carbonyl)propyl]-1H-indole-2-carboxamide;
N-{(1S)-2,2-dimethyl-1-[((1S,4S)-5-{[5-(methyloxy)-1H-indol-2-yl]carbonyl}-2,5-diazabicyclo[2.2.1]hept-2-yl)carbonyl]propyl}-1H-indole-2-carboxamide;
N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide;
N-[(1S)-1-({(1S,4S)-5-[(5-fluoro-1H-indol-2-yl)carbonyl]-2,5-diazabicyclo[2.2.1]hept-2-yl}carbonyl)-2,2-dimethylpropyl]-1H-indole-2-carboxamide;
N-((1S)-1-{[(1S,4S)-5-(1H-indol-4-ylcarbonyl)-2,5-diazabicyclo[2.2.1]hept-2-yl]carbonyl}-2,2-dimethylpropyl)-1H-indole-2-carboxamide;
N-[(1S)-2,2-dimethyl-1-({(1S,4S)-5-[(1-methyl-1H-indol-2-yl)carbonyl]-2,5-diazabicyclo[2.2.1]hept-2-yl]carbonyl)propyl]-1H-indole-2-carboxamide;
N-((1S)-1-{[(1S,4S)-5-(1H-indol-3-ylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(1H-indol-5-ylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(1-benzothien-2-ylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;
N-((1S)-1-{[(1S,4S)-5-(1-benzofuran-2-ylcarbonyl)-2,5-diazabicyclo[2.2.1]hept-2-yl]carbonyl}-2,2-dimethylpropyl)-1H-indole-2-carboxamide;
N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide;
N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide;
N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide;
N-{(1S)-2,2-dimethyl-1-[((1S,4S)-5-{[4-(methyloxy)-1H-indol-2-yl]carbonyl}-2,5-diazabicyclo[2.2.1]hept-2-yl)carbonyl]propyl}-1H-indole-2-carboxamide;
N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide;
N-[(1S)-1-({(1S,4S)-5-[(1,1-dioxido-1,2-benzisothiazol-2(3H)-yl)acetyl]-2,5-diazabicyclo[2.2.1]hept-2-yl}carbonyl)-2,2-dimethylpropyl]-1H-indole-2-carboxamide;
N-{(1S)-2,2-dimethyl-1-[((1S,4S)-5-{[1-(phenylsulfonyl)-1H-indol-2-yl]carbonyl}-2,5-diazabicyclo[2.2.1]hept-2-yl)carbonyl]propyl}-1H-indole-2-carboxamide;
N-[(1S)-1-({(1S,4S)-5-[(5-chloro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(4,5-dimethyl-2-thienyl)carbonyl]-2,5-diazabicyclo[2.2.1]hept-2-yl}carbonyl)-2,2-dimethylpropyl]-1H-indole-2-carboxamide;
N-[(1S)-1-({(1S,4S)-5-[(2,6-dichloro-3-pyridinyl)carbonyl]-2,5-diazabicyclo[2.2.1]hept-2-yl}carbonyl)-2,2-dimethylpropyl]-1H-indole-2-carboxamide;
N-[(1S)-1-({(1S,4S)-5-[(4-chloro-1H-indol-2-yl)carbonyl]-2,5-diazabicyclo[2.2.1]hept-2-yl}carbonyl)-2,2-dimethylpropyl]-1H-indole-2-carboxamide;
N-[(1S)-2,2-dimethyl-1-({(1S,4S)-5-[(4-methyl-1H-indol-2-yl)carbonyl]-2,5-diazabicyclo[2.2.1]hept-2-yl}carbonyl)propyl]-1H-indole-2-carboxamide;
N-[(1S)-2,2-dimethyl-1-({(1S,4S)-5-[(5-phenyl-1,3-oxazol-4-yl)carbonyl]-2,5-diazabicyclo[2.2.1]hept-2-yl}carbonyl)propyl]-1H-indole-2-carboxamide;
N-[(1S)-2,2-dimethyl-1-({(1S,4S)-5-[(2-phenyl-1,3-oxazol-4-yl)carbonyl]-2,5-diazabicyclo[2.2.1]hept-2-yl}carbonyl)propyl]-1H-indole-2-carboxamide;
N-((1S)-2,2-dimethyl-1-{[(1S,4S)-5-(1H-pyrrolo[3,2-b]pyridin-2-ylcarbonyl)-2,5-diazabicyclo[2.2.1]hept-2-yl]carbonyl}propyl)-1H-indole-2-carboxamide;
N-((1S)-2,2-dimethyl-1-{[(1S,4S)-5-(pyrazolo[1,5-a]pyridin-2-ylcarbonyl)-2,5-diazabicyclo[2.2.1]hept-2-yl]carbonyl}propyl)-1H-indole-2-carboxamide;
methyl 2-({(1S,4S)-5-[N-(1H-indol-2-ylcarbonyl)-3-methyl-L-valyl]-2,5-diazabicyclo[2.2.1]hept-2-yl}carbonyl)-1H-indole-5-carboxylate;
N-((1S)-1-{[(1S,4S)-5-(1-benzothien-2-ylacetyl)-2,5-diazabicyclo[2.2.1]hept-2-yl]carbonyl}-2,2-dimethylpropyl)-1H-indole-2-carboxamide;
N-{(1S)-2,2-dimethyl-1-[((1S,4S)-5-{[5-(methyloxy)-1H-benzimidazol-2-yl]carbonyl}-2,5-diazabicyclo[2.2.1]hept-2-yl)carbonyl]propyl}-1H-indole-2-carboxamide;
N-((1S)-2,2-dimethyl-1-{[(1S,4S)-5-(1H-pyrrolo[2,3-b]pyridin-2-ylcarbonyl)-2,5-diazabicyclo[2.2.1]hept-2-yl]carbonyl}propyl)-1H-indole-2-carboxamide;
N-((1S)-2,2-dimethyl-1-{[(1S,4S)-5-({5-methyl-2-[4-(methyloxy)phenyl]-1,3-oxazol-4-yl}carbonyl)-2,5-diazabicyclo[2.2.1]hept-2-yl]carbonyl}propyl)-1H-indole-2-carboxamide;
N-{(1S)-1-[((1S,4S)-5-{[6-(dimethylamino)-1H-indol-2-yl]carbonyl}-2,5-diazabicyclo[2.2.1]hept-2-yl)carbonyl]-2,2-dimethylpropyl}-1H-indole-2-carboxamide;
N-[(1S)-2,2-dimethyl-1-({(1S,4S)-5-[(2-phenyl-1H-imidazol-4-yl)carbonyl]-2,5-diazabicyclo[2.2.1]hept-2-yl}carbonyl)propyl]-1H-indole-2-carboxamide;
N-{(1S)-2,2-dimethyl-1-[((1S,4S)-5-{[2-phenyl-5-(trifluoromethyl)-1,3-oxazol-4-yl]carbonyl}-2,5-diazabicyclo[2.2.1]hept-2-yl)carbonyl]propyl}-1H-indole-2-carboxamide;
N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;
N-{(1S)-2,2-dimethyl-1-[((1S,4S)-5-{[4-(4-morpholinyl)-2-pyridinyl]carbonyl}-2,5-diazabicyclo[2.2.1]hept-2-yl)carbonyl]propyl}-1H-indole-2-carboxamide;
N-{(1S)-2,2-dimethyl-1-[((1S,4S)-5-{[6-(1-pyrrolidinyl)-2-pyridinyl]carbonyl}-2,5-diazabicyclo[2.2.1]hept-2-yl)carbonyl]propyl}-1H-indole-2-carboxamide;
N-((1S)-2,2-dimethyl-1-{[(1S,4S)-5-({5-[(phenylamino)carbonyl]-2-pyridinyl}carbonyl)-2,5-diazabicyclo[2.2.1]hept-2-yl]carbonyl}propyl)-1H-indole-2-carboxamide;
N-((1S)-1-{[(1S,4S)-5-(3-isoquinolinylcarbonyl)-2,5-diazabicyclo[2.2.1]hept-2-yl]carbonyl}-2,2-dimethylpropyl)-1H-indole-2-carboxamide;
N-{(1S)-2,2-dimethyl-1-[((1S,4S)-5-{[5-(1-pyrrolidinylcarbonyl)-2-pyridinyl]carbonyl}-2,5-diazabicyclo[2.2.1]hept-2-yl)carbonyl]propyl}-1H-indole-2-carboxamide;
N-((1S)-2,2-dimethyl-1-{[(1S,4S)-5-(1,3-thiazol-4-ylcarbonyl)-2,5-diazabicyclo[2.2.1]hept-2-yl]carbonyl}propyl)-1H-indole-2-carboxamide;
N-((1S)-2,2-dimethyl-1-{[(1S,4S)-5-(1,3-thiazol-5-ylcarbonyl)-2,5-diazabicyclo[2.2.1]hept-2-yl]carbonyl}propyl)-1H-indole-2-carboxamide;
N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1H-indole-2-carboxamide;
N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-1H-indole-2-carboxamide;
N-{(1S)-2,2-dimethyl-1-[((1S,4S)-5-{[5-(4-pyridinyl)-1H-indol-2-yl]carbonyl}-2,5-diazabicyclo[2.2.1]hept-2-yl)carbonyl]propyl}-1H-indole-2-carboxamide;
N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide;
6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxamide;
methyl 6'-({(1S,4S)-5-[N-(1H-indol-2-ylcarbonyl)-3-methyl-L-valyl]-2,5-diazabicyclo[2.2.1]hept-2-yl}carbonyl)-2,3'-bipyridine-5-carboxylate;
N-{(1S)-2,2-dimethyl-1-[((1S,4S)-5-{[5-(1H-tetrazol-5-yl)-2,3'-bipyridin-6'-yl]carbonyl}-2,5-diazabicyclo[2.2.1]hept-2-yl)carbonyl]propyl}-1H-indole-2-carboxamide;
N-{(1S)-1-[((1S,4S)-5-{[5-(4-cyanophenyl)-2-pyridinyl]carbonyl}-2,5-diazabicyclo[2.2.1]hept-2-yl)carbonyl]-2,2-dimethylpropyl}-1H-indole-2-carboxamide;
N-methyl-N-[(1S)-2-methyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;
N-methyl-N-[(1S)-3-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide;
N-methyl-N-((1S)-1-methyl-2-oxo-2-{(1S,4S)-5-[(5-phenyl-2-pyridinyl)carbonyl]-2,5-diazabicyclo[2.2.1]hept-2-yl}ethyl)-1H-indole-2-carboxamide;
N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-ethyl-1H-indole-2-carboxamide;
N-{(1S)-2,2-dimethyl-1-[((1S,4S)-5-{[5-(1-pyrrolidinyl)-2-pyridinyl]carbonyl}-2,5-diazabicyclo[2.2.1]hept-2-yl)carbonyl]propyl}-1H-indole-2-carboxamide;
N-{(1S)-1-[((1S,4S)-5-{[5-(1-hydroxycyclohexyl)-2-pyridinyl]carbonyl}-2,5-diazabicyclo[2.2.1]hept-2-yl)carbonyl]-2,2-dimethylpropyl}-1H-indole-2-carboxamide;
N-{(1S)-2,2-dimethyl-1-[((1S,4S)-5-{[5-(4-morpholinyl)-2-pyridinyl]carbonyl}-2,5-diazabicyclo[2.2.1]hept-2-yl)carbonyl]propyl}-1H-indole-2-carboxamide;
N-[(1S)-2,2-dimethyl-1-({(1S,4S)-5-[(5-phenyl-2-pyrazinyl)carbonyl]-2,5-diazabicyclo[2.2.1]hept-2-yl}carbonyl)propyl]-1H-indole-2-carboxamide;
N-[(1S)-2,2-dimethyl-1-({(1S,4S)-5-[(5-phenyl-1,3-oxazol-2-yl)carbonyl]-2,5-diazabicyclo[2.2.1]hept-2-yl}carbonyl)propyl]-1H-indole-2-carboxamide;
N-{(1S)-2,2-dimethyl-1-[((1S,4S)-5-{[6-(4-morpholinyl)-1H-indol-2-yl]carbonyl}-2,5-diazabicyclo[2.2.1]hept-2-yl)carbonyl]propyl}-1H-indole-2-carboxamide;

N-[(1S)-1-({(1S,4S)-5-[(6-amino-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-ethyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclopentyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(1-methylethyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(2-methylpropyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(phenyloxy)-2-pyridinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(4-phenyl-1H-pyrrol-2-yl)carbonyl]-2,5-diazabicyclo[2.2.1]hept-2-yl}carbonyl)propyl]-1H-indole-2-carboxamide;

N-((1S)-1-{[(1S,4S)-5-(3,3'-bipyridin-6-ylcarbonyl)-2,5-diazabicyclo[2.2.1]hept-2-yl]carbonyl}-2,2-dimethylpropyl)-1H-indole-2-carboxamide;

N-{(1S)-1-[((1S,4S)-5-{[5-(2,6-dimethyl-4-morpholinyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-2,2-dimethyl-1-({(1S,4S)-5-[(6-methyl-5-phenyl-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(4-methyl-5-phenyl-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(3-methyl-5-phenyl-2-pyridinyl)carbonyl]-2,5-diazabicyclo[2.2.1]hept-2-yl}carbonyl)propyl]-1H-indole-2-carboxamide;

N-((1S,2S)-2-methyl-1-{[(1S,4S)-5-({5-[2-(methyloxy)phenyl]-2-pyrimidinyl}carbonyl)-2,5-diazabicyclo[2.2.1]hept-2-yl]carbonyl}butyl)-1H-indole-2-carboxamide;

N-{(1S,2S)-1-[((1S,4S)-5-{[5-(2-fluorophenyl)-2-pyrimidinyl]carbonyl}-2,5-diazabicyclo[2.2.1]hept-2-yl)carbonyl]-2-methylbutyl}-1H-indole-2-carboxamide;

N-[(1S,2S)-2-methyl-1-({(1S,4S)-5-[(5-phenyl-2-pyrimidinyl)carbonyl]-2,5-diazabicyclo[2.2.1]hept-2-yl}carbonyl)butyl]-1H-indole-2-carboxamide;

N-((1S)-2,2-dimethyl-1-{[(1S,4S)-5-({5-[2-(methyloxy)phenyl]-2-pyrimidinyl}carbonyl)-2,5-diazabicyclo[2.2.1]hept-2-yl]carbonyl}propyl)-1H-indole-2-carboxamide;

N-{(1S)-1-[((1S,4S)-5-{[5-(2-fluorophenyl)-2-pyrimidinyl]carbonyl}-2,5-diazabicyclo[2.2.1]hept-2-yl)carbonyl]-2,2-dimethylpropyl}-1H-indole-2-carboxamide;

N-{(1S)-2,2-dimethyl-1-[((1S,4S)-5-{[5-(1-piperidinyl)-2-pyrimidinyl]carbonyl}-2,5-diazabicyclo[2.2.1]hept-2-yl)carbonyl]propyl}-1H-indole-2-carboxamide;

N-((1S)-1-{[(1S,4S)-5-({5-[4-(1-hydroxy-1-methylethyl)phenyl]-2-pyridinyl}carbonyl)-2,5-diazabicyclo[2.2.1]hept-2-yl]carbonyl}-2,2-dimethylpropyl)-1H-indole-2-carboxamide;

N-((1S)-1-{[(1S,4S)-5-({5-[4-(1,1-dimethylethyl)-1-piperazinyl]-2-pyridinyl}carbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(4-methyl-1-piperazinyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(4-ethyl-1-piperazinyl)-2-pyridinyl]carbonyl}-2,5-diazabicyclo[2.2.1]hept-2-yl)carbonyl]-2,2-dimethylpropyl}-1H-indole-2-carboxamide;

N-((1S)-2,2-dimethyl-1-{[(1S,4S)-5-({5-[4-(methylsulfonyl)-1-piperazinyl]-2-pyridinyl}carbonyl)-2,5-diazabicyclo[2.2.1]hept-2-yl]carbonyl}propyl)-1H-indole-2-carboxamide;

N-{(1S)-2,2-dimethyl-1-[((1S,4S)-5-{[5-(1-piperidinyl)-2-pyridinyl]carbonyl}-2,5-diazabicyclo[2.2.1]hept-2-yl)carbonyl]propyl}-1H-indole-2-carboxamide;

N-{(1S)-2,2-dimethyl-1-[((1S,4S)-5-{[5-(2-pyrimidinyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(3,6-dihydro-2H-pyran-4-yl)-2-pyridinyl]carbonyl}-2,5-diazabicyclo[2.2.1]hept-2-yl)carbonyl]-2,2-dimethylpropyl}-1H-indole-2-carboxamide;

N-{(1S)-1-[((1S,4S)-5-{[5-(1-cyclohexen-1-yl)-2-pyridinyl]carbonyl}-2,5-diazabicyclo[2.2.1]hept-2-yl)carbonyl]-2,2-dimethylpropyl}-1H-indole-2-carboxamide;

7-fluoro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-7-fluoro-1H-indole-2-carboxamide;

7-fluoro-N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;

7-fluoro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(2S)-2,3-dihydro-1H-indol-2-ylcarbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-butyl-2-pyridinyl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(trifluoromethyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[2-(4-chlorophenyl)-5-methyl-1,3-oxazol-4-yl]carbonyl}-2,5-diazabicyclo[2.2.1]hept-2-yl)carbonyl]-2,2-dimethylpropyl}-1H-indole-2-carboxamide;

N-((1S)-1-{[(1S,4S)-5-(1,3-benzoxazol-2-ylcarbonyl)-2,5-diazabicyclo[2.2.1]hept-2-yl]carbonyl}-2,2-dimethylpropyl)-1H-indole-2-carboxamide;

N-[(1S)-2,2-dimethyl-1-({(1S,4S)-5-[(5-phenyl-1H-pyrrol-2-yl)carbonyl]-2,5-diazabicyclo[2.2.1]hept-2-yl}carbonyl)propyl]-1H-indole-2-carboxamide;

N-[(1S)-1-({(1S,4S)-5-[(5-bromo-2-pyridinyl)carbonyl]-2,5-diazabicyclo[2.2.1]hept-2-yl}carbonyl)-2,2-dimethylpropyl]-1H-indole-2-carboxamide;

N-[(1S)-2,2-dimethyl-1-({(1R,4R)-5-[(5-phenyl-2-pyridinyl)carbonyl]-2,5-diazabicyclo[2.2.1]hept-2-yl}carbonyl)propyl]-1H-indole-2-carboxamide;

N-((1S)-1-{[(1S,4S)-5-(3-biphenylylcarbonyl)-2,5-diazabicyclo[2.2.1]hept-2-yl]carbonyl}-2,2-dimethylpropyl)-1H-indole-2-carboxamide;

N-[(1S)-1-({(1S,4S)-5-[(4-chloro-3-biphenylyl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[1-(2-pyridinyl)-4-piperidinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(1-phenyl-1H-imidazol-4-yl)carbonyl]-2,5-diazabicyclo[2.2.1]hept-2-yl}carbonyl)propyl]-1H-indole-2-carboxamide;

N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-7-fluoro-1H-indole-2-carboxamide;

N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-7-fluoro-1H-indole-2-carboxamide;

N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-7-fluoro-1H-indole-2-carboxamide;

N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-7-fluoro-1H-indole-2-carboxamide;

7-fluoro-N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(6-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-{(1S)-2,2-dimethyl-1-[((1S,4S)-5-{[6-(methyloxy)-1H-indol-2-yl]carbonyl}-2,5-diazabicyclo[2.2.1]hept-2-yl)carbonyl]propyl}-1H-indole-2-carboxamide;

6-chloro-N-[(1S)-2,2-dimethyl-1-({(1S,4S)-5-[(6-methyl-1H-indol-2-yl)carbonyl]-2,5-diazabicyclo[2.2.1]hept-2-yl}carbonyl)propyl]-1H-indole-2-carboxamide;

6-chloro-N-[(1S)-1-({(1S,4S)-5-[(4-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(7-fluoro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-[(1S)-1-({(1S,4S)-5-[(6-chloro-1H-indol-2-yl)carbonyl]-2,5-diazabicyclo[2.2.1]hept-2-yl}carbonyl)-2,2-dimethylpropyl]-1H-indole-2-carboxamide;

6-chloro-N-((1S)-1-{[(1S,4S)-5-(2-indolizinylcarbonyl)-2,5-diazabicyclo[2.2.1]hept-2-yl]carbonyl}-2,2-dimethylpropyl)-1H-indole-2-carboxamide;

6-chloro-N-[(1S)-2,2-dimethyl-1-({(1S,4S)-5-[(5-methyl-1H-indol-2-yl)carbonyl]-2,5-diazabicyclo[2.2.1]hept-2-yl}carbonyl)propyl]-1H-indole-2-carboxamide;

6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;

6-chloro-N-{(1S)-2,2-dimethyl-1-[((1S,4S)-5-{[7-(methyloxy)-1H-indol-2-yl]carbonyl}-2,5-diazabicyclo[2.2.1]hept-2-yl)carbonyl]propyl}-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-methyl-1H-indole-2-carboxamide;

N-((1R)-1-{[(1S,4S)-5-(1H-indol-2-ylcarbonyl)-2,5-diazabicyclo[2.2.1]hept-2-yl]carbonyl}-2,2-dimethylpropyl)-1H-indole-2-carboxamide;

N-[(1S)-1-({(1S,4S)-5-[(5-cyclohexyl-2-pyridinyl)carbonyl]-2,5-diazabicyclo[2.2.1]hept-2-yl}carbonyl)-2-methylpropyl]-1H-indole-2-carboxamide;

N-[(1S)-2-[(1S,4S)-5-[(5-cyclohexyl-2-pyridinyl)carbonyl]-2,5-diazabicyclo[2.2.1]hept-2-yl]-2-oxo-1-(phenylmethyl)ethyl]-1H-indole-2-carboxamide;

N-[(1S,2S)-1-({(1S,4S)-5-[(5-cyclohexyl-2-pyridinyl)carbonyl]-2,5-diazabicyclo[2.2.1]hept-2-yl}carbonyl)-2-methylbutyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-methyl-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-5-fluoro-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-5-fluoro-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-7-fluoro-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-7-fluoro-1H-indole-2-carboxamide;

N-[(1S)-2-[(1S,4S)-5-(1H-benzimidazol-2-ylcarbonyl)-2,5-diazabicyclo[2.2.1]hept-2-yl]-2-oxo-1-(phenylmethyl)ethyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2-methylpropyl)-1H-indole-2-carboxamide;

N-((1S,2S)-1-{[(1S,4S)-5-(1H-benzimidazol-2-ylcarbonyl)-2,5-diazabicyclo[2.2.1]hept-2-yl]carbonyl}-2-methylbutyl)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,7-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-dichloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,7-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4,6-difluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-7-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-4-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-3-methylbutyl)-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(ethyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-fluoro-1H-indole-2-carboxamide;

N-methyl-N-[(1S,2S)-2-methyl-1-({(1S,4S)-5-[(5-phenyl-2-pyridinyl)carbonyl]-2,5-diazabicyclo[2.2.1]hept-2-yl}carbonyl)butyl]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-1-methyl-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-[(trifluoromethyl)oxy]-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-(methyloxy)-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-chloro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-4-methyl-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-7-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-6-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-5-fluoro-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-4-methyl-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-hydroxy-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-hydroxy-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-6-methyl-1H-indole-2-carboxamide;

6-chloro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

6-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

5-fluoro-N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-methyl-1H-indole-2-carboxamide;

6-chloro-N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-fluoro-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-5-fluoro-1H-indole-2-carboxamide;

N-((1S)-1-{[(1S,4S)-5-(1H-benzimidazol-2-ylcarbonyl)-2,5-diazabicyclo[2.2.1]hept-2-yl]carbonyl}-2,2-dimethylpropyl)-N-methyl-1H-indole-2-carboxamide;

N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-N-methyl-1H-indole-2-carboxamide;

N-[(1S)-2,2-dimethyl-1-({(1S,4S)-5-[(1-phenyl-1H-imidazol-4-yl)carbonyl]-2,5-diazabicyclo[2.2.1]hept-2-yl}carbonyl)propyl]-N-methyl-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-N-methyl-1H-indole-2-carboxamide;

N-((1S)-1-{[(1S,4S)-5-({5-[4-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide;

2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic;

4-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]benzoic;

N-((1S)-1-{[(1S,4S)-5-({5-[2-(ethyloxy)phenyl]-2-pyridinyl}carbonyl)-2,5-diazabicyclo[2.2.1]hept-2-yl]carbonyl}-2,2-dimethylpropyl)-1H-indole-2-carboxamide;

N-{(1S)-2,2-dimethyl-1-[((1S,4S)-5-{[5-(2-methylphenyl)-2-pyridinyl]carbonyl}-2,5-diazabicyclo[2.2.1]hept-2-yl)carbonyl]propyl}-1H-indole-2-carboxamide;

N-{(1S)-1-[((1S,4S)-5-{[5-(2-chlorophenyl)-2-pyridinyl]carbonyl}-2,5-diazabicyclo[2.2.1]hept-2-yl)carbonyl]-2,2-dimethylpropyl}-1H-indole-2-carboxamide;

N-{(1S)-1-[((1S,4S)-5-{[5-(2-fluorophenyl)-2-pyridinyl]carbonyl}-2,5-diazabicyclo[2.2.1]hept-2-yl)carbonyl]-2,2-dimethylpropyl}-1H-indole-2-carboxamide;

N-((1S)-2,2-dimethyl-1-{[(1S,4S)-5-({5-[2-(methyloxy)phenyl]-2-pyridinyl}carbonyl)-2,5-diazabicyclo[2.2.1]hept-2-yl]carbonyl}propyl)-1H-indole-2-carboxamide;

N-{(1S)-1-[((1S,4S)-5-{[5-(3-cyanophenyl)-2-pyridinyl]carbonyl}-2,5-diazabicyclo[2.2.1]hept-2-yl)carbonyl]-2,2-dimethylpropyl}-1H-indole-2-carboxamide;

N-((1S)-1-{[(1S,4S)-5-({5-[3-(dimethylamino)phenyl]-2-pyridinyl}carbonyl)-2,5-diazabicyclo[2.2.1]hept-2-yl]carbonyl}-2,2-dimethylpropyl)-1H-indole-2-carboxamide;

N-((1S)-2,2-dimethyl-1-{[(1S,4S)-5-({5-[4-(methylsulfonyl)phenyl]-2-pyridinyl}carbonyl)-2,5-diazabicyclo[2.2.1]hept-2-yl}carbonyl)propyl]-1H-indole-2-carboxamide;

N-[(1S)-2,2-dimethyl-1-({(1S,4S)-5-[(5-{2-[(trifluoromethyl)oxy]phenyl}-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(5-{4-[(trifluoromethyl)oxy]phenyl}-2-pyridinyl)carbonyl]-2,5-diazabicyclo[2.2.1]hept-2-yl}carbonyl)propyl]-1H-indole-2-carboxamide;

N-[(1S)-2,2-dimethyl-1-({(1S,4S)-5-[(5-{3-[(trifluoromethyl)oxy]phenyl}-2-pyridinyl)carbonyl]-2,5-diazabicyclo[2.2.1]hept-2-yl}carbonyl)propyl]-1H-indole-2-carboxamide;

N-[(1S)-1-({(1S,4S)-5-[(6'-cyano-3,3'-bipyridin-6-yl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[5-(1H-pyrrol-2-yl)-2-pyridinyl]carbonyl}-2,5-diazabicyclo[2.2.1]hept-2-yl)carbonyl]propyl}-1H-indole-2-carboxamide;

1,1-dimethylethyl 2-[6-({(1S,4S)-5-[N-(1H-indol-2-ylcarbonyl)-3-methyl-L-valyl]-2,5-diazabicyclo[2.2.1]hept-2-yl}carbonyl)-3-pyridinyl]-1H-pyrrole-1-carboxylate;

N-{(1S)-1-[((1S,4S)-5-{[5-(3,5-dimethyl-4-isoxazolyl)-2-pyridinyl]carbonyl}-2,5-diazabicyclo[2.2.1]hept-2-yl)carbonyl]-2,2-dimethylpropyl}-1H-indole-2-carboxamide;

N-[(1S)-1-({(1S,4S)-5-[(6-chloro-2,2':6',3''-terpyridin-6''-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(6-chloro-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(5-fluoro-6-methyl-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-1-({(1S,4S)-5-[(3-fluoro-2,3'-bipyridin-6'-yl)carbonyl]-2,5-diazabicyclo[2.2.1]hept-2-yl}carbonyl)-2,2-dimethylpropyl]-1H-indole-2-carboxamide;

N-[(1S)-2,2-dimethyl-1-({(1S,4S)-5-[(3-methyl-2,3'-bipyridin-6'-yl)carbonyl]-2,5-diazabicyclo[2.2.1]hept-2-yl}carbonyl)propyl]-1H-indole-2-carboxamide;

N-[(1S)-1-({(1S,4S)-5-[(3-chloro-2,3'-bipyridin-6'-yl)carbonyl]-2,5-diazabicyclo[2.2.1]hept-2-yl}carbonyl)-2,2-dimethylpropyl]-1H-indole-2-carboxamide;

N-{(1S)-2,2-dimethyl-1-[((1S,4S)-5-{[3-(methyloxy)-2,3'-bipyridin-6'-yl]carbonyl}-2,5-diazabicyclo[2.2.1]hept-2-yl)carbonyl]propyl}-1H-indole-2-carboxamide;

or a pharmaceutically acceptable salt thereof.

2. A compound of claim 1 chosen from:
N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-1H-indole-2-carboxamide;

N-[(1S)-1-({(1S,4S)-5-[(5-cyano-2,3'-bipyridin-6'-yl)carbonyl]-2,5-diazabicyclo[2.2.1]hept-2-yl}carbonyl)-2,2-dimethylpropyl]-1H-indole-2-carboxamide;

N-{(1S)-1-[((1S,4S)-5-{[5-(4-cyanophenyl)-2-pyridinyl]carbonyl}-2,5-diazabicyclo[2.2.1]hept-2-yl)carbonyl]-2,2-dimethylpropyl}-1H-indole-2-carboxamide;

N-{(1S)-2,2-dimethyl-1-[((1S,4S)-5-{[5-(2-pyrimidinyl)-2-pyridinyl]carbonyl}-2,5-diazabicyclo[2.2.1]hept-2-yl)carbonyl]propyl}-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-5-fluoro-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-4-hydroxy-1H-indole-2-carboxamide;

N-[(1S)-2,2-dimethyl-1-({(1S,4S)-5-[(5-phenyl-2-pyridinyl)carbonyl]-2,5-diazabicyclo[2.2.1]hept-2-yl}carbonyl)propyl]-6-fluoro-1H-indole-2-carboxa;

N-[(1S)-2,2-dimethyl-1-({(1S,4S)-5-[(5-phenyl-2-pyrimidinyl)carbonyl]-2,5-diazabicyclo[2.2.1]hept-2-yl}carbonyl)propyl]-N-methyl-1H-indole-2-carboxamide or a pharmaceutically acceptable salt thereof.

3. A pharmaceutical composition comprising a compound of claim 2 and a pharmaceutically acceptable carrier or excipient.

* * * * *